(12) United States Patent
Bickers et al.

(10) Patent No.: US 7,838,463 B2
(45) Date of Patent: Nov. 23, 2010

(54) SAFENERS BASED ON ACRYLIC-ALIPHATIC CARBOXYLIC ACID DERIVATIVES

(75) Inventors: Udo Bickers, Wietmarschen (DE); Lothar Willms, Hofheim (DE); Christopher Rosinger, Hofheim (DE)

(73) Assignee: Bayer CropScience AG, Monheim (DE)

( * ) Notice: Subject to any disclaimer, the term of this patent is extended or adjusted under 35 U.S.C. 154(b) by 1761 days.

(21) Appl. No.: 10/911,669

(22) Filed: Aug. 4, 2004

(65) Prior Publication Data

US 2005/0049145 A1    Mar. 3, 2005

(30) Foreign Application Priority Data

Aug. 5, 2003    (DE)    ................. 103 35 725

(51) Int. Cl.
*A01N 25/32* (2006.01)
*A01N 37/36* (2006.01)
*A01N 47/40* (2006.01)

(52) U.S. Cl. ................ 504/109; 504/110; 514/159; 514/514

(58) Field of Classification Search ............... 504/116.1, 504/109, 110; 514/159, 514; 558/303, 416
See application file for complete search history.

(56) References Cited

U.S. PATENT DOCUMENTS

| | | | |
|---|---|---|---|
| 4,321,084 A | 3/1982 | Thomas et al. | |
| 4,375,563 A | 3/1983 | Chan et al. | |
| 4,808,208 A | 2/1989 | Lee et al. | |
| 5,573,999 A | 11/1996 | Sauter et al. | |
| 5,739,080 A | 4/1998 | Boyles et al. | |
| 5,846,902 A | 12/1998 | Boyles et al. | |
| 5,972,839 A * | 10/1999 | Ziemer et al. | ............. 504/223 |

FOREIGN PATENT DOCUMENTS

| | | |
|---|---|---|
| DE | 1542872 | 7/1970 |
| DE | 199 33 897 | 1/2001 |
| EP | 0 512 737 | 11/1992 |
| EP | 1094813 | 5/2001 |
| WO | WO-92/11761 | 7/1992 |
| WO | WO-9602518 | 2/1996 |
| WO | WO-96/14298 | 5/1996 |
| WO | WO-98/27049 | 6/1998 |

OTHER PUBLICATIONS

Hui, Y.H., Data Sourcebook for Food Scientists and Technologists, 1991, John Wiley and Sons, Table 1.2.2, pp. 90-99.*
Kurkovskaja, et al., "Magnetic Phenomena", *Chemical Abstracts*, vol. 124, No. 6 1996.
Bergmann, H., et al., "Increase of stress resistance in crop plants by using phenolic compounds," Acta Horticulturae 381:390-397 (1994).

* cited by examiner

*Primary Examiner*—Johann R Richter
*Assistant Examiner*—Andriae M Holt
(74) *Attorney, Agent, or Firm*—Connolly Bove Lodge & Hutz LLP

(57) ABSTRACT

Compounds of the formula (I) or salts thereof,

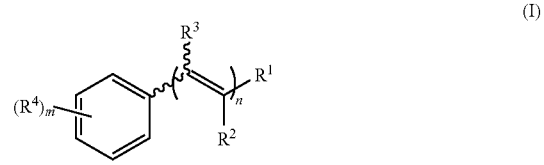

which
$R^1$ is COOH or a derivative thereof, preferably a radical of the formula —CN, —C(=X)—Y—R or —C(X'R')(X"R")—Y—R, in which
R is H, a (subst.) hydrocarbon radical, a heterocyclic radical or acyl,
Y is a direct bond or O, S, $NR^c$ or $NR^c$—$NR^dR^e$,
n is the integer 1, 2, 3, 4, 5 or 6
and
R', R", X, X', X", $R^a$, $R^b$, $R^c$, $R^d$, $R^e$, $R^2$, $R^3$ $(R^4)_m$ are as defined in claim 1 are suitable as safeners for crop plants or useful plants against phytotoxic actions of agrochemicals, preferably as safeners against the action of pesticides such as herbicides in these plants,
where compounds of the formula (I) or salts thereof in which $R^1$ is COOH, $R^2$, $R^3$ are each hydrogen, $(R^4)_m$ is a hydroxyl radical (m=1) in any position or two radicals $R^4$ (m=2) in any position, where in the latter case one radical is a hydroxyl group and the other radical is hydroxyl or methoxy, and n is the number 1, are used as safeners for crop plants or useful plants against phytotoxic actions of agrochemicals other than glyphosate.

10 Claims, No Drawings

SAFENERS BASED ON ACRYLIC-ALIPHATIC CARBOXYLIC ACID DERIVATIVES

The present invention relates to the field of safeners for protecting crop plants or useful plants against damage caused by the use of agrochemicals such as xenobiocides or biocides, for example herbicides, insecticides, acaricides, nematicides or fungicides, on said plants. Specifically, the invention relates to the novel use of certain hydroxyaromatic compounds as safeners, and to novel compounds from this group.

When controlling unwanted organisms in crops of plants which are useful for agriculture or forestry by using pesticides, the useful plants are frequently also damaged to a greater or lesser extent, in a manner which is unwanted per se, by the pesticides employed. This effect is encountered in particular with the use of a considerable number of herbicides in monocotyledonous and dicotyledonous crops of useful plants—and there primarily in the post-emergence application. In some instances, the useful plants can be protected against the phytotoxic properties of the pesticides by employing safeners or antidotes, without diminishing the pesticidal activity against the harmful organisms.

The action of the compounds which have hitherto been disclosed as safeners is frequently limited to certain crops and certain classes of pesticides. In particular, hardly any commercial safeners for dicotyledonous crops have become known. Likewise, for a number of pesticides, non-selective herbicides or total herbicides, hardly any safeners have been described.

U.S. Pat. No. 4,808,208 describes the use of phenols such as mono- or dihydroxyacetophenone or hydroxycinnamic acids and some derivatives of these carboxylic acids as safeners for soybean crops against phytotoxic actions of the herbicide glyphosate (phosphonomethylglycine and its salts).

Moreover, DE-A-19933897 discloses that the resistance of crop plants against chemical stress caused by the use of insufficiently selective agrochemicals can be improved by using resistance inductors from the group of the acylcyclohexanediones, such as prohexadione (salts) and trinexpac-ethyl or trinexpac salts, or benzothiadiazoles or benzothiazoles or derivatives thereof, such as acibenzolar-S-methyl and probenazole.

Furthermore, it is known that growth-regulator herbicides such as dicamba (2,5-di-chloro-6-methoxybenzoic acid) and phenoxyalkanecarboxylic acid derivatives (2,4-D, MCPA) have been used in some cases as crop-plant-protecting compounds for coherbicides (see, for example, U.S. Pat. No. 5,846,902, U.S. Pat. No. 5,739,080, EP-A-512737).

U.S. Pat. No. 4,321,084 describes herbicidal compositions comprising herbicidal thio-carbamates such as vernolate or butylate in combination with an antidote (=safener) from the group of the halogenated phenols. These phenols comprise known herbicides, such as the hydroxybenzonitriles bromoxynil and ioxynil, and also analogs in which the nitrile group is replaced by a carboxyl, carbalkoxy or alkyl group.

WO-A-92/11761 describes herbicide/biocide/antidote combinations where the biocide may be an insecticide, a fungicide or a nematicide and the antidotes are selected from the group of amides of different structures, which generally also includes aromatic amides, which combinations are used to avoid "negative synergism" in the interaction of herbicide and biocide.

Acta Horticulturae 381 (1994), pages 390-397 describes the use of certain derivatives of phenolic compounds, such as acetylsalicylic acid, for modulating plant growth, water uptake and osmotic pressure in plants, and their action for improving the resistance of the plants against various stress factors, such as drought, is discussed.

It has now been found that, surprisingly, compounds of the formula (I) shown below or salts thereof can be used effectively as safeners for crop plants or useful plants against damage to these plants caused by agrochemicals even of very different structures, preferably from the group of the selective or non-selective herbicides. The invention also provides novel chemical compounds which can be used as such safeners.

Accordingly, the invention provides the use of compounds of the formula (I) or salts thereof,

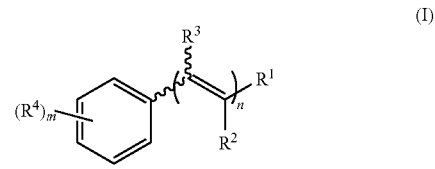

in which
R$^1$ is carboxyl or a derivative of the carboxyl group, preferably a radical of the formula —CN or —C(=X)—Y—R or

—C(X'R')(X"R—)—Y—R in which
R is hydrogen or an unsubstituted or substituted hydrocarbon radical or an unsubstituted or substituted heterocyclic radical or acyl and
R', R" independently of one another are each hydrogen, $(C_1-C_6)$alkyl, $(C_2-C_6)$alkenyl, $(C_2-C_6)$alkynyl or $(C_1-C_6)$alkanoyl, where the alkyl moiety of each of the 4 last-mentioned radicals is unsubstituted or substituted by one or more radicals selected from the group consisting of halogen, hydroxyl, $(C_1-C_6)$alkoxy and $(C_1-C_6)$haloalkoxy, or
are directly attached to one another and are together a divalent group of the formula —CH$_2$CH$_2$— or —CH$_2$CH$_2$CH$_2$— or —CH$_2$CH$_2$CH$_2$CH$_2$—, where each of the 3 last-mentioned groups is unsubstituted or substituted by one or more radicals selected from the group consisting of halogen, hydroxyl, $(C_1-C_6)$alkyl, $(C_1-C_6)$haloalkyl, $(C_1-C_6)$alkoxy and $(C_1-C_6)$haloalkoxy,
X is a divalent group of the formula O, S or NR$^a$ or N—NR$^a$R$^b$, where R$^a$ and R$^b$ are as defined below,
X', X" independently of one another are each a divalent group of the formula O, S or NR$^0$, where R$^0$ is hydrogen, $(C_1-C_6)$alkyl, $(C_1-C_6)$haloalkyl, $(C_1-C_6)$hydroxyalkyl, $(C_1-C_4)$alkoxy-$(C_1-C_4)$alkyl, [preferably $(C_1-C_4)$alkoxyalkyl], $(C_2-C_6)$alkenyl or $(C_2-C_6)$alkynyl,
Y is a direct bond or a group of the formula O, S, NR$^c$ or NR$^c$—NR$^d$R$^e$, where R$^c$, R$^d$ and R$^e$ are as defined below, and
R$^a$, R$^b$, R$^c$, R$^d$ and R$^e$ in the radicals X and Y are independently of one another and independently of the radical R (=independently of the respective specific meaning of R) each as defined for R (=like the general definition of R) or a radical of the formula —OR*, where R* is, independently of R, as defined for R, $R^2$, $R^3$ independently of one another and, in the case that n=2, 3, 4, 5 or 6, independently of the other radicals $R^2$ and $R^3$ are each hydrogen, halogen, $(C_1-C_4)$alkyl, $(C_2-C_4)$alkenyl, $(C_2-C_4)$alkynyl, $(C_1-C_4)$alkoxy, $(C_1-C_5)$alkanoyloxy or $(C_1-C_5)$alkanoyl, where each of the 6 last-mentioned radicals is unsubstituted or substituted by one or more radicals selected from the group consisting of halogen, hydroxyl, $(C_1-C_6)$alkoxy and $(C_1-C_6)$haloalkoxy, $(R^4)_m$ are m radicals $R^4$, where each of the radicals $R^4$ independently of the others is selected from the group consisting of the radicals halogen, SCN, CN, an unsubstituted or substituted hydrocarbon radical, an unsubstituted or substituted heterocyclic radical and radicals of the formula —Z*-A, where Z* is a group of the formula O or $S(O)_x$, where x=0, 1 or 2, and A is hydrogen or an unsubstituted or substituted hydrocarbon radical or an unsubstituted or substituted heterocyclic radical or an acyl radical, provided that Z*, in the case A=acyl, can only be O or S, and m is the integer 0, 1, 2, 3, 4 or 5, preferably 0, 1, 2, 3 or 4, in particular 0, 1, 2 or 3, very particularly 1 or 2, n is the integer 1, 2, 3, 4, 5 or 6, preferably 1, 2 or 3, in particular 1 or 2, very particularly 1, as safeners for crop plants or useful plants against phytotoxic actions of agrochemicals, preferably as safeners against the action of pesticides, such as herbicides, in these plants, where compounds of the formula (I) or salts thereof in which
$R^1$ is carboxyl,
$R^2$, $R^3$ are each hydrogen,
$(R^4)_m$ is a hydroxyl radical (m=1) in any position or two radicals $R^4$ (m=2) in any position, where in the latter case one radical is a hydroxyl group and the other radical is hydroxyl or methoxy, and
n is the number 1
are used as safeners for crop plants or useful plants against phytotoxic actions of agrochemicals other than glyphosate.

If, by a hydrogen shift, the compounds are capable of forming tautomers whose structure is not formally covered by formula (I), these tautomers are nevertheless embraced by the definition of the compounds of the formula (I) according to the invention.

The formula (I) also embraces all stereoisomers of the compounds whose specific stereochemical configuration is not explicitly expressed by the formula, and mixtures thereof. Such compounds of the formula (I) contain one or more asymmetrically substituted C-atoms or else double bonds which are not specifically mentioned in the formulae (I). All possible stereoisomers defined by their specific spatial form, such as enantiomers, diastereomers, Z- and E-isomers, are embraced by the formula (I) and can be obtained by customary methods from mixtures of the stereoisomers or else by stereoselective reactions in combination with the use of stereochemically pure starting materials.

By addition of a suitable inorganic or organic acid, such as, for example, HCl, HBr, $H_2SO_4$ or $HNO_3$, or else oxalic acid or sulfonic acids, to a basic group, such as, for example, amino or alkylamino, the compounds of the formula (I) are capable of forming salts. Suitable substituents which are present in deprotonated form, such as, for example, sulfonic acids or carboxylic acids, are capable of forming inner salts with groups which for their part can be protonated, such as amino groups. Salts can also be formed by replacing the hydrogen in suitable substituents, such as, for example, sulfonic acids or carboxylic acids, by an agriculturally suitable cation. These salts are, for example, metal salts, in particular alkali metal salts or alkaline earth metal salts, in particular sodium and potassium salts, or else ammonium salts, salts with organic amines or quaternary ammonium salts.

In the formula (I) and in all formulae below, the following definitions apply:

The bonds in the formula (I) which are drawn with wavy lines ("wavy") indicate that the compounds can be present as E and Z isomers with respect to the double bonds of the side chain. The formula (I) embraces both the E and the Z isomers. In many cases, the isomers are in a steady state with one another. For the application, preference is given to the thermodynamically more stable isomers.

Suitable derivatives of the carboxyl group are, in addition to or overlapping with the groups mentioned, for example: aldehyde group, keto group, ester group, thioester group, amide group, hydrazide group, hydoxamic acid group.

A hydrocarbon radical is an aliphatic, cycloaliphatic or aromatic monocyclic or, in the case of an unsubstituted or substituted hydrocarbon radical, also bicyclic or polycyclic organic radical based on the elements carbon and hydrogen, comprising, for example, the radicals alkyl, alkenyl, alkynyl, cycloalkyl, cycloalkenyl, aryl, phenyl, naphthyl, indanyl, indenyl, etc.; this applies correspondingly to hydrocarboxy radicals.

Unless defined in more detail, the hydrocarbon and hydrocarboxy radicals in the above definitions preferably have 1 to 20 carbon atoms, particularly preferably 1 to 16 carbon atoms, in particular 1 to 12 carbon atoms.

The carbon skeleton of the hydrocarbon radicals and the specific radicals alkyl, alkoxy, haloalkyl, haloalkoxy, alkylamino and alkylthio and the corresponding unsaturated and/or substituted radicals can in each case be straight-chain or branched.

The term "$(C_1-C_4)$-alkyl" is an abbreviated notation for open-chain alkyl having one to 4 carbon atoms, i.e. it comprises the radicals methyl, ethyl, 1-propyl, 2-propyl, 1-butyl, 2-butyl, 2-methylpropyl and tert-butyl. Correspondingly, general alkyl radicals having a wider stated range of carbon atoms, for example "$(C_1-C_6)$-alkyl", also comprise straight-chain or branched alkyl radicals having a larger number of carbon atoms, i.e., according to the example, also the alkyl radicals having 5 and 6 carbon atoms.

Unless specifically indicated, the lower carbon skeletons, for example those having 1 to 6 carbon atoms or, in the case of unsaturated groups, having 2 to 6 carbon atoms, are preferred for the hydrocarbon radicals, such as alkyl, alkenyl and alkynyl radicals, including in composite radicals. Alkyl radicals, including in the composite meanings, such as alkoxy, haloalkyl, etc., are, for example, methyl, ethyl, n- or i-propyl, n-, i-, t- or 2-butyl, pentyls, hexyls, such as n-hexyl, isohexyl and 1,3-dimethylbutyl, heptyls, such as n-heptyl, 1-methylhexyl and 1,4-dimethylpentyl; alkenyl and alkynyl radicals denote the possible unsaturated radicals which correspond to the meaning of the alkyl radicals; alkenyl is, for example, vinyl, allyl, 1-methyl-2-propenyl, 2-methyl-2-propenyl, 2-butenyl, pentenyl, 2-methylpentenyl or hexenyl, preferably allyl, 1-methylprop-2-en-1-yl, 2-methylprop-2-en-1-yl, but-2-en-1-yl, but-3-en-1-yl, 1-methylbut-3-en-1-yl or 1-methylbut-2-en-1-yl. $(C_2-C_6)$-Alkynyl is, for example, ethynyl, propargyl, 1-methyl-2-propynyl, 2-methyl-2-propynyl, 2-butynyl, 2-pentynyl or 2-hexynyl, preferably propargyl, but-2-yn-1-yl, but-3-yn-1-yl or 1-methyl but-3-yn-1-yl.

Alkylidene, for example also in the form of $(C_1-C_{10})$-alkylidene, denotes the radical of a straight-chain or branched alkane which is attached via a double bond, where the position of the point of attachment has not yet been determined. In the case of a branched alkane, of course, only those positions are suitable where two hydrogen atoms can be replaced by the double bond; such radicals are, for example, =CH$_2$, =CH—CH$_3$, =C(CH$_3$)—CH$_3$, =C(CH$_3$)—C$_2$H$_5$ or =C(C$_2$H$_5$)—C$_2$H$_5$.

Cycloalkyl denotes a carbocyclic saturated ring system having preferably 3-8 carbon atoms, for example cyclopropyl, cyclobutyl, cyclopentyl or cyclohexyl. Substituted cycloalkyl comprises cyclic systems having substituents, including substituents having a double bond to the cycloalkyl radical, for example an alkylidene group, such as methylidene. Substituted cycloalkyl also comprises polycyclic aliphatic systems, such as, for example, bicyclo[1.1.0]butan-1-yl, bicyclo[1.1.0]butan-2-yl, bicyclo-[2.1.0]pentan-1-yl, bicyclo[2.1.0]pentan-2-yl, bicyclo[2.1.0]pentan-5-yl, adamantan-1-yl and adamantan-2-yl.

Cycloalkenyl denotes a carbocyclic non-aromatic partially unsaturated ring system having preferably 4-8 carbon atoms, for example 1-cyclobutenyl, 2-cyclobutenyl, 1-cyclopentenyl, 2-cyclopentenyl, 3-cyclopentenyl, or 1-cyclohexenyl, 2-cyclo-hexenyl, 3-cyclohexenyl, 1,3-cyclohexadienyl or 1,4-cyclohexadienyl. In the case of substituted cycloalkenyl, the comments for substituted cycloalkyl apply correspondingly.

Halogen denotes, for example, fluorine, chlorine, bromine or iodine. Haloalkyl, -alkenyl and -alkynyl denote alkyl, alkenyl and alkynyl, respectively, which are partially or fully substituted by identical or different halogen atoms, preferably selected from the group consisting of fluorine, chlorine and bromine, in particular the group consisting of fluorine and chlorine, for example monohaloalkyl, perhaloalkyl, CF$_3$, CHF$_2$, CH$_2$F, CF$_3$CF$_2$, CH$_2$FCHCl, CCl$_3$, CHCl$_2$, CH$_2$CH$_2$Cl; haloalkoxy is, for example, OCF$_3$, OCHF$_2$, OCH$_2$F, CF$_3$CF$_2$O, OCH$_2$CF$_3$ and OCH$_2$CH$_2$Cl; this applies correspondingly to haloalkenyl and other halogen-substituted radicals.

Aryl denotes a mono-, bi- or polycyclic aromatic system, for example phenyl, naphthyl, tetrahydronaphthyl, indenyl, indanyl, pentalenyl, fluorenyl and the like, preferably phenyl.

A heterocyclic radical or ring (heterocyclyl) can be saturated, unsaturated or hetero-aromatic; unless defined otherwise, it preferably contains one or more, in particular 1, 2 or 3, heteroatoms in the heterocyclic ring, preferably selected from the group consisting of N, 0 and S; it is preferably an aliphatic heterocyclyl radical having 3 to 7 ring atoms or a heteroaromatic radical having 5 or 6 ring atoms. The heterocyclic radical can, for example, be a heteroaromatic radical or ring (heteroaryl), such as, for example, a mono-, bi- or polycyclic aromatic system in which at least 1 ring contains one or more heteroatoms. It is preferably a heteroaromatic ring having a heteroatom selected from the group consisting of N, O and S, for example pyridyl, pyrrolyl, thienyl or furyl; moreover, it is preferably a corresponding heteroaromatic ring having 2 or 3 heteroatoms, for example pyrimidinyl, pyridazinyl, pyrazinyl, triazinyl, thiazolyl, thiadiazolyl, oxazolyl, isoxazolyl, pyrazolyl, imidazolyl and triazolyl. Moreover, it is preferably a partially or fully hydrogenated heterocyclic radical having a heteroatom selected from the group consisting of N, O and S, for example oxiranyl, oxetanyl, oxolanyl (=tetrahydrofuryl), oxanyl, pyrrolinyl, pyrrolidyl or piperidyl.

Moreover, it is preferably a partially or fully hydrogenated heterocyclic radical having 2 heteroatoms selected from the group consisting of N, O and S, for example piperazinyl, dioxolanyl, oxazolinyl, isoxazolinyl, oxazolidinyl, isoxazolidinyl and morpholinyl.

Suitable substituents for a substituted heterocyclic radical are the substituents mentioned further below, and additionally also oxo. The oxo group may also be present on the heterocyclic ring atoms which can exist in various oxidation states, for example on N and S.

Preferred examples of heterocyclyl are heterocyclic radicals having 3 to 6 ring atoms selected from the group consisting of pyridyl, thienyl, furyl, pyrrolyl, oxiranyl, 2-oxetanyl, 3-oxetanyl, oxolanyl (=tetrahydrofuryl), pyrrolidyl, piperidyl, in particular oxiranyl, 2-oxetanyl, 3-oxetanyl or oxolanyl, or heterocyclic radicals having two or three heteroatoms, for example pyrimidinyl, pyridazinyl, pyrazinyl, triazinyl, thienyl, thiazolyl, thiadiazolyl, oxazolyl, isoxazolyl, pyrazolyl, triazolyl, piperazinyl, dioxolanyl, oxazolinyl, isoxazolinyl, oxazolidinyl, isoxazolidinyl or morpholinyl.

If a basic structure is substituted "by one or more radicals" from a list of radicals (=group) or a generically defined group of radicals, this includes in each case the simultaneous substitution by a plurality of identical and/or structurally different radicals.

Substituted radicals, such as substituted alkyl, alkenyl, alkynyl, aryl, phenyl, benzyl, heterocyclyl and heteroaryl radicals, are, for example, substituted radicals derived from an unsubstituted basic structure, the substituents being, for example, one or more, preferably 1, 2 or 3, radicals selected from the group consisting of halogen, alkoxy, alkylthio, hydroxyl, amino, nitro, carboxyl, cyano, azido, alkoxycarbonyl, alkylcarbonyl, formyl, carbamoyl, mono- and dialkylaminocarbonyl, substituted amino, such as acylamino, mono- and dialkylamino, and alkylsulfinyl, alkylsulfonyl and, in the case of cyclic radicals, also alkyl, haloalkyl, alkylthioalkyl, alkoxyalkyl, unsubstituted or substituted mono- and dialkylaminoalkyl and hydroxyalkyl; the term "substituted radicals" such as substituted alkyl, etc. includes, as substituents, in addition to the saturated hydrocarbon-containing radicals mentioned, corresponding unsaturated aliphatic and aromatic radicals, such as unsubstituted or substituted alkenyl, alkynyl, alkenyloxy, alkynyloxy, phenyl, phenoxy, etc. Substituted cyclic radicals having aliphatic moieties in the ring also include cyclic systems having substituents attached to the ring via a double bond, for example those which are substituted by an alkylidene group, such as methylidene or ethylidene, or an oxo group, imino group or substituted imino group.

The substituents mentioned by way of example ("first substituent level") can, if they contain hydrocarbon-containing moieties, be, if appropriate, substituted further in the moieties ("second substituent level"), for example by one of the substituents as defined for the first substituent level. Corresponding further substituent levels are possible. The term "substituted radical" preferably embraces only one or two substituent levels.

Preferred substituents for the substituent levels are, for example, amino, hydroxyl, halogen, nitro, cyano, mercapto, carboxyl, carboxamide, SF$_5$, aminosulfonyl, alkyl, cycloalkyl, alkenyl, cycloalkenyl, alkynyl, monoalkylamino, dialkylamino, N-alkanoylamino, alkoxy, alkenyloxy, alkynyloxy, cycloalkoxy, cycloalkenyloxy, alkoxycarbonyl, alkenyloxycarbonyl, alkynyloxycarbonyl, aryloxycarbonyl, alkanoyl, alkenylcarbonyl, alkynylcarbonyl, arylcarbonyl, alkylthio, cycloalkylthio, alkenylthio, cycloalkenylthio, alkynylthio, alkylsulfinyl, alkylsulfonyl, monoalkylaminosulfonyl, dialkylaminosulfonyl, N-alkylaminocarbonyl, N,N-dialkylaminocarbonyl, N-alkanoylaminocarbonyl, N-alkanoyl-N-alkylaminocarbonyl, aryl, aryloxy, benzyl, benzyloxy, benzylthio, arylthio, arylamino and benzylamino.

In the case of radicals having carbon atoms, preference is given to those having 1 to 6 carbon atoms, preferably 1 to 4 carbon atoms, in particular 1 or 2 carbon atoms. Preference is generally given to substituents selected from the group consisting of halogen, for example fluorine and chlorine, ($C_1$-$C_4$)-alkyl, preferably methyl or ethyl, ($C_1$-$C_4$)-haloalkyl, preferably trifluoromethyl, ($C_1$-$C_4$)-alkoxy, preferably methoxy or ethoxy, ($C_1$-$C_4$)-haloalkoxy, nitro and cyano. Here, particular preference is given to the substituents methyl, methoxy, fluorine and chlorine.

Substituted amino, such as mono- or disubstituted amino, denotes a radical from the group of the substituted amino radicals which are N-substituted, for example, by one or two identical or different radicals selected from the group consisting of alkyl, alkoxy, acyl and aryl; preferably mono- and dialkylamino, mono- and diarylamino, acylamino, N-alkyl-N-arylamino, N-alkyl-N-acylamino and N-heterocycles; here, preference is given to alkyl radicals having 1 to 4 carbon atoms; aryl is preferably phenyl or substituted phenyl; for acyl, the definition given further down applies, preference is given to ($C_1$-$C_4$)-alkanoyl. This applies correspondingly to substituted hydroxylamino or hydrazino.

Unsubstituted or substituted phenyl is preferably phenyl which is unsubstituted or mono- or polysubstituted, preferably up to trisubstituted, by identical or different radicals selected from the group consisting of halogen, ($C_1$-$C_4$)-alkyl, ($C_1$-$C_4$)-alkoxy, ($C_1$-$C_4$)-haloalkyl, ($C_1$-$C_4$)-haloalkoxy and nitro, for example o-, m- and p-tolyl, dimethylphenyls, 2-, 3- and 4-chlorophenyl, 2-, 3- and 4-trifluoro- and -trichlorophenyl, 2,4-, 3,5-, 2,5- and 2,3-dichlorophenyl, o-, m- and p-methoxyphenyl.

Acyl denotes a radical of an organic acid which, formally, is formed by removing a hydroxyl group from the acid function, it also being possible for the organic radical in the acid to be attached to the acid function via a heteroatom. Examples of acyl are the radical —CO—R of a carboxylic acid HO—CO—R and radicals of acids derived therefrom, such as thiocarboxylic acid, unsubstituted or N-substituted iminocarboxylic acids or the radical of carbonic acid monoesters, N-substituted carbamic acid, sulfonic acids, sulfinic acids, N-substituted sulfonamido acids, phosphonic acids, phosphinic acids.

Acyl denotes, for example, formyl, alkylcarbonyl, such as [($C_1$-$C_4$)-alkyl]carbonyl, phenylcarbonyl, alkyloxycarbonyl, phenyloxycarbonyl, benzyloxycarbonyl, alkylsulfonyl, alkylsulfinyl, N-alkyl-1-iminoalkyl and other radicals of organic acids. Here, the radicals may in each case be substituted further in the alkyl or phenyl moiety, for example in the alkyl moiety by one or more radicals selected from the group consisting of halogen, alkoxy, phenyl and phenoxy; examples of substituents in the phenyl moiety are the substituents which have already been mentioned further up in a general manner for substituted phenyl.

Acyl denotes preferably an acyl radical in the narrower sense, i.e. a radical of an organic acid where the acid group is attached directly to the carbon atom of an organic radical, for example formyl, alkylcarbonyl, such as acetyl or [($C_1$-$C_4$)alkyl]carbonyl, phenylcarbonyl, alkylsulfonyl, alkylsulfinyl and other radicals of organic acids.

If a general radical is defined as "hydrogen", this means a hydrogen atom. The "yl-position" of a radical (for example of an alkyl radical) denotes its point of attachment.

Hereinbelow, compounds of formula (I) and salts thereof which can be used according to the invention are, in short, also referred to as "compounds (I) according to the invention".

In particular for reasons of better action, better selectivity and/or better preparability, the use according to the invention of compounds of the formula (I) mentioned or salts thereof is of particular interest in which individual radicals have one of the preferred meanings already mentioned or mentioned below, or in particular those which contain a combination of one or more of the preferred meanings already mentioned or mentioned below.

Of particular interest is the use according to the invention of compounds of the formula (I) or salts thereof in which $R^1$ is a nitrile group (—CN).

Of particular interest is also the use according to the invention of compounds of the formula (I) or salts thereof in which $R^1$ is a radical of the formula

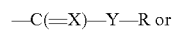

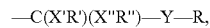

in which

R is hydrogen, ($C_1$-$C_{18}$)alkyl, ($C_2$-$C_{18}$)alkenyl, ($C_2$-$C_{18}$)alkynyl, ($C_3$-$C_9$)cycloalkyl, ($C_5$-$C_9$)cycloalkenyl, ($C_3$-$C_9$)cycloalkyl-($C_1$-$C_{12}$)alkyl, phenyl, phenyl-($C_1$-$C_{12}$)alkyl, heterocyclyl or heterocyclyl-($C_1$-$C_{12}$)alkyl, where each of the 10 last-mentioned radicals is unsubstituted or substituted by one or more radicals selected from the group consisting of halogen, hydroxyl, amino, cyano, nitro, thiocyanato, ($C_1$-$C_4$)alkoxy, ($C_1$-$C_4$)haloalkoxy, ($C_2$-$C_4$)alkenyloxy, ($C_2$-$C_4$)haloalkenyloxy, ($C_1$-$C_4$)alkylthio, ($C_1$-$C_4$)alkylsulfinyl, ($C_1$-$C_4$)alkylsulfonyl, ($C_1$-$C_4$)haloalkylsulfinyl, ($C_1$-$C_4$)haloalkylsulfonyl, mono($C_1$-$C_4$)alkylamino, di($C_1$-$C_4$)alkylamino, ($C_1$-$C_4$)alkanoyl, ($C_1$-$C_4$)haloalkanoyl, [($C_1$-$C_4$)alkoxy]carbonyl, [($C_1$-$C_4$)haloalkoxy]carbonyl, aminocarbonyl, mono[($C_1$-$C_4$)alkylamino]carbonyl, di[($C_1$-$C_4$)alkylamino]carbonyl and, in the case of cyclic radicals, also ($C_1$-$C_4$)alkyl and ($C_1$-$C_4$)haloalkyl, or ($C_1$-$C_6$)alkanoyl, ($C_1$-$C_4$)haloalkanoyl, [($C_1$-$C_4$)alkoxy]carbonyl, [($C_1$-$C_4$)haloalkoxy]carbonyl, phenylcarbonyl, phenoxycarbonyl, [phenyl-($C_1$-$C_4$)alkyl]carbonyl, [phenyl-($C_1$-$C_4$)alkoxy]carbonyl, where the phenyl ring of each of the 4 last-mentioned radicals is unsubstituted or substituted, aminocarbonyl, mono[($C_1$-$C_4$)alkylamino]carbonyl, di[($C_1$-$C_4$)alkylamino]-carbonyl, ($C_1$-$C_4$)alkylsulfinyl, ($C_1$-$C_4$)alkylsulfonyl, ($C_1$-$C_4$)haloalkylsulfinyl or ($C_1$-$C_4$)haloalkylsulfonyl, where R, including substituents, has 1 to 30 carbon atoms, preferably 1 to 20 carbon atoms, in particular 1 to 16 carbon atoms, and/or R', R" independently of one another are each ($C_1$-$C_6$)alkyl, ($C_2$-$C_6$)alkenyl, ($C_2$-$C_6$)alkynyl or ($C_1$-$C_6$)alkanoyl, where each of the 4 last-mentioned radicals is unsubstituted or substituted by one or more radicals selected from the group consisting of halogen, hydroxyl, ($C_1$-$C_6$)alkoxy and ($C_1$-$C_6$)haloalkoxy, or are directly attached to one another and are a divalent group of the formula —$CH_2CH_2$— or —$CH_2CH_2CH_2$— or —$CH_2CH_2CH_2CH_2$—, where each of the 3 last-mentioned groups is unsubstituted or substituted by one or more radicals selected from the group consisting of halogen, hydroxyl, ($C_1$-$C_4$)alkyl, ($C_1$-$C_4$)haloalkyl, ($C_1$-$C_4$)alkoxy and ($C_1$-$C_4$)haloalkoxy, X is a divalent group of the formula O, S or NR$^a$ or N—NR$^a$R$^b$, where R$^a$ and R$^b$ are as defined below, X', X" independently of one another are each a divalent group of the formula O, S or NR$^0$, where R$^0$ is hydrogen, (C$_1$-C$_4$)alkyl, (C$_1$-C$_4$)haloalkyl, (C$_1$-C$_4$)hydroxyalkyl, (C$_1$-C$_4$)alkoxy-(C$_1$-C$_4$)alkyl, [preferably (C$_2$-C$_4$)alkoxyalkyl](C$_2$-C$_4$)alkenyl or (C$_2$-C$_4$)alkynyl, Y is a direct bond or a divalent group of the formula O, S, NR$^c$ or NR$^c$—NR$^d$R$^e$, where R$^c$, R$^d$ and R$^e$ are as defined below, and R$^a$, R$^b$, R$^c$, R$^d$ and R$^e$ in the radicals X and Y independently of one another and of the radical R are each as defined for R or a radical of the formula —OR*, where R* is, independently of R, as defined for R.

Here, in the definitions, heterocyclyl is preferably an aliphatic or aromatic heterocycle having a total of 1 to 3 heterocyclic ring atoms from the group consisting of N, O and S and a total of 5 or 6 ring atoms which is unsubstituted or substituted by one or more radicals selected from the group consisting of halogen, hydroxyl, amino, (C$_1$-C$_4$)alkyl, (C$_1$-C$_4$)alkoxy, (C$_1$-C$_4$)haloalkyl, (C$_1$-C$_4$)haloalkoxy, (C$_1$-C$_4$)alkylthio and oxo.

Of particular interest is also the use according to the invention of compounds of the formula (I) or salts thereof in which R$^1$ is a radical of the formula —C(=X)—Y—R or —C(X'R')(X"R")—Y—R, in which R is hydrogen, (C$_1$-C$_{12}$)alkyl, (C$_2$-C$_{12}$)alkenyl, (C$_2$-C$_{12}$)alkynyl, (C$_3$-C$_6$)cycloalkyl, (C$_5$-C$_6$)cycloalkenyl, (C$_3$-C$_6$)cycloalkyl-(C$_1$-C$_4$)alkyl, phenyl, phenyl-(C$_1$-C$_4$)alkyl, heterocyclyl or heterocyclyl-(C$_1$-C$_4$)alkyl, where each of the 10 last-mentioned radicals is unsubstituted or substituted by one or more radicals selected from the group consisting of halogen, hydroxyl, (C$_1$-C$_4$)alkoxy, (C$_1$-C$_4$)haloalkoxy, (C$_2$-C$_4$)alkenyloxy, (C$_2$-C$_4$)haloalkenyloxy, (C$_1$-C$_4$)alkylthio, (C$_1$-C$_4$)alkylsulfinyl, (C$_1$-C$_4$)alkylsulfonyl, (C$_1$-C$_4$)haloalkylsulfinyl, (C$_1$-C$_4$)haloalkylsulfonyl, mono(C$_1$-C$_4$)alkylamino, di(C$_1$-C$_4$)alkylamino, (C$_1$-C$_4$)alkanoyl, (C$_1$-C$_4$)haloalkanoyl, [(C$_1$-C$_4$)alkoxy]carbonyl, [(C$_1$-C$_4$)haloalkoxy]carbonyl, aminocarbonyl, mono[(C$_1$-C$_4$)alkylamino]carbonyl, di[(C$_1$-C$_4$)alkylamino]carbonyl and, in the case of cyclic radicals, also (C$_1$-C$_4$)alkyl and (C$_1$-C$_4$)haloalkyl, or (C$_1$-C$_4$)alkanoyl, (C$_1$-C$_4$)haloalkanoyl, [(C$_1$-C$_4$)alkoxy]carbonyl, [(C$_1$-C$_4$)haloalkoxy]carbonyl, phenylcarbonyl, phenoxycarbonyl, [phenyl-(C$_1$-C$_4$)alkyl]carbonyl, [phenyl-(C$_1$-C$_4$)alkoxy]carbonyl, aminocarbonyl, mono[(C$_1$-C$_4$)alkylamino]carbonyl, di[(C$_1$-C$_4$)alkylamino]carbonyl, (C$_1$-C$_4$)alkylsulfinyl, (C$_1$-C$_4$)alkylsulfonyl, (C$_1$-C$_4$)haloalkylsulfinyl or (C$_1$-C$_4$)haloalkylsulfonyl, X is a divalent group of the formula O, S or NR$^a$ or N—NR$^a$R$^b$, where R$^a$ and R$^b$ are as defined below, X', X" independently of one another are each a divalent group of the formula O, S or NR$^0$, where R$^0$ is hydrogen, (C$_1$-C$_4$)alkyl, (C$_1$-C$_4$)haloalkyl, (C$_1$-C$_4$)hydroxyalkyl, (C$_2$-C$_4$)alkenyl or (C$_2$-C$_4$)alkynyl, Y is a direct bond or a divalent group of the formula O, S NR$^c$ or NR$^c$—NR$^d$R$^e$, where R$^c$, R$^d$ and R$^e$ are as defined below, and R$^a$, R$^b$, R$^c$, R$^d$ and R$^e$ in the radicals X and Y independently of one another and of the radical R are as defined for R or a radical of the formula —OR*, where R* is, independently of R, as defined for R.

Preference is given to the use according to the invention of compounds of the formula (I) or salts thereof in which
R$^1$ is a radical of the formula —C(=X)—Y—R or —C(X'R')(X"R")—Y—R, preferably of the formula —C(=X)—Y—R, in which R is hydrogen, (C$_1$-C$_8$)alkyl, (C$_2$-C$_8$)alkenyl, (C$_2$-C$_8$)alkynyl, (C$_3$-C$_6$)cycloalkyl, (C$_3$-C$_6$)cycloalkyl-(C$_1$-C$_4$)alkyl, phenyl, phenyl-(C$_1$-C$_4$)alkyl, heterocyclyl or heterocyclyl-(C$_1$-C$_4$)alkyl, where each of the 9 last-mentioned radicals is unsubstituted or substituted by one or more radicals selected from the group consisting of halogen, hydroxyl, (C$_1$-C$_4$)alkoxy, (C$_1$-C$_4$)haloalkoxy, (C$_1$-C$_4$)alkylthio, (C$_1$-C$_4$)alkylsulfinyl, (C$_1$-C$_4$)alkylsulfonyl, mono(C$_1$-C$_4$)alkylamino, di(C$_1$-C$_4$)alkylamino, (C$_1$-C$_4$)alkanoyl, (C$_1$-C$_4$)haloalkanoyl, [(C$_1$-C$_4$)alkoxy]carbonyl and, in the case of cyclic radicals, also (C$_1$-C$_4$)alkyl and (C$_1$-C$_4$)haloalkyl, or (C$_1$-C$_4$)alkanoyl, (C$_1$-C$_4$)haloalkanoyl, [(C$_1$-C$_4$)alkoxy]carbonyl, [(C$_1$-C$_4$)haloalkoxy]carbonyl, phenylcarbonyl, phenoxycarbonyl, [phenyl-(C$_1$-C$_4$)alkyl]carbonyl, [phenyl-(C$_1$-C$_4$)alkoxy]carbonyl, aminocarbonyl, mono[(C$_1$-C$_4$)alkylamino]carbonyl, di[(C$_1$-C$_4$)alkylamino]carbonyl, (C$_1$-C$_4$)alkylsulfinyl, (C$_1$-C$_4$)alkylsulfonyl, (C$_1$-C$_4$)haloalkylsulfinyl or (C$_1$-C$_4$)haloalkylsulfonyl, X is a divalent group of the formula O, S or NR$^a$ or N—NR$^a$R$^b$, where R$^a$ and R$^b$ are as defined below, X', X" independently of one another are each a divalent group of the formula O, S or NR$^0$, where R$^0$ is (C$_1$-C$_4$)alkyl, Y is a direct bond or a divalent group of the formula O, S, NR$^c$ or NR$^c$—NR$^d$R$^e$, where R$^c$, R$^d$ and R$^e$ are as defined below, and R$^a$, R$^b$, R$^c$, R$^d$ and R$^e$ in the radicals X and Y in each case independently of one another and of the radical R are as defined for R or a radical of the formula —OR*, where R* is, independently of R, as defined for R.

Particularly preferred is the use according to the invention of compounds of the formula (I) or salts thereof in which R$^1$ is a radical of the formula —CO—OR or —C(=NR$^a$)—OR or —CO—NR$^c$R or —CO—R or —C(=NR$^a$)—R, where R, R$^a$ and R$^b$ are as defined above.
Preferably
R$^1$ is a radical of the formula —CO—OR, where
R is hydrogen, (C$_1$-C$_8$)-alkyl, (C$_2$-C$_8$)-alkenyl, (C$_2$-C$_8$)-alkynyl, (C$_3$-C$_6$)-cycloalkyl, (C$_3$-C$_6$)-cycloalkyl-(C$_1$-C$_4$)-alkyl, phenyl, phenyl-(C$_1$-C$_4$)-alkyl, heterocyclyl or heterocyclyl-(C$_1$-C$_4$)-alkyl, where each of the 9 last-mentioned radicals is unsubstituted or substituted by one or more radicals selected from the group consisting of halogen, hydroxyl, (C$_1$-C$_4$)-alkoxy, (C$_1$-C$_4$)-haloalkoxy, (C$_1$-C$_4$)-alkylthio, (C$_1$-C$_4$)-alkylsulfinyl, (C$_1$-C$_4$)-alkylsulfonyl, mono-(C$_1$-C$_4$)-alkylamino, di-(C$_1$-C$_4$)-alkylamino, (C$_1$-C$_4$)-alkanoyl, (C$_1$-C$_4$)-haloalkanoyl, [(C$_1$-C$_4$)-alkoxy]-carbonyl and, in the case of cyclic radicals, also (C$_1$-C$_4$)-alkyl and (C$_1$-C$_4$)-haloalkyl, and, in particular R is hydrogen, $(C_1-C_6)$-alkyl, $(C_2-C_8)$-alkenyl, $(C_2-C_8)$-alkynyl, $(C_3-C_6)$-cycloalkyl, or $(C_3-C_6)$-cycloalkyl-$(C_1-C_4)$-alkyl, where each of the 5 last-mentioned radicals is unsubstituted or substituted by one or more radicals selected from the group consisting of halogen, hydroxyl, $(C_1-C_4)$-alkoxy, $(C_1-C_4)$-alkylthio and, in the case of cyclic radicals, also $(C_1-C_4)$-alkyl.

Very preferably, $R^1$ is a radical of the formula

—CO—OH or

—CO—O$^-$M$^+$ or

—CO—OR, where

R is $(C_1-C_4)$-alkyl, which is unsubstituted or substituted by one or more radicals selected from the group consisting of halogen, hydroxyl, $(C_1-C_4)$-alkoxy and $(C_1-C_4)$-alkylthio, and M$^+$ is an agriculturally suitable cation, preferably one cation equivalent of an alkali metal or alkaline earth metal, in particular a sodium ion or potassium ion, or else an unsubstituted or substituted ammonium ion, preferably $NH_4^+$ or an ammonium ion of organic amines or a quaternary ammonium ion.

Examples of such radicals are:

$R^1$=carboxyl and salts thereof, methoxycarbonyl, ethoxycarbonyl, n-propoxycarbonyl, n-butoxycarbonyl, isopropoxycarbonyl, (2-hydroxyethoxy)-carbonyl.

Preferably, $R^1$ is also a radical of the formula

—C(=NR$^a$)—OR, where

R and R$^a$ are as defined above, preferably

R is $(C_1-C_8)$-alkyl, $(C_2-C_8)$-alkenyl, $(C_2-C_8)$-alkynyl, $(C_3-C_6)$-cycloalkyl, $(C_3-C_6)$-cycloalkyl-$(C_1-C_4)$-alkyl, phenyl, phenyl-$(C_1-C_4)$-alkyl, heterocyclyl or heterocyclyl-$(C_1-C_4)$-alkyl, where each of the 9 last-mentioned radicals is unsubstituted or substituted by one or more radicals selected from the group consisting of halogen, hydroxyl, $(C_1-C_4)$-alkoxy, $(C_1-C_4)$-haloalkoxy, $(C_1-C_4)$-alkylthio, $(C_1-C_4)$-alkylsulfinyl, $(C_1-C_4)$-alkylsulfonyl, mono-$(C_1-C_4)$-alkylamino, di-$(C_1-C_4)$-alkylamino, $(C_1-C_4)$-alkanoyl, $(C_1-C_4)$-haloalkanoyl, [$(C_1-C_4)$-alkoxy]carbonyl and, in the case of cyclic radicals, also $(C_1-C_4)$-alkyl and $(C_1-C_4)$-haloalkyl, or $(C_1-C_4)$-alkanoyl, $(C_1-C_4)$-haloalkanoyl, [$(C_1-C_4)$-alkoxy]carbonyl, [$(C_1-C_4)$-halo-alkoxy]carbonyl, phenylcarbonyl, phenoxycarbonyl, [phenyl-$(C_1-C_4)$-alkyl]carbonyl, [phenyl-$(C_1-C_4)$-alkoxy]carbonyl, aminocarbonyl, mono-[$(C_1-C_4)$-alkylamino]carbonyl, di-[$(C_1-C_4)$-alkylamino]carbonyl, $(C_1-C_4)$-alkylsulfinyl, $(C_1-C_4)$-alkylsulfonyl, $(C_1-C_4)$-haloalkylsulfinyl or $(C_1-C_4)$-haloalkylsulfonyl.

Examples of such radicals are:

$R^1$=methoxyacetiminocarbonyl, ethoxyacetiminocarbonyl, n-propoxyacetiminocarbonyl, isopropoxyacetiminocarbonyl, (2-hydroxyethoxy)acetiminocarbonyl, acetoxyiminocarbonyl, acetoxymethyliminocarbonyl, acetoxyethyliminocarbonyl, acetoxyacetiminocarbonyl.

Preferably, $R^1$ is also a radical of the formula

—CO—NR$^c$R, where R and R$^c$ are as defined above; preferably,

R is hydrogen, $(C_1-C_8)$-alkyl, $(C_2-C_8)$-alkenyl, $(C_2-C_8)$-alkynyl, $(C_3-C_6)$-cycloalkyl, $(C_3-C_6)$-cycloalkyl-$(C_1-C_4)$-alkyl, phenyl, phenyl-$(C_1-C_4)$-alkyl, heterocyclyl or heterocyclyl-$(C_1-C_4)$-alkyl, where each of the 9 last-mentioned radicals is unsubstituted or substituted by one or more radicals selected from the group consisting of halogen, hydroxyl, $(C_1-C_4)$-alkoxy, $(C_1-C_4)$-haloalkoxy, $(C_1-C_4)$-alkylthio, $(C_1-C_4)$-alkylsulfinyl, $(C_1-C_4)$-alkylsulfonyl, mono-$(C_1-C_4)$alkylamino, di-$(C_1-C_4)$-alkylamino, $(C_1-C_4)$-alkanoyl, $(C_1-C_4)$-haloalkanoyl, [$(C_1-C_4)$-alkoxy]carbonyl and, in the case of cyclic radicals, also $(C_1-C_4)$-alkyl and $(C_1-C_4)$-haloalkyl, or $(C_1-C_4)$-alkanoyl, $(C_1-C_4)$-haloalkanoyl, [$(C_1-C_4)$-alkoxy]carbonyl, [$(C_1-C_4)$-halo-alkoxy]carbonyl, phenylcarbonyl, phenoxycarbonyl, [phenyl-$(C_1-C_4)$-alkyl]carbonyl, [phenyl-$(C_1-C_4)$-alkoxy]carbonyl, aminocarbonyl, mono-[$(C_1-C_4)$-alkylamino]carbonyl, di-[$(C_1-C_4)$-alkylamino]carbonyl, $(C_1-C_4)$-alkylsulfinyl, $(C_1-C_4)$-alkylsulfonyl, $(C_1-C_4)$-haloalkylsulfinyl or $(C_1-C_4)$-haloalkylsulfonyl and R$^c$ is hydrogen or, independently of one another, is defined as the radical R above, or, preferably, R$^c$ is hydrogen, $(C_1-C_4)$-alkyl, which is unsubstituted or substituted by one or more radicals selected from the group consisting of halogen, hydroxyl, $(C_1-C_4)$-alkoxy and $(C_1-C_4)$-alkylthio, or $(C_1-C_4)$-alkanoyl, $(C_1-C_4)$-haloalkanoyl, [$(C_1-C_4)$-alkoxy]carbonyl, [$(C_1-C_4)$-halo-alkoxy]carbonyl, $(C_1-C_4)$-alkylsulfinyl and $(C_1-C_4)$-alkylsulfonyl or in particular hydrogen or $(C_1-C_4)$-alkyl.

Examples of such radicals are:

$R^1$=aminocarbonyl, N-methylaminocarbonyl, N-ethylaminocarbonyl, N-(n-propyl)-aminocarbonyl, N-isopropylaminocarbonyl, N-butylaminocarbonyl, N-(2-hydroxyethyl)aminocarbonyl, N-cyclopropylaminocarbonyl, N-acetylaminocarbonyl, N-propionylaminocarbonyl, N,N-dimethylaminocarbonyl, N,N-diethylaminocarbonyl, N-ethyl-N-methylaminocarbonyl, N-acetyl-N-methylaminocarbonyl.

Preferably, $R^1$ is a radical of the formula —CO—R in which

R is hydrogen, $(C_1-C_8)$alkyl, $(C_2-C_8)$alkenyl, $(C_2-C_8)$alkynyl, $(C_3-C_6)$cycloalkyl, $(C_3-C_6)$cycloalkyl-$(C_1-C_4)$alkyl, phenyl, phenyl-$(C_1-C_4)$alkyl, heterocyclyl or heterocyclyl-$(C_1-C_4)$alkyl, where each of the 9 last-mentioned radicals is unsubstituted or substituted by one or more radicals selected from the group consisting of halogen, hydroxy, $(C_1-C_4)$ alkoxy, $(C_1-C_4)$haloalkoxy, $(C_1-C_4)$alkylthio, $(C_1-C_4)$ alkylsulfinyl, $(C_1-C_4)$alkylsulfonyl, mono$(C_1-C_4)$alkylamino, di$(C_1-C_4)$alkylamino, $(C_1-C_4)$alkanoyl, $(C_1-C_4)$haloalkanoyl, $[(C_1-C_4)$alkoxy]carbonyl and, in the case of cyclic radicals, also $(C_1-C_4)$alkyl and $(C_1-C_4)$haloalkyl, and in particular R is hydrogen, $(C_1-C_6)$alkyl, $(C_2-C_8)$alkenyl, $(C_2-C_8)$alkynyl, $(C_3-C_6)$cycloalkyl, or $(C_3-C_6)$cycloalkyl-$(C_1-C_4)$alkyl, where each of the 5 last-mentioned radicals is unsubstituted or substituted by one or more radicals selected from the group consisting of halogen, hydroxyl, $(C_1-C_4)$alkoxy, $(C_1-C_4)$alkylthio and, in the case of cyclic radicals, also $(C_1-C_4)$alkyl.

Very particularly, $R^1$ is a radical of the formula

—CHO or

—C(=NR$^a$)—H or

—CO—R or

—C(=NR$^a$)—R, in which

R is $(C_1-C_4)$alkyl which is unsubstituted or substituted by one or more radicals selected from the group consisting of halogen, hydroxyl, $(C_1-C_4)$alkoxy and $(C_1-C_4)$alkylthio, and $R^a$ is hydrogen, or independently, as defined for the radical R above or, preferably, $(C_1-C_4)$alkanoyl, $(C_1-C_4)$haloalkanoyl, $[(C_1-C_4)$alkoxy]carbonyl, $[(C_1-C_4)$haloalkoxy]carbonyl, phenylcarbonyl, phenoxycarbonyl, [phenyl-$(C_1-C_4)$alkyl]carbonyl, [phenyl-$(C_1-C_4)$alkoxy]carbonyl, aminocarbonyl, mono$[(C_1-C_4)$alkylamino]carbonyl, di$[(C_1-C_4)$alkylamino]carbonyl, $(C_1-C_4)$alkylsulfinyl, $(C_1-C_4)$alkylsulfonyl, $(C_1-C_4)$haloalkylsulfinyl or $(C_1-C_4)$haloalkylsulfonyl.

Examples of such radicals are:

$R^1$=formyl, acetyl, trifluoroacetyl, propionyl, 1-oxobutyl, iminomethyl, 1-iminoethyl, 1-iminopropyl, N-methyliminomethyl, N,N-dimethyliminomethyl, N-ethyliminomethyl, N,N-diethyliminomethyl, N-methyl-1-iminoethyl, N,N-dimethyl-1-iminoethyl, acetiminomethyl, 1-acetiminoethyl, 1-acetiminopropyl, (2-hydroxyethoxy)acetiminomethyl, N-acetyliminomethyl, N-acetyl-N-methyliminomethyl, N-acetyl-N-ethyliminomethyl.

Of particular interest is also the use according to the invention of compounds of the formula (I) or salts thereof in which $R^2$, $R^3$ in each case independently of one another and, in the case that n=2, 3, 4, 5 or 6, independently of the other radicals $R^2$ and $R^3$ are each hydrogen, $(C_1-C_2)$alkyl, $(C_1-C_2)$alkoxy or $(C_1-C_3)$alkanoyloxy, where the alkyl moiety of each of the 3 last-mentioned radicals is unsubstituted or substituted by one or more radicals selected from the group consisting of halogen, hydroxyl, $(C_1-C_6)$alkoxy and $(C_1-C_6)$haloalkoxy, preferably hydrogen, methyl or ethyl, in particular hydrogen, and n is 1, 2, 3, 4, 5 or 6, preferably 1, 2 or 3, in particular 1 or 2, very particularly 1.

Of particular interest is also the use according to the invention of compounds of the formula (I) or salts thereof in which $(R^4)_m$ are m radicals $R^4$, where each of the radicals $R^4$ independently of the others is selected from the group consisting of the radicals halogen, SCN, CN and $(C_1-C_{18})$alkyl, $(C_2-C_{18})$alkenyl, $(C_2-C_{18})$alkynyl, $(C_3-C_9)$cycloalkyl, $(C_5-C_9)$cycloalkenyl, $(C_3-C_9)$cycloalkyl-$(C_1-C_{12})$alkyl, phenyl, phenyl-$(C_1-C_{12})$alkyl, heterocyclyl and heterocyclyl-$(C_1-C_{12})$alkyl, where each of the 10 last-mentioned radicals is unsubstituted or substituted by one or more radicals selected from the group consisting of halogen, hydroxyl, amino, cyano, nitro, thiocyanato, $(C_1-C_4)$alkoxy, $(C_1-C_4)$haloalkoxy, $(C_2-C_4)$alkenyloxy, $(C_2-C_4)$haloalkenyloxy, $(C_1-C_4)$alkylthio, $(C_1-C_4)$alkylsulfinyl, $(C_1-C_4)$alkylsulfonyl, $(C_1-C_4)$haloalkylsulfinyl, $(C_1-C_4)$haloalkylsulfonyl, mono$(C_1-C_4)$alkylamino, di$(C_1-C_4)$alkylamino, $(C_1-C_4)$alkanoyl, $(C_1-C_4)$haloalkanoyl, $[(C_1-C_4)$alkoxy]carbonyl, $[(C_1-C_4)$haloalkoxy]carbonyl, aminocarbonyl, mono$[(C_1-C_4)$alkylamino]carbonyl, di$[(C_1-C_4)$alkylamino]carbonyl and, in the case of cyclic radicals, also $(C_1-C_4)$alkyl and $(C_1-C_4)$haloalkyl, and radicals of the formula —Z*-A, where Z* is a group of the formula O or S(O)$_x$, where x=0, 1 or 2, and A is hydrogen or $(C_1-C_{18})$alkyl, $(C_2-C_{18})$alkenyl, $(C_2-C_{18})$alkynyl, $(C_3-C_9)$cycloalkyl, $(C_5-C_9)$cycloalkenyl, $(C_3-C_9)$cycloalkyl-$(C_1-C_{12})$alkyl, phenyl, phenyl-$(C_1-C_{12})$alkyl, heterocyclyl or heterocyclyl-$(C_1-C_{12})$alkyl, or preferably $(C_1-C_{12})$alkyl, $(C_2-C_{12})$alkenyl, $(C_2-C_{12})$alkynyl, $(C_3-C_6)$cycloalkyl, $(C_5-C_6)$cycloalkenyl, $(C_3-C_6)$cycloalkyl-$(C_1-C_6)$alkyl, phenyl, phenyl-$(C_1-C_6)$alkyl, heterocyclyl or heterocyclyl-$(C_1-C_6)$alkyl, where each of the 20 last-mentioned radicals is unsubstituted or substituted by one or more radicals selected from the group consisting of halogen, hydroxyl, amino, cyano, nitro, thiocyanato, $(C_1-C_4)$alkoxy, $(C_1-C_4)$haloalkoxy, $(C_2-C_4)$alkenyloxy, $(C_2-C_4)$haloalkenyloxy, $(C_1-C_4)$alkylthio, $(C_1-C_4)$alkylsulfinyl, $(C_1-C_4)$alkylsulfonyl, $(C_1-C_4)$haloalkylsulfinyl, $(C_1-C_4)$haloalkylsulfonyl, mono$(C_1-C_4)$alkylamino, di$(C_1-C_4)$alkylamino, $(C_1-C_4)$alkanoyl, $(C_1-C_4)$haloalkanoyl, $[(C_1-C_4)$alkoxy]carbonyl, $[(C_1-C_4)$haloalkoxy]carbonyl, aminocarbonyl, mono$[(C_1-C_4)$alkylamino]carbonyl, di$[(C_1-C_4)$alkylamino]carbonyl and, in the case of cyclic radicals, also $(C_1-C_4)$alkyl and $(C_1-C_4)$haloalkyl, or an acyl radical, provided that Z*, in the case A=acyl, can only be O or S, preferably an acyl radical selected from the group consisting of the radicals $(C_1-C_6)$alkanoyl, $(C_1-C_4)$haloalkanoyl, $[(C_1-C_4)$alkoxy]carbonyl, $[(C_1-C_4)$haloalkoxy]carbonyl, phenylcarbonyl, phenoxycarbonyl, [phenyl-$(C_1-C_4)$alkyl]carbonyl, [phenyl-$(C_1-C_4)$alkoxy]carbonyl, where the phenyl ring of each of the 4 last-mentioned radicals is unsubstituted or substituted, aminocarbonyl, mono$[(C_1-C_4)$alkylamino]carbonyl, di$[(C_1-C_4)$alkylamino]carbonyl, $(C_1-C_4)$alkylsulfinyl, $(C_1-C_4)$alkylsulfonyl, $(C_1-C_4)$haloalkylsulfinyl and $(C_1-C_4)$haloalkylsulfonyl, where each radical $R^4$, including substituents, has 1 to 30 carbon atoms, preferably 1 to 20 carbon atoms, in particular 1 to 16 carbon atoms, and m is the integer 0, 1, 2, 3, 4 or 5, preferably 0, 1, 2, 3 or 4, in particular 0, 1, 2 or 3, very particularly 1 or 2.

Preference is given to the use according to the invention of compounds of the formula (I) or salts thereof in which $(R^4)_m$ are m radicals $R^4$, where each of the radicals $R^4$ independently of the others is selected from the group consisting of the radicals halogen, SCN, CN and $(C_1-C_6)$alkyl, $(C_2-C_6)$alkenyl, $(C_2-C_6)$alkynyl, $(C_3-C_6)$cycloalkyl, $(C_3-$ $C_6$)cycloalkyl-($C_1$-$C_4$)alkyl, phenyl, phenyl-($C_1$-$C_4$)alkyl, heterocyclyl and heterocyclyl-($C_1$-$C_4$)alkyl, and preferably ($C_1$-$C_4$)alkyl, ($C_2$-$C_4$)alkenyl, ($C_2$-$C_4$)alkynyl, ($C_3$-$C_6$)cycloalkyl, ($C_3$-$C_6$)cycloalkyl-($C_1$-$C_2$)alkyl, phenyl, phenyl-($C_1$-$C_2$)alkyl, heterocyclyl and heterocyclyl-($C_1$-$C_2$)alkyl, where each of the 18 last-mentioned radicals is unsubstituted or substituted by one or more radicals selected from the group consisting of halogen, hydroxyl, amino, cyano, nitro, ($C_1$-$C_4$)alkoxy, ($C_1$-$C_4$)haloalkoxy, ($C_2$-$C_4$)alkenyloxy, ($C_2$-$C_4$)haloalkenyloxy, ($C_1$-$C_4$)alkylthio, ($C_1$-$C_4$)alkylsulfinyl, ($C_1$-$C_4$)alkylsulfonyl, ($C_1$-$C_4$)haloalkylsulfinyl, ($C_1$-$C_4$)haloalkylsulfonyl, mono($C_1$-$C_4$)alkylamino, di($C_1$-$C_4$)alkylamino, ($C_1$-$C_4$)alkanoyl, ($C_1$-$C_4$)haloalkanoyl, [($C_1$-$C_4$)alkoxy]carbonyl, [($C_1$-$C_4$)haloalkoxy]carbonyl, aminocarbonyl, mono[($C_1$-$C_4$)alkylamino]carbonyl, di[($C_1$-$C_4$)alkylamino]carbonyl and, in the case of cyclic radicals, also ($C_1$-$C_4$)alkyl and ($C_1$-$C_4$)haloalkyl, and radicals of the formula —Z*-A, where Z* is a group of the formula O or $S(O)_x$, where x=0, 1 or 2, and A is hydrogen or ($C_1$-$C_8$)alkyl, ($C_2$-$C_8$)alkenyl, ($C_2$-$C_8$)alkynyl, ($C_3$-$C_6$)cycloalkyl, ($C_5$-$C_6$)cycloalkenyl, ($C_3$-$C_6$)cycloalkyl-($C_1$-$C_6$)alkyl, phenyl, phenyl-($C_1$-$C_6$)alkyl, heterocyclyl or heterocyclyl-($C_1$-$C_6$)alkyl, or preferably ($C_1$-$C_4$)alkyl, ($C_2$-$C_4$)alkenyl, ($C_2$-$C_4$)alkynyl, ($C_3$-$C_4$)cycloalkyl, ($C_3$-$C_6$)cycloalkyl-($C_1$-$C_4$)alkyl, phenyl, phenyl-($C_1$-$C_4$)alkyl, heterocyclyl or heterocyclyl-($C_1$-$C_4$)alkyl, where each of the 19 last-mentioned radicals is unsubstituted or substituted by one or more radicals selected from the group consisting of halogen, hydroxyl, amino, cyano, nitro, thiocyanato, ($C_1$-$C_4$)alkoxy, ($C_1$-$C_4$)haloalkoxy, ($C_2$-$C_4$)alkenyloxy, ($C_2$-$C_4$)haloalkenyloxy, ($C_1$-$C_4$)alkylthio, ($C_1$-$C_4$)alkylsulfinyl, ($C_1$-$C_4$)alkylsulfonyl, ($C_1$-$C_4$)haloalkylsulfinyl, ($C_1$-$C_4$)haloalkylsulfonyl, mono($C_1$-$C_4$)alkylamino, di($C_1$-$C_4$)alkylamino, ($C_1$-$C_4$)alkanoyl, ($C_1$-$C_4$)haloalkanoyl, [($C_1$-$C_4$)alkoxy]carbonyl, [($C_1$-$C_4$)haloalkoxy]carbonyl, aminocarbonyl, mono[($C_1$-$C_4$)alkylamino]carbonyl, di[($C_1$-$C_4$)alkylamino]carbonyl and, in the case of cyclic radicals, also ($C_1$-$C_4$)alkyl and ($C_1$-$C_4$)haloalkyl, or an acyl radical, provided that Z*, in the case that A=acyl can only be O or S, preferably an acyl radical selected from the group consisting of the radicals ($C_1$-$C_4$)alkanoyl, ($C_1$-$C_4$)haloalkanoyl, [($C_1$-$C_4$)alkoxy]carbonyl, [($C_1$-$C_4$)haloalkoxy]carbonyl, phenylcarbonyl, phenoxycarbonyl, [phenyl-($C_1$-$C_4$)alkyl]carbonyl, [phenyl-($C_1$-$C_4$)alkoxy]carbonyl, where the phenyl ring of each of the 4 last-mentioned radicals is unsubstituted or substituted by one or more radicals selected from the group consisting of halogen, ($C_1$-$C_4$)alkyl, ($C_1$-$C_4$)alkoxy, ($C_1$-$C_4$)haloalkyl, ($C_1$-$C_4$)haloalkoxy and ($C_1$-$C_4$)alkylthio, and m is the integer 0, 1, 2, 3, 4 or 5, preferably 0, 1, 2, 3 or 4, in particular 0, 1, 2 or 3, very particularly 1 or 2.

Here, heterocyclyl is preferably an aliphatic or aromatic heterocycle having a total of 1 to 3 heterocyclic ring atoms from the group consisting of N, O and S and a total of 5 or 6 ring atoms which is unsubstituted or substituted by one or more radicals selected from the group consisting of halogen, hydroxyl, amino, ($C_1$-$C_4$)alkyl, ($C_1$-$C_4$)alkoxy, ($C_1$-$C_4$)haloalkyl, ($C_1$-$C_4$)haloalkoxy, ($C_1$-$C_4$)alkylthio and oxo.

Preference is furthermore given to the use according to the invention of compounds of the formula (I) or salts thereof in which $(R^4)_m$ are m radicals $R^4$, where each of the radicals $R^4$ independently of the others is selected from the group consisting of the radicals halogen, SCN, CN and ($C_1$-$C_4$)alkyl, ($C_2$-$C_4$)alkenyl, ($C_2$-$C_4$)alkynyl and ($C_3$-$C_6$)cycloalkyl, where each of the 4 last-mentioned radicals is unsubstituted or substituted by one or more radicals selected from the group consisting of halogen, hydroxyl, ($C_1$-$C_4$)alkoxy, ($C_1$-$C_4$)haloalkoxy, ($C_1$-$C_4$)alkylthio, ($C_1$-$C_4$)alkylsulfinyl, ($C_1$-$C_4$)alkylsulfonyl, ($C_1$-$C_4$)alkanoyl, ($C_1$-$C_4$)haloalkanoyl, [($C_1$-$C_4$)alkoxy]carbonyl and, in the case of cyclic radicals, also ($C_1$-$C_4$)alkyl and ($C_1$-$C_4$)haloalkyl, and radicals of the formula —Z*-A, where Z* is a group of the formula O or $S(O)_x$, where x=0, 1 or 2, and A is hydrogen or ($C_1$-$C_4$)alkyl, ($C_2$-$C_4$)alkenyl, ($C_2$-$C_4$)alkynyl, ($C_3$-$C_6$)cycloalkyl where each of the 4 last-mentioned radicals is unsubstituted or substituted by one or more radicals selected from the group consisting of halogen, hydroxyl, ($C_1$-$C_4$)alkoxy, ($C_1$-$C_4$)haloalkoxy, ($C_1$-$C_4$)alkylthio, ($C_1$-$C_4$)alkylsulfinyl, ($C_1$-$C_4$)alkylsulfonyl, ($C_1$-$C_4$)alkanoyl, ($C_1$-$C_4$)haloalkanoyl, [($C_1$-$C_4$)alkoxy]carbonyl and, in the case of cyclic radicals, also ($C_1$-$C_4$)alkyl and ($C_1$-$C_4$)haloalkyl, or an acyl radical, provided that Z*, in the case that A=acyl, can only be O or S, preferably an acyl radical selected from the group consisting of the radicals ($C_1$-$C_4$)alkanoyl, ($C_1$-$C_4$)haloalkanoyl, [($C_1$-$C_4$)alkoxy]carbonyl, [($C_1$-$C_4$)haloalkoxy]carbonyl.

Particular preference is given to the use according to the invention of compounds of the formula (I) or salts thereof in which $(R^4)_m$ are m radicals $R^4$, where each of the radicals $R^4$ independently of the others is selected from the group consisting of the radicals halogen, such as F, Cl, Br and I, and SCN, CN and ($C_1$-$C_4$)alkyl, ($C_2$-$C_4$)alkenyl, ($C_2$-$C_4$)alkynyl and ($C_3$-$C_6$)cycloalkyl, where each of the 4 last-mentioned radicals is unsubstituted or substituted by one or more radicals selected from the group consisting of halogen, hydroxyl, ($C_1$-$C_4$)alkoxy, ($C_1$-$C_4$)haloalkoxy, ($C_1$-$C_4$)alkylthio, and, in the case of cyclic radicals, also ($C_1$-$C_4$)alkyl and ($C_1$-$C_4$)haloalkyl, and radicals of the formula —Z*-A, where Z* is a group of the formula O or $S(O)_x$, where x=0, 1 or 2, and A is hydrogen or ($C_1$-$C_4$)alkyl, ($C_2$-$C_4$)alkenyl, ($C_2$-$C_4$)alkynyl, ($C_3$-$C_6$)cycloalkyl where each of the 4 last-mentioned radicals is unsubstituted or substituted by one or more radicals selected from the group consisting of halogen, hydroxyl, ($C_1$-$C_4$)alkoxy, ($C_1$-$C_4$)haloalkoxy, ($C_1$-$C_4$)alkylthio and, in the case of cyclic radicals, also ($C_1$-$C_4$)alkyl and ($C_1$-$C_4$)haloalkyl, or an acyl radical, provided that Z*, in the case that A=acyl, can only be O or S, preferably an acyl radical selected from the group consisting of the radicals $(C_1-C_4)$alkanoyl, $(C_1-C_4)$haloalkanoyl, $[(C_1-C_4)$alkoxy]carbonyl, $[(C_1-C_4)$haloalkoxy]carbonyl.

Here, the group A-Z*— is especially preferably a hydroxyl group or an acyloxy group, for example acetyloxy or propionyloxy.

Particular preference is given to the use according to the invention of compounds of the formula (I) in which m is 0, 1, 2, 3 or 4, preferably 0, 1 or 2, in particular 1.

Of particular interest here are compounds of the formulae (I-1) or salts thereof

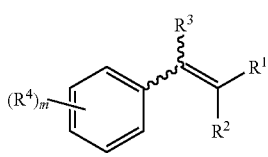
(I-1)

in which $R^1$, $R^2$, $R^3$, $R^4$ and m are as defined in formula (I). The compounds (I-1) can be present as Z and E isomers with respect to the double bonds (=compounds (I-1a) and (I-1b)), which are in most cases in a steady state with one another, the respective E isomer or the isomer (I-1a) generally being the more stable isomer:

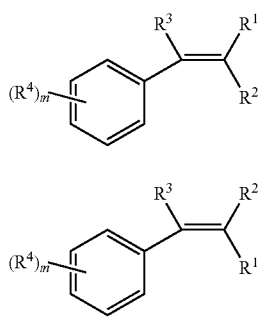
(I-1a)

(I-1b)

Of particular interest are the compounds of the formulae (I-2), (I-3), (I-4), (I-5) or else the further substituted compounds of the formulae (I-6), (I-7), (I-8), (I-9), (I-10) and (I-11):

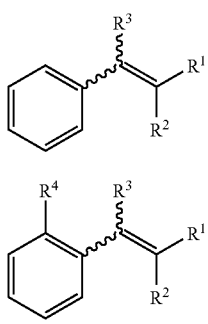
(I-2)

(I-3)

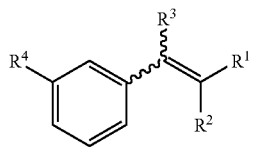
(I-4)

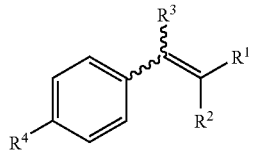
(I-5)

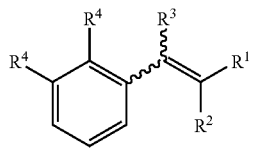
(I-6)

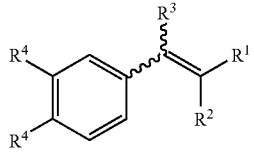
(I-7)

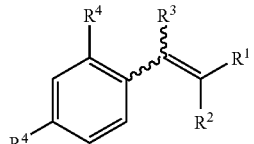
(I-8)

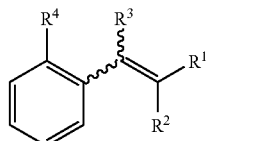
(I-9)

(I-10)

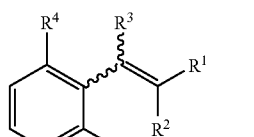
(I-11)

where in the formulae (I-2) to (I-11) $R^1$, $R^2$, $R^3$, $R^4$ and m are each as defined for formula (I) and where the radicals $R^4$ are defined independently of one another, i.e. are identical or different radicals.

Preference is given to the use according to the invention of the compounds of the formulae, (I-2) to (I-10), preferably of the formulae (I-3), (I-4), (I-5) and also (I-6) to (I-11) or salts thereof, where each of the radicals $R^4$ independently of the others is selected from the group consisting of the radicals halogen and $(C_1-C_4)$alkyl, which is unsubstituted or substituted by one or more radicals selected from the group consisting of halogen, hydroxyl, $(C_1-C_4)$alkoxy, $(C_1-C_4)$haloalkoxy, and radicals of the formula —Z*-A, where Z* is a group of the formula O or S and A is hydrogen or $(C_1-C_4)$alkyl, $(C_2-C_4)$alkenyl, $(C_2-C_4)$alkynyl, $(C_3-C_6)$cycloalkyl where each of the 4 last-mentioned radicals is unsubstituted or substituted by one or more radicals selected from the group consisting of halogen, hydroxyl, $(C_1-C_4)$alkoxy, $(C_1-C_4)$haloalkoxy, $(C_1-C_4)$alkylthio, $(C_1-C_4)$alkylsulfinyl, $(C_1-C_4)$alkylsulfonyl, $(C_1-C_4)$alkanoyl, $(C_1-C_4)$haloalkanoyl, $[(C_1-C_4)$alkoxy]carbonyl and, in the case of cyclic radicals, also $(C_1-C_4)$alkyl and $(C_1-C_4)$haloalkyl, or an acyl radical, preferably an acyl radical selected from the group consisting of the radicals $(C_1-C_4)$alkanoyl, $(C_1-C_4)$haloalkanoyl, $[(C_1-C_4)$alkoxy]carbonyl, $[(C_1-C_4)$haloalkoxy]carbonyl.

Particular preference is given to the use according to the invention of compounds of the formulae (I-1) to (I-11), preferably of the formulae (I-2), (I-3), (I-4) and (I-5) or salts thereof, where each of the radicals $R^4$ independently of the others is selected from the group consisting of the radicals halogen, methyl, ethyl, n-propyl, isopropyl, hydroxymethyl, methoxymethyl, dimethoxymethyl, hydroxyl, methoxy, ethoxy, acetoxy, propionyloxy, trifluoroacetoxy, preferably in combination with the preferred radicals and meanings for $R^1$, $R^2$ and $R^3$.

Examples of compounds to be used according to the invention are listed in the tables below.

Some of the compounds of the formula (I) are known or can be prepared analogously to known processes. Their use as safeners in plants in accordance with the use according to the invention has hitherto not been known.

Some compounds of the formula (I) or salts thereof (hereinbelow together referred to as "compounds (I) according to the invention" or "compounds (I)" or "safeners") are novel and also form part of the subject matter of the invention.

The compounds of the formula (I) can be prepared analogously to known processes described for preparing cinnamic acids and derivatives thereof. The acid derivatives, such as aldehydes and ketones, are likewise obtained by or analogously to known processes (see reference books and handbooks of preparative organic chemistry, for example Houben Weyl, Organic Synthesis, and the literature cited therein).

The invention also provides the method for protecting crop plants or useful plants against phytotoxic actions of agrochemicals, such as pesticides or fertilizers, or against environmental factors which cause damage to plants, which method comprises using compounds of the formula (I) or salts thereof as safeners, preferably by applying an effective amount of the compounds of the formula (I) or their salts to the plants, to parts of plants or seeds or seed thereof.

The safeners, together with agrochemical active compounds (pesticides or fertilizers), preferably pesticides are suitable for the selective control of harmful organisms in a number of plant crops, for example in crops of economic importance, such as cereals (wheat, barley, rye, triticale, rice, corn, millet), sugar beet, sugar cane, oilseed rape, cotton and soybeans. Of particular interest is the use in monocotyledonous crops, such as cereals (wheat, barley, rye, triticale, sorghum), including corn and rice, and monocotyledonous vegetable crops, but also in dicotyledonous crops, such as, for example, soybean, oilseed rape, cotton, grape vines, vegetable plants, fruit plants and ornamental plants. Also of interest are mutant crops which are partially tolerant to pesticides or transgenic crops which are partially tolerant, for example corn crops resistant to glufosinate or glyphosate; or soybean crops resistant to herbicidal imidazolinones. However, the particular advantage of the novel use of the safeners is their effective action in crops which are normally not tolerant to the pesticides mentioned.

For the joint use with agrochemicals/pesticides, the compounds of the formula (I) according to the invention can be applied simultaneously with the active compounds or in any order, and they are then capable of reducing or completely eliminating harmful side effects of these active compounds in crop plants, without negatively affecting or substantially reducing the activity of these active compounds against unwanted harmful organisms. Here, even damage caused by using a plurality of pesticides, for example a plurality of herbicides, insecticides or fungicides, or herbicides in combination with insecticides or fungicides, can be reduced substantially or eliminated completely. In this manner, it is possible to extend the field of use of conventional pesticides considerably.

If the compositions according to the invention comprise pesticides, these compositions are, after appropriate dilution, applied either directly to the area under cultivation, to the already germinated harmful and/or useful plants or to the already emerged harmful and/or useful plants. If the compositions according to the invention do not comprise any pesticide, these compositions can be employed by the tank mix method—i.e. the user mixes and dilutes the separately available products (the pesticide and the agent protecting the useful plants) immediately prior to application to the area to be treated—or prior to the application of a pesticide, or after the application of a pesticide, or for the pretreatment of seed, i.e., for example, for dressing the seed of the useful plants.

The advantageous actions of the compounds: (I) according to the invention are observed when they are used together with the pesticides by the pre-emergence method or the post-emergence method, for example in the case of simultaneous application as a tank mix or a coformulation or in the case of a separate application, in parallel or in succession (split application). It is also possible to repeat the application a number of times. In some cases, it may be expedient to combine a pre-emergence application with a post-emergence application. In most cases, one option is a post-emergence application to the useful plant or crop plant together with a simultaneous or later application of the pesticide. Also possible is the use of the compounds (I) according to the invention for seed dressing, for (dip) treatment of seedlings or for the treatment of other propagation material (for example potato tubers).

When using the compounds (I) according to the invention in combination with pesticides, for example herbicides, in addition to the safener action, enhanced action, for example herbicidal action, against harmful plants is frequently also observed. Furthermore, in many cases, there is an improved growth of the useful plants and crop plants, and it is possible to increase the harvest yields. Some of the last-mentioned advantageous actions are also observed when the compounds (I) are used without additional pesticides, in particular when other environmental factors negatively affect plant growth.

The compositions according to the invention may comprise one or more pesticides. Suitable pesticides are, for example, herbicides, insecticides, fungicides, acaricides and nematicides, which, when used on their own, would cause phytotoxic damage to the crop plants or would probably cause damage. Of particular interest are corresponding pesticidally active compounds from the groups of the herbicides, insecticides, acaricides, nematicides and fungicides, in particular herbicides.

The weight ratio of safener to pesticide can be varied within wide limits and is generally in the range from 1:100 to 100:1, preferably from 1:20 to 20:1, in particular from 1:10 to 10:1. The optimum weight ratio of safener to pesticide depends both on the respective safener used and the respective pesticide, and on the type of useful plant or crop plant to be protected. The required application rate of safener can, depending on the pesticide used and the type of useful plant to be protected, be varied within wide limits and is generally in the range from 0.001 to 10 kg, preferably from 0.005 to 5 kg, in particular from 0.1 to 1 kg, of safener per hectare.

For seed dressing, for example, from 0.005 to 20 g of safener per kilogram of seed, preferably from 0.01 to 10 g of safener per kilogram of seed, in particular from 0.05 to 5 g of safener per kilogram of seed, are used.

If solutions of safener are used for seed dressing and the seed or seedlings are wetted with the solutions, the suitable concentration is generally in the range from 1 to 10 000 ppm, preferably from 100 to 1000 ppm, based on the weight. The amounts and weight ratios required for a successful treatment can be determined by simple preliminary experiments.

The safeners can be formulated in the customary manner, separately or together with the agrochemicals, for example pesticides or fertilizers. Accordingly, the present invention also provides the useful-plant-protecting or crop-plant-protecting compositions.

Herbicides whose phytotoxic side effects on crop plants can be reduced using compounds of the formula (I) can be from entirely different structural classes and have entirely different mechanisms of action. Preference is given to commercially available herbicides as described, for example, in the handbook "The Pesticide Manual", 13th Edition 2003, The British Crop Protection Council, and the e-Pesticide Manual Version 3 (2003), or else trade names and common names which are referred to in the "Compendium of Pesticide Common Names" (searchable via the Internet) and in literature quoted therein. The herbicides and plant growth regulators mentioned hereinbelow by way of example are in each case referred to by their standardized common active compound name according to the "International Organization for Standardization" (ISO), or by the chemical name or the code number. Examples of active compounds whose phytotoxic action in crop plants and useful plants can be reduced by the compounds (I) according to the invention are: acetochlor; acifluorfen(-sodium); aclonifen; AKH 7088, i.e. [[[1-[5-[2-chloro-4-(trifluoromethyl)phenoxy]-2-nitrophenyl]-2-methoxyethylidene]amino]oxy]acetic acid and its methyl ester; alachlor; alloxydim(-sodium); ametryn; amicarbazone, amidochlor, amidosulfuron; aminopyralid, amitrol; AMS, i.e. ammonium sulfamate; anilofos; asulam; atrazine; azafenidin; azimsulfuron (DPX-A8947); aziprotryn; barban; BAS 516 H, i.e. 5-fluoro-2-phenyl-4H-3,1-benzoxazin-4-one; beflubutamid; benazolin(-ethyl); benfluralin; benfuresate; bensulfuron(-methyl); bensulide; bentazone(-sodium); benzfendizone, benzobicyclone; benzofenap; benzofluor; benzoylprop(-ethyl); benzthiazuron; bialaphos (bilanafos); bifenox; bispyribac-(-sodium); bromacil; bromobutide; bromofenoxim; bromoxynil; bromuron; buminafos; busoxinone; butachlor; butafenacil; butamifos; butenachlor; buthidazole; butralin; butroxydim; butylate; cafenstrole (CH-900); carbetamide; carfentrazone(-ethyl); caloxydim, CDAA, i.e. 2-chloro-N,N-di-2-propenylacetamide; CDEC, i.e. 2-chloroallyl diethyldithiocarbamate; chlomethoxyfen; chloramben; chlorazifop-butyl; chlorbromuron; chlorbufam; chlorfenac; chlorfenprop, chlorflurenol-methyl; chloridazon; chlorimuron(-ethyl); chlornitrofen; chlorotoluron; chloroxuron; chlorpropham; chlorsulfuron; chlorthal-dimethyl; chlorthiamid; chlortoluron, cinidon-(-methyl or -ethyl), cinmethylin; cinosulfuron; clethodim; clefoxydim, clodinafop and its ester derivatives (for example clodinafop-propargyl); clomazone; clomeprop; cloprop, cloproxydim; clopyralid; clopyrasulfuron(-methyl); cloransulam(-methyl); cumyluron (JC 940); cyanazine; cycloate; cyclosulfamuron (AC 104); cycloxydim; cycluron; cyhalofop and its ester derivatives (for example butyl ester, DEH-112); cyperquat; cyprazine; cyprazole; daimuron; 2,4-D; 2,4-DB; dalapon; dazomet, desmedipham; desmetryn; di-allate; dicamba; dichlobenil; dichlorprop(-P); diclofop and its esters such as diclofop-methyl; diclosulam, diethatyl(-ethyl); difenoxuron; difenzoquat; diflufenican; diflufenzopyr; dimefuron; dimepiperate; dimethachlor; dimethametryn; dimethenamid (SAN-582H); dimethenamid(-P); dimethazone, dimethipin; dimexyflam, dimetrasulfuron, dinitramine; dinoseb; dinoterb; diphenamid; dipropetryn; diquat; dithiopyr; diuron; DNOC; eglinazine-ethyl; EL 77, i.e. 5-cyano-1-(1,1-dimethylethyl)-N-methyl-1H-pyrazole-4-carboxamide; endothal; epoprodan, EPTC; esprocarb; ethalfluralin; ethametsulfuron-methyl; ethidimuron; ethiozin; ethofumesate; ethoxyfen and its esters (for example ethyl ester, HC-252), ethoxysulfuron, etobenzanid (HW 52); F5231, i.e. N-[2-chloro-4-fluoro-5-[4-(3-fluoropropyl)-4,5-dihydro-5-oxo-1H-tetrazol-1-yl]-phenyl] ethanesulfonamide; fenoprop; fenoxan, fenoxaprop and fenoxaprop-P and their esters, for example fenoxaprop-P-ethyl and fenoxaprop-ethyl; fenoxydim; fentrazamide; fenuron; flamprop(-methyl or -isopropyl or -isopropyl-L); flazasulfuron; florasulam; fluazifop and fluazifop-P and their esters, for example fluazifop-butyl and fluazifop-P-butyl; fluazolate, flucarbazone(-sodium); flucetosulfuron, fluchloralin; flufenacet (FOE 5043), flufenpyr, flumetsulam; flumeturon; flumiclorac(-pentyl); flumioxazin (S-482); flumipropyn; fluometuron; fluorochloridone, fluorodifen; fluoroglycofen(-ethyl); flupoxam (KNW-739); flupropacil (UBIC-4243); fluproanate, flupyrsulfuron(-methyl, or -sodium); flurenol(-butyl); fluridone; flurochloridone; fluroxypyr(-meptyl); flurprimidol, flurtamone; fluthiacet(-methyl); fluthiamide (also known as flufenacet); fomesafen; foramsulfuron; fosamine; furilazole (MON 13900), furyloxyfen; glufosinate (-ammonium); glyphosate(-isopropylammonium); halosafen; halosulfuron(-methyl) and its esters (for example the methyl ester, NC-319); haloxyfop and its esters; haloxyfop-P (=R-haloxyfop) and its esters; HC-252 (diphenylether), hexazinone; imazamethabenz(-methyl); imazamethapyr; imazamox; imazapic, imazapyr; imazaquin and salts such as the ammonium salts; imazethamethapyr; imazethapyr, imazosulfuron; indanofan; iodosulfuron-(methyl)-(sodium), ioxynil; isocarbamid; isopropalin; isoproturon; isouron; isoxaben; isoxachlortole; isoxaflutole; isoxapyrifop; karbutilate; lactofen; lenacil; linuron; MCPA; MCPA-thioethyl, MCPB; mecoprop(-P); mefenacet; mefluidid; mesosulfuron(-methyl); mesotrione; metam, metamifop, metamitron; metazachlor; methabenzthiazuron; methazole; methoxyphenone; methyidymron; metobenzuron, metobromuron; (S-)metolachlor; metosulam (XRD 511); metoxuron; metribuzin; metsulfuron-methyl; MK-616; molinate; monalide; monocarbamide dihydrogensulfate; monolinuron; monuron; MT 128, i.e. 6-chloro-N-(3-chloro-2-propenyl)-5-methyl-N-phenyl-3-pyridazinamine; MT 5950, i.e. N-[3-chloro-4-(1-methylethyl)-phenyl]-2-methylpentanamide; napronilide; napropamide; naptalam; NC 310, i.e. 4-(2,4-dichlorobenzoyl)-1-methyl-5-benzyloxypyrazole; neburon;

nicosulfuron; nipyraclophen; nitralin; nitrofen; nitrofluorfen; norflurazon; orbencarb; oryzalin; oxadiargyl (RP-020630); oxadiazone; oxasulfuron; oxaziclomefone; oxyfluorfen; paraquat; pebulate; pelargonic acid; pendimethalin; penoxulam; pentanochlor, pentoxazone; perfluidone; pethoxamid, phenisopham; phenmedipham; picloram; picolinafen; piperophos; piributicarb; pirifenop-butyl; pretilachlor; primisulfuron(-methyl); procarbazone(-sodium); procyazine; prodiamine; profluazole, profluralin; proglinazine(-ethyl); prometon; prometryn; propachlor; propanil; propaquizafop; propazine; propham; propisochlor; propoxycarbazone-(-sodium), propyzamide; prosulfalin; prosulfocarb; prosulfuron (CGA-152005); prynachlor; pyraclonil, pyraflufen(-ethyl); pyrazolinate; pyrazon; pyrazosulfuron-(-ethyl); pyrazoxyfen; pyribenzoxim; pyributicarb; pyridafol; pyridate; pyriftalid, pyrimidobac(-methyl); pyrithiobac(-sodium) (KIH-2031); pyroxofop and its esters (for example propargyl ester); quinclorac; quinmerac; quinoclamine, quinofop and its ester derivatives, quizalofop and quizalofop-P and their ester derivatives, for example quizalofop-ethyl; quizalofop-P-tefuryl and -ethyl; renriduron; rimsulfuron (DPX-E 9636); S 275, i.e. 2-[4-chloro-2-fluoro-5-(2-propynyloxy)phenyl]-4,5,6,7-tetrahydro-2H-indazole; secbumeton; sethoxydim; siduron; simazine; simetryn; SN 106279, i.e. 2-[[7-[2-chloro-4-(trifluoromethyl)phenoxy]-2-naphthalenyl]oxy]propanoic acid and its methyl ester; sulcotrione; sulfentrazone (FMC-97285, F-6285); sulfazuron; sulfometuron(-methyl); sulfosate (ICI-A0224); sulfosulfuron; TCA; tebutam (GCP-5544); tebuthiuron; tepraloxydim; terbacil; terbucarb; terbuchlor; terbumeton; terbuthylazine; terbutryn; TFH 450, i.e. N,N-diethyl-3-[(2-ethyl-6-methylphenyl)sulfonyl]-1H-1,2,4-triazole-1-carboxamide; thenylchlor (NSK-850); thiafluamide; thiazafluron; thiazopyr (Mon-13200); thidiazimin (SN-24085); thidiazuron, thifensulfuron(-methyl); thiobencarb; tiocarbazil; tralkoxydim; tri-allate; triasulfuron; triaziflam; triazofenamide; tribenuron(-methyl); 2,3,6-trichlorobenzoic acid (2,3,6-TBA), triclopyr; tridiphane; trietazine; trifloxysulfuron(-sodium), trifluralin; triflusulfuron and esters (e.g. methyl ester, DPX-66037); trimeturon; tritosulfuron; tsitodef; vernolate; WL 110547, i.e. 5-phenoxy-1-[3-(trifluoromethyl)phenyl]-1H-tetrazole; UBH-509; D-489; LS 82-556; KPP-300; NC-324; NC-330; KH-218; DPX-N8189; SC-0774; DOWCO-535; DK-8910; V-53482; PP-600; MBH-001; KIH-9201; ET-751; KIH-6127; KIH-2023 and KIH5996.

Herbicides, whose phytotoxic side effects on crop plants can be reduced using compounds of the formula I are, for example, herbicides from the group of the carbamates, thiocarbamates, haloacetanilides, substituted phenoxy-, naphthoxy- and phenoxyphenoxycarboxylic acid derivatives and heteroaryloxyphenoxyalkanecarboxylic acid derivatives, such as quinolyloxy-, quinoxalyloxy-, pyridyloxy-, benzoxazolyloxy- and benzothiazolyloxyphenoxyalkanecarboxylic acid esters, cyclohexanedione oximes, benzoylcyclohexanediones, benzoylisoxazoles, benzoylpyrazoles, imidazolinones, pyrimidinyloxypyridinecarboxylic acid derivatives, pyrimidyloxybenzoic acid derivatives, sulfonylureas, sulfonylaminocarbonyltriazolinones, triazolopyrimidinesulfonamide derivatives, phosphinic acid derivatives and salts thereof, glycine derivatives, triazolinones, triazinones and also S—(N-aryl-N-alkylcarbamoylmethyl)dithiophosphoric esters, pyridinecarboxylic acids, pyridines, pyridinecarboxamides, 1,3,5-triazines and others.

Preference is given to phenoxyphenoxy- and heteroaryloxyphenoxycarboxylic acid esters and salts, cyclohexanedione oximes, benzoylcyclohexanediones, benzoylisoxazoles, sulfonylureas, sulfonylaminocarbonyltriazolinones, imidazolinones and mixtures of the active compounds mentioned with one another and/or with active compounds used for broadening the activity spectrum of the herbicides, for example bentazone, cyanazine, atrazine, bromoxynil, dicamba and other leaf-acting herbicides.

Herbicides which are suitable for combination with the safeners according to the invention are, for example:

A) herbicides of the type of the phenoxyphenoxy- and heteroaryloxyphenoxycarboxylic acid derivatives, such as A1) phenoxyphenoxy- and benzyloxyphenoxycarboxylic acid derivatives, for example methyl 2-(4-(2,4-dichlorophenoxy)phenoxy)propionate (diclofop-methyl),
methyl 2-(4-(4-bromo-2-chlorophenoxy)phenoxy)propionate (DE-A 26 01 548),
methyl 2-(4-(4-bromo-2-fluorophenoxy)phenoxy)propionate (U.S. Pat. No. 4,808,750),
methyl 2-(4-(2-chloro-4-trifluoromethylphenoxy)phenoxy) propionate (DE-A 24-33 067),
methyl 2-(4-(2-fluoro-4-trifluoromethylphenoxy)phenoxy) propionate (U.S. Pat. No. 4,808,750),
methyl 2-(4-(2,4-dichlorobenzyl)phenoxy)propionate (DE-A 24 17 487),
ethyl 4-(4-(4-trifluoromethylphenoxy)phenoxy)pent-2-enoate,
methyl 2-(4-(4-trifluoromethylphenoxy)phenoxy)propionate (DE-A 24 33 067),
butyl (R)-2-[4-(4-cyano-2-fluorophenoxy)phenoxy]propionate (cyhalofop-butyl)

A2) "monocyclic" heteroaryloxyphenoxyalkanecarboxylic acid derivatives, for example
ethyl 2-(4-(3,5-dichloropyridyl-2-oxy)phenoxy)propionate (EP-A 0 002 925),
propargyl 2-(4-(3,5-dichloropyridyl-2-oxy)phenoxy)propionate (EP-A 0 003 114),
methyl (RS)- or (R)-2-(4-(3-chloro-5-trifluoromethyl-2-pyridyloxy)phenoxy)propionate (haloxyfop-methyl or haloxyfop-P-methyl),
ethyl 2-(4-(3-chloro-5-trifluoromethyl-2-pyridyloxy)phenoxy)propionate (EP-A 0 003 890),
propargyl 2-(4-(5-chloro-3-fluoro-2-pyridyloxy)phenoxy) propionate (clodinafop-propargyl),
butyl (RS)- or (R)-2-(4-(5-trifluoromethyl-2-pyridyloxy) phenoxy)propionate (fluazifop-butyl or fluazifop-P-butyl),
(R)-2-[4-(3-chloro-5-trifluoromethyl-2-pyridyloxy)phenoxy]propionic acid A3) "bicyclic" heteroaryloxyphenoxyalkanecarboxylic acid derivatives, for example
methyl and ethyl (RS)- or (R)-2-(4-(6-chloro-2-quinoxalyloxy)phenoxy)propionate (quizalofop-methyl and -ethyl or quizalofop-P-methyl and -P-ethyl),
methyl 2-(4-(6-fluoro-2-quinoxalyloxy)phenoxy)propionate (see J. Pest. Sci. Vol. 10, 61 (1985)),
2-isopropylidenaminooxyethyl (R)-2-(4-(6-chloro-2-quinoxalyloxy)phenoxy)-propionate (propaquizafop),
ethyl (RS)- or (R)-2-(4-(6-chlorobenzoxazol-2-yloxy)phenoxy)propionate (fenoxaprop-ethyl or fenoxaprop-P-ethyl),
ethyl 2-(4-(6-chlorobenzthiazol-2-yloxy)phenoxy)propionate (DE-A-26 40 730),
tetrahydro-2-furylmethyl (RS)- or (R)-2-(4-(6-chloroquinoxalyloxy)phenoxy)-propionate (EP-A-0 323 727);

B) herbicides from the group of the sulfonylureas, such as pyrimidinyl- or triazinylaminocarbonyl[benzene-, -pyridine-, -pyrazole-, -thiophene- and -(alkyl-sulfonyl)alkylamino]sulfamides. Preferred substituents on the pyrimidine ring or the triazine ring are alkoxy, alkyl, haloalkoxy, haloalkyl, halogen or dimethylamino, it being possible to combine all substituents independently of one another. Preferred substituents in the benzene, pyridine, pyrazole, thiophene or (alkylsulfonyl)alkylamino moiety are alkyl, alkoxy, halogen, nitro, alkoxycarbonyl, aminocarbonyl, alkylaminocarbonyl, dialkylaminocarbonyl, alkoxyaminocarbonyl, haloalkoxy, haloalkyl, alkylcarbonyl, alkoxyalkyl, (alkanesulfonyl)alkylamino. Such suitable sulfonylureas are, for example, B1) phenyl- and benzylsulfonylureas and related compounds, for example
1-(2-chlorophenylsulfonyl)-3-(4-methoxy-6-methyl-1,3,5-triazin-2-yl)urea (chlorsulfuron),
1-(2-ethoxycarbonylphenylsulfonyl)-3-(4-chloro-6-methoxypyrimidin-2-yl)urea (chlorimuron-ethyl),
1-(2-methoxyphenylsulfonyl)-3-(4-methoxy-6-methyl-1,3,5-triazin-2-yl)urea (metsulfuron-methyl),
1-(2-chloroethoxyphenylsulfonyl)-3-(4-methoxy-6-methyl-1,3,5-triazin-2-yl)urea (Triasulfuron),
1-(2-methoxycarbonylphenylsulfonyl)-3-(4,6-dimethylpyrimidin-2-yl)urea (sulfumeturon-methyl),
1-(2-methoxycarbonylphenylsulfonyl)-3-(4-methoxy-6-methyl-1,3,5-triazin-2-yl)-3-methylurea (tribenuron-methyl),
1-(2-methoxycarbonylbenzylsulfonyl)-3-(4,6-dimethoxypyrimidin-2-yl)urea (bensulfuron-methyl),
1-(2-methoxycarbonylphenylsulfonyl)-3-(4,6-bis-(difluoromethoxy)pyrimidin-2-yl)urea (primisulfuron-methyl),
3-(4-ethyl-6-methoxy-1,3,5-triazin-2-yl)-1-(2,3-dihydro-1,1-dioxo-2-methylbenzo[b]-thiophene-7-sulfonyl)urea -(EP-A 0-796 83),
3-(4-ethoxy-6-ethyl-1,3,5-triazin-2-yl)-1-(2,3-dihydro-1,1-dioxo-2-methylbenzo[b]-thiophene-7-sulfonyl)urea (EP-A 0 079 683),
3-(4-methoxy-6-methyl-1,3,5-triazin-2-yl)-1-(2-methoxycarbonyl-5-iodophenyl-sulfonyl)urea (WO 92/13845),
methyl 2-[4-dimethylamino-6-(2,2,2-trifluoroethoxy)-1,3,5-triazin-2-ylcarbamoyl-sulfamoyl]-3-methylbenzoate (DPX-66037, triflusulfuron-methyl),
oxetan-3-yl 2-[(4,6-dimethylpyrimidin-2-yl)carbamoylsulfamoyl]benzoate (CGA-277476, oxasulfuron),
methyl 4-iodo-2-[3-(4-methoxy-6-methyl-1,3,5-triazin-2-yl)ureidosulfonyl]benzoate, sodium salt (iodosulfuron-methyl-sodium),
methyl 2-[3-(4,6-dimethoxypyrimidin-2-yl)ureidosulfonyl]-4-methanesulfonylamino-methylbenzoate (mesosulfuron-methyl, WO 95/10507),
N,N-dimethyl-2-[3-(4,6-dimethoxypyrimidin-2-yl)ureidosulfonyl]-4-formylamino-benzamide (foramsulfuron, WO 95/01344),
1-(4,6-dimethoxy-1,3,5-triazin-2-yl)-3-[2-(2-methoxyethoxy)phenylsulfonyl]urea (cinosulfuron),
methyl 2-[(4-ethoxy-6-methylamino-1,3,5-triazin-2-yl)carbamoylsulfamoyl]benzoate (ethametsulfuron-methyl),
1-(4-methoxy-6-methyl-1,3,5-triazin-2-yl)-3-[2-(3,3,3-trifluoropropyl)phenylsulfonyl]-urea (prosulfuron),
methyl 2-(4,6-dimethylpyrimidin-2-ylcarbamoylsulfamoyl)benzoate (sulfometuron-methyl),
1-(4-methoxy-6-trifluoromethyl-1,3,5-triazin-2-yl)-3-(2-trifluoromethyl-benzenesulfonyl)urea (tritosulfuron);

B2) thienylsulfonylureas, for example
1-(2-methoxycarbonylthiophen-3-yl)-3-(4-methoxy-6-methyl-1,3,5-triazin-2-yl)urea (thifensulfuron-methyl);

B3) pyrazolylsulfonylureas, for example
1-(4-ethoxycarbonyl-1-methylpyrazol-5-ylsulfonyl)-3-(4,6-dimethoxypyrimidin-2-yl)-urea (pyrazosulfuron-ethyl),
methyl 3-chloro-5-(4,6-dimethoxypyrimidin-2-ylcarbamoylsulfamoyl)-1-methyl-pyrazole-4-carboxylate (halosulfuron-methyl),
methyl 5-(4,6-dimethylpyrimidin-2-yl-carbamoylsulfamoyl)-1-(2-pyridyl)pyrazole-4-carboxylate (NC-330, see Brighton Crop Prot. Conference 'Weeds' 1991, Vol. 1, p. 45 ff.),
1-(4,6-dimethoxypyrimidin-2-yl)-3-[1-methyl-4-(2-methyl-2H-tetrazol-5-yl)pyrazol-5-yl-sulfonyl]urea (DPX-A8947, azimsulfuron);

B4) sulfonediamide derivatives, for example
3-(4,6-dimethoxypyrimidin-2-yl)-1-(N-methyl-N-methylsulfonylaminosulfonyl)urea (amidosulfuron) and its structural analogs (EP-A 0 131 258 and Z. Pfl. Krankh. Pfl. Schutz, special issue XII, 489-497 (1990));

B5) pyridylsulfonylureas, for example
1-(3-N,N-dimethylaminocarbonylpyridin-2-ylsulfonyl)-3-(4,6-dimethoxypyrimidin-2-yl)-urea (nicosulfuron),
1-(3-ethylsulfonylpyridin-2-ylsulfonyl)-3-(4,6-dimethoxypyrimidin-2-yl)urea (rimsulfuron),
methyl 2-[3-(4,6-dimethoxypyrimidin-2-yl)ureidosulfonyl]-6-trifluoromethyl-3-pyridine-carboxylate, sodium salt (DPX-KE 459, flupyrsulfuron-methyl-sodium),
3-(4,6-dimethoxypyrimidin-2-yl)-1-(3-N-methylsulfonyl-N-methylaminopyridin-2-yl)-sulfonylurea or its salts (DE-A 40 00 503 and DE-A 40 30 577),
1-(4,6-dimethoxypyrimidin-2-yl)-3-(3-trifluoromethyl-2-pyridylsulfony)urea (flazasulfuron),
1-(4,6-dimethoxypyrimidin-2-yl)-3-[3-(2,2,2-trifluoroethoxy)-2-pyridylsulfonyl]urea sodium salt (trifloxysulfuron-sodium);

B6) alkoxyphenoxysulfonylureas, for example
3-(4,6-dimethoxypyrimidin-2-yl)-1-(2-ethoxyphenoxy)sulfonylurea or its salts (ethoxysulfuron);

B7) imidazolylsulfonylureas, for example
1-(4,6-dimethoxypyrimidin-2-yl)-3-(2-ethylsulfonylimidazo[1,2-a]pyridin-3-yl)sulfonyl-urea (MON 37500, sulfosulfuron),
1-(2-chloroimidazo[1,2-a]pyridin-3-ylsulfonyl)-3-(4,6-dimethoxypyrimidin-2-yl)urea (imazosulfuron);

B8) phenylaminosulfonylureas, for example
1-[2-(cyclopropylcarbonyl)phenylaminosulfonyl]-3-(4,6-dimethoxypyrimidin-2-yl)urea (cyclosulfamuron);

C) chloroacetanilides, for example
acetochlor, alachlor, butachlor, dimethachlor, dimethenamid, metazachlor, metolachlor, S-metolachlor, pethoxamid, pretilachlor, propachlor, propisochlor and thenylchlor;

D) thiocarbamates, for example
S-ethyl N,N-dipropylthiocarbamate (EPTC),
S-ethyl N,N-diisobutylthiocarbamate (butylate);

cycloate, dimepiperate, esprocarb, molinate, orbencarb, pebulate, prosulfocarb, thiobencarb, tiocarbazil and tri-allate;

E) cyclohexanedione oximes, for example alloxydim, butroxydim, clethodim, cloproxydim, cycloxydim, protoxydim, sethoxydim, tepraloxydim and tralkoxydim;

F) imidazolinones, for example imazamethabenz-methyl, imazapic, imazamox, imazapyr, imazaquin and imazethapyr;

G) triazolopyrimidinesulfonamide derivatives, for example chloransulam-methyl, diclosulam, florasulam, flumetsulam, metosulam and penoxulam;

H) benzoylcyclohexanediones, for example
2-(2-chloro-4-methylsulfonylbenzoyl)cyclohexane-1,3-dione (SC-0051, sulcotrione),
2-(2-nitrobenzoyl)-4,4-dimethylcyclohexane-1,3-dione (EP-A 0 274 634),
2-(2-nitro-3-methylsulfonylbenzoyl)-4,4-dimethylcyclohexane-1,3-dione (WO 91/13548),
2-[4-(methylsulfonyl)-2-nitrobenzoyl]-1,3-cyclohexanedione (mesotrione);

I) benzoylisoxazoles, for example
5-cyclopropyl-[2-(methylsulfonyl)-4-(trifluoromethyl)benzoyl]isoxazole (isoxaflutole);

J) benzoylpyrazoles, for example
2-[4-(2,4-dichloro-m-toluyl)-1,3-dimethylpyrazol-5-yloxy] 4'-methylacetophenone (benzofenap),
4-(2,4-dichlorobenzoyl)-1,3-dimethylpyrazol-5-yl toluene-4-sulfonate (pyrazolynate),
2-[4-(2,4-dichlorobenzoyl)-1,3-dimethylpyrazol-5-yloxy] acetophenone (pyrazoxyfen);

K) sulfonylaminocarbonyltriazolinones, for example
4,5-dihydro-3-methoxy-4-methyl-5-oxo-N-(2-trifluoromethoxyphenylsulfonyl)-1H-1,2,4-triazole-1-carboxamide sodium salt (flucarbazone-sodium),
methyl 2-(4,5-dihydro-4-methyl-5-oxo-3-propoxy-1H-1,2,4-triazol-1-yl)carboxamido-sulfonylbenzoate sodium salt (propoxycarbazone-Na);

L) triazolinones, for example
4-amino-N-tert-butyl 4,5-dihydro-3-isopropyl-5-oxo-1,2,4-1H-triazole-1-carboxamide (amicarbazone),
2-(2,4-dichloro-5-prop-2-ynyloxyphenyl)-5,6,7,8-tetrahydro-1,2,4-triazolo[4,3-a]-pyridin-3(2H)-one (azafenidin),
ethyl (RS)-2-chloro-3-[2-chloro-5-(4-difluoromethyl-4,5-dihydro-3-methyl-5-oxo-1H-1,2,4-triazol-1-yl)-4-fluorophenyl]propionate (carfentrazone-ethyl),
2',4'-dichloro-5'-(4-difluoromethyl-4,5-dihydro-3-methyl-5-oxo-1H-1,2,4-triazol-1-yl)-methanesulfonanilide (sulfentrazone);

M) phosphinic acids and derivatives, for example
4-[hydroxy(methyl)phosphinoyl]-L-homoalanyl-L-alanyl-L-alanine (bilanafos), DL-homoalanin-4-yl(methyl)phosphinic acid ammonium salt (glufosinate-ammonium);

N) glycine derivatives, for example
N-(phosphonomethyl)glycine and its salts (glyphosate and salts, for example the sodium salt or the isopropylammonium salt),
N-(phosphonomethyl)glycine trimesium salt (sulfosate);

O) pyrimidinyloxypyridinecarboxylic acid derivatives and pyrimidinyloxybenzoic acid derivatives, for example
benzyl 3-(4,6-dimethoxypyrimidin-2-yl)oxypyridine-2-carboxylate (EP-A 0 249 707), methyl 3-(4,6-dimethoxypyrimidin-2-yl)oxypyridine-2-carboxylate (EP-A 0 249 707),
1-(ethoxycarbonyloxyethyl) 2,6-bis[(4,6-dimethoxypyrimidin-2-yl)oxy]benzoate (EP-A 0 472 113),
2,6-bis[(4,6-dimethoxypyrimidin-2-yl)oxy]benzoic acid (bispyribac-sodium),
pyribenzoxim, pyriftalid, pyriminobac-methyl and pyrithiobac-sodium;

P) S—(N-aryl-N-alkylcarbamoylmethyl)dithiophosphonic acid esters, such as
S—[N-(4-chlorophenyl)-N-isopropylcarbamoylmethyl]O, O-dimethyl dithiophosphate (anilophos);

Q) triazinones, for example
3-cyclohexyl-6-dimethylamino-1-methyl-1,3,5-triazine-2,4-(1H,3H)-dione (hexazinone),
4-amino-4,5-dihydro-3-methyl-6-phenyl-1,2,4-triazin-5-one (metamitron),
4-amino-6-tert-butyl-4,5-dihydro-3-methylthio-1,2,4-triazin-5-one (metribuzin);

R) pyridinecarboxylic acids, for example clopyralid, fluroxypyr, picloram and triclopyr;

S) pyridines, for example dithiopyr and thiazopyr;

T) pyridinecarboxamides, for example diflufenican and picolinafen;

U) 1,3,5-triazines, for example ametryn, atrazine, cyanazine, dimethametrin, prometon, prometryn, propazine, simazine, symetryn, terbumeton, terbuthylazine, terbutryn and trietazine;

V) plant growth regulators, for example forchlorfenuron and thidiazuron.

The herbicides of groups A to V are known, for example, from the respective abovementioned publications and from "The Pesticide Manual", The British Crop Protection Council, 13th Edition, 2003, or the e-Pesticide Manual, Version 3.0, British Crop Protection Council 2003.

Fungicidally active compounds which can be used in combination with the crop-plant-protecting compounds (I) according to the invention are preferably commercially available active compounds, for example (the compounds are, analogous to the herbicides, generally referred to by their common names): 2-phenylphenol; 8-hydroxyquinoline sulfate; acibenzolar-S-methyl; actinovate; aldimorph; amidoflumet; ampropylfos; ampropylfos-potassium; andoprim; anilazine; azaconazole; azoxystrobin; benalaxyl; benodanil; benomyl; benthiavalicarbisopropyl; benzamacril; benzamacril-isobutyl; binapacryl; biphenyl; bitertanol; blasticidin-S; boscalid; bromuconazole; bupirimate; buthiobate; butylamine; calcium polysulfide; capsimycin; captafol; captan; carbendazim; carboxin; carpropamid; carvone; chinomethionat; chlobenthiazone; chlorfenazole; chloroneb; chlorothalonil; chlozolinate; cis-1-(4-chlorophenyl)-2-(1H-1,2,4-triazol-1-yl)-cycloheptanol; clozylacon; cyazofamid; cyflufenamid; cymoxanil; cyproconazole; cyprodinil; cyprofuram; Dagger G; debacarb; dichlofluanid; dichlone; dichlorophen; diclocymet; diclomezine; dicloran; diethofencarb; difenoconazole; diflumetorim; dimethirimol; dimethomorph; dimoxystrobin; diniconazole; diniconazole-M; dinocap; diphenylamine; dipyrithione; ditalimfos; dithianon; dodine; drazoxolon; edifenphos; epoxiconazole; ethaboxam; ethirimol; etridiazole; famoxadone; fenamidone; fenapanil; fenarimol; fenbuconazole; fenfuram; fenhexamid, fenitropan; fenoxanil; fenpiclonil; fenpropidin; fenpropimorph; ferbam; fluazinam; flubenzimine; fludioxonil; flumetover; flumorph; fluoromide; fluoxastrobin; fluquinconazole; flurprimidol; flusilazole; flusulfamide; flutolanil; flutriafol; folpet; fosetyl-Al; fosetyl-sodium; fuberidazole; furalaxyl; furametpyr; furcarbanil; furmecyclox; guazatine; hexachlorobenzene; hexaconazole; hymexazol; imazalil; imibenconazole; iminoctadine triacetate; iminoctadine tris(albesilate); iodocarb; ipconazole; iprobenfos; iprodione; iprovalicarb; irumamycin; isoprothiolane; isovaledione; kasugamycin; kresoxim-methyl; mancozeb; maneb; meferimzone; mepanipyrim; mepronil; metalaxyl; metalaxyl-M; metconazole; methasulfocarb; methfuroxam; methyl 1-(2,3-dihydro-2,2-dimethyl-1H-inden-1-yl)-1H-imidazole-5-carboxylate; methyl 2-[[[cyclopropyl[(4-methoxyphenyl)imino]methyl]thio]methyl]-.alpha.-(methoxymethylene)benzeneacetate; methyl 2-[2-[3-(4-chlorophenyl)-1-methyl-allylideneaminooxymethyl]phenyl]-3-methoxyacrylate; metiram; metominostrobin; metrafenone; metsulfovax; mildiomycin; monopotassium carbonate; myclobutanil; myclozolin; N-(3-ethyl-3,5,5-trimethylcyclohexyl)-3-formylamino-2-hydroxy-benzamide; N-(6-methoxy-3-pyridinyl)cyclopropanecarboxamide; N-butyl-8-(1,1-dimethylethyl)-1-oxaspiro[4.5]decan-3-amine; natamycin; nitrothal-isopropyl; noviflumuron; nuarimol; ofurace; orysastrobin; oxadixyl; oxolinic acid; oxpoconazole; oxycarboxin; oxyfenthiin; paclobutrazol; pefurazoate; penconazole; pencycuron; penthiopyrad; phosdiphen; phthalide; picobenzamid; picoxystrobin; piperalin; polyoxins; polyoxorim; probenazole; prochloraz; procymidone; propamocarb; propanosine-sodium; propiconazole; propineb; proquinazid; prothioconazole; pyraclostrobin; pyrazophos; pyrifenox; pyrimethanil; pyroquilon; pyroxyfur; pyrrolnitrin; quinconazole; quinoxyfen; quintozene; silthiofam; simeconazole; sodium tetrathiocarbonate; spiroxamine; sulfur; tebuconazole; tecloftalam; tecnazene; tetcyclacis; tetraconazole; thiabendazole; thicyofen; thifluzamide; thiophanatemethyl; thiram; tiadinil; tioxymid; tolclofos-methyl; tolylfluanid; triadimefon; triadimenol; triazbutil; triazoxide; tricyclamide; tricyclazole; tridemorph; trifloxystrobin; triflumizole; triforine; triticonazole; uniconazole; validamycin A; vinclozolin; zineb; ziram; zoxamide; (2S)—N-[2-[4-[[3-(4-chlorophenyl)-2-propynyl]oxy]-3-methoxyphenyl]ethyl]-3-methyl-2-[(methylsulfonyl)amino]-butanamide; 1-(1-naphthalenyl)-1H-pyrrole-2,5-dione; 2,3,5,6-tetrachloro-4-(methylsulfonyl)pyridine; 2,4-dihydro-5-methoxy-2-methyl-4-[[[[1-[3-(trifluoromethyl)-phenyl]ethylidene]amino]oxy]methyl]phenyl]-3H-1,2,3-triazol-3-one; 2-amino-4-methyl-N-phenyl-5-thiazolecarboxamide; 2-chloro-N-(2,3-dihydro-1,1,3-trimethyl-1H-inden-4-yl)-3-pyridinecarboxamide; 3,4,5-trichloro-2,6-pyridinedicarbonitrile; 3-[(3-bromo-6-fluoro-2-methyl-1H-indol-1-yl)sulfonyl]-N,N-dimethyl-1H-1,2,4-triazole-1-sulfonamide; copper salts and copper preparations, such as Bordeaux mixture; copper hydroxide; copper naphthenate; copper oxychloride; copper sulfate; cufraneb; copper (I) oxide; mancopper; oxine-copper.

Insecticidally and acaricidally active compounds are, for example (analogously to the herbicides and fungicides referred to, where possible, by their common names): alanycarb, aldicarb, aldoxycarb, allyxycarb, aminocarb, bendiocarb, benfuracarb, bufencarb, butacarb, butocarboxim, butoxycarboxim, carbaryl, carbofuran, carbosulfan, cloethocarb, dimetilan, ethiofencarb, fenobucarb, fenothiocarb, formetanate, furathiocarb, isoprocarb, metam-sodium, methiocarb, methomyl, metolcarb, oxamyl, pirimicarb, promecarb, propoxur, thiodicarb, thiofanox, trimethacarb, XMC, xylylcarb, acephate, azamethiphos, azinphos (-methyl, -ethyl), bromophos-ethyl, bromfenvinfos (-methyl), butathiofos, cadusafos, carbophenothion, chlorethoxyfos, chlorfenvinphos, chlormephos, chlorpyrifos (-methyl/-ethyl), coumaphos, cyanofenphos, cyanophos, chlorfenvinphos, demeton-S-methyl, demeton-S-methylsulfon, dialifos, diazinon, dichlofenthion, dichlorvos/DDVP, dicrotophos, dimethoate, dimethylvinphos, dioxabenzofos, disulfoton, EPN, ethion, ethoprophos, etrimfos, famphur, fenamiphos, fenitrothion, fensulfothion, fenthion, flupyrazofos, fonofos, formothion, fosmethilan, fosthiazate, heptenophos, iodofenphos, iprobenfos, isazofos, isofenphos, isopropyl O-salicylate, isoxathion, malathion, mecarbam, methacrifos, methamidophos, methidathion, mevinphos, monocrotophos, naled, omethoate, oxydemeton-methyl, parathion (-methyl/-ethyl), phenthoate, phorate, phosalone, phosmet, phosphamidon, phosphocarb, phoxim, pirimiphos (-methyl/-ethyl), profenofos, propaphos, propetamphos, prothiofos, prothoate, pyraclofos, pyridaphenthion, pyridathion, quinalphos, sebufos, sulfotep, sulprofos, tebupirimfos, temephos, terbufos, tetrachlorvinphos, thiometon, triazophos, triclorfon, vamidothion, acrinathrin, allethrin (d-cis-trans, d-trans), beta-cyfluthrin, bifenthrin, bioallethrin, bioallethrin-S-cyclopentylisomer, bioethanomethrin, biopermethrin, bioresmethrin, chlovaporthrin, cis-cypermethrin, cis-resmethrin, cis-permethrin, clocythrin, cyprothrin, cyfluthrin, cyhalothrin, cypermethrin (alpha-, beta-, theta-, zeta-), cyphenothrin, deltamethrin, empenthrin (1R-isomer), esfenvalerate, etofenprox, fenfluthrin, fenpropathrin, fenpyrithrin, fenvalerate, flubrocythrinate, flucythrinate, flufenprox, flumethrin, fluvalinate, fubfenprox, gamma-cyhalothrin, imiprothrin, kadethrin, lambda-cyhalothrin, metofluthrin, permethrin (cis-, trans-), phenothrin (1R-trans isomer), prallethrin, profluthrin, protrifenbute, pyresmethrin, resmethrin, RU 15525, silafluofen, taufluvalinate, tefluthrin, terallethrin, tetramethrin (-1R-isomer), tralomethrin, transfluthrin, ZXI 8901, pyrethrins (pyrethrum), DDT, indoxacarb, acetamiprid, clothianidin, dinotefuran, imidacloprid, nitenpyram, nithiazine, thiacloprid, thiamethoxam, nicotine, bensultap, cartap, camphechlor, chlordane, endosulfan, gamma-HCH, HCH, heptachlor, lindane, methoxychlor spinosad, acetoprole, ethiprole, fipronil, vaniliprole, avermectin, emamectin, emamectin-benzoate, ivermectin, milbemycin, diofenolan, epofenonane, fenoxycarb, hydroprene, kinoprene, methoprene, pyriproxifen, triprene, chromafenozide, halofenozide, methoxyfenozide, tebufenozide, bistrifluron, chlofluazuron, diflubenzuron, fluazuron, flucycloxuron, flufenoxuron, hexaflumuron, lufenuron, novaluron, noviflumuron, penfluron, teflubenzuron, triflumuron, buprofezin, cyromazine, diafenthiuron, azocyclotin, cyhexatin, fenbutatin-oxide, chlorfenapyr, binapacryl, dinobuton, dinocap, DNOC, fenazaquin, fenpyroximate, pyrimidifen, pyridaben, tebufenpyrad, tolfenpyrad, hydramethyinon, dicofol, rotenone, acequinocyl, fluacrypyrim, Bacillus thuringiensis strains, spirodiclofen, spiromesifen, 3-(2,5-dimethylphenyl)-8-methoxy-2-oxo-1-azaspiro[4.5]dec-3-en4-yl ethyl carbonate (alias: carbonic acid, 3-(2,5-dimethylphenyl)-8-methoxy-2-oxo-1-azaspiro[4.5]dec-3-en4-yl ethyl ester, CAS-Reg.-No.: 382608-10-8) and carbonic acid, cis-3-(2,5-dimethylphenyl)-8-methoxy-2-oxo-1-azaspiro[4.5]dec-3-en-4-yl ethyl ester (CAS-Reg.-No.: 203313-25-1), flonicamid, amitraz, propargite, N2-[1,1-dimethyl-2-(methylsulfonyl)ethyl]-3-iodo-N1-[2-methyl-4-[1,2,2,2-tetrafluoro-1-(trifluoromethyl)ethyl]phenyl]-1,2-benzenedicarboxamide (CAS-Reg.-No.: 272451-65-7), thiocyclam hydrogenoxalate, thiosultap-sodium, azadirachtin, *Bacillus* spec., *Beauveria* spec., codlemone, *Metarrhizium* spec., *Paecilomyces* spec., *thuringiensin, Verticillium* spec., aluminum phosphide, methyl bromide, sulfuryl fluoride, cryolite, flonicamid, pymetrozine, clofentezine, etoxazole, hexythiazox, amidoflumet, benclothiaz, benzoximate, bifenazate, bromopropylate, buprofezin, chinomethionat, chlordimeform, chlorobenzilate, chloropicrin, clothiazoben, cycloprene, dicyclanil, fenoxacrim, fentrifanil, flubenzimine, flufenerim, flutenzin, gossyplure, hydramethyinone, japonilure, metoxadiazone, petroleum, piperonyl butoxide, potassium oleate, pyridalyl, sulfluramid, tetradifon, tetrasul, triarathene, verbutin.

Insecticides which, on their own or together with herbicides, can cause damage to plants include, for example:

organophosphates, for example terbufos (Counter®), fonofos (Dyfonate®), phorate (Thimet®), chlorpyriphos (Reldan®), carbamates, such as carbofuran (Furadan®), pyrethroid insecticides, such as tefluthrin (Force®), deltamethrin (Decis®) and tralomethrin (Scout®), and other insecticidal agents having a different mechanism of action.

The compounds of the formula (I) and their combinations with one or more of the abovementioned pesticides can be formulated in various ways, depending on the prevailing physicochemical and biological parameters. Examples of suitable formulation types are:

emulsifiable concentrates which are prepared by dissolving the active compounds in an organic solvent, for example butanol, cyclohexanone, dimethylformamide, xylene or else relatively high-boiling hydrocarbons or mixtures of the organic solvents with addition of one or more ionic and/or nonionic surfactants (emulsifiers). Suitable emulsifiers are, for example, calcium alkylarylsulfonates, fatty acid polyglycol esters, alkyaryl polyglycol ethers, fatty alcohol polyglycol ethers, propylene oxide/ethylene oxide condensates, alkyl polyethers, sorbitan esters and polyoxyethylenesorbitan fatty acid esters;

dusts, which are obtained by grinding the active compounds with finely dispersed inorganic or organic solid substances, for example talc, natural clays, such as kaolin, bentonite and pyrophyllite, diatomaceous earth or meals;

water- or oil-based suspension concentrates, which can be prepared, for example, by wet grinding using bead mills;

water-soluble powders;

water-soluble concentrates;

granules, such as water-soluble granules, water-dispersible granules and granules for application by broadcasting and soil application;

wettable powders which, in addition to active compound, also contain diluents or inert substances and surfactants;

capsule suspensions and microcapsules;

ultra-low-volume formulations.

The abovementioned formulation types are known to the person skilled in the art and described, for example, in: K. Martens, "Spray Drying Handbook", 3rd Ed., G. Goodwin Ltd., London, 1979; W. van Valkenburg, "Pesticide Formulations", Marcel Dekker, N.Y. 1973; Winnaker-Küchler, "Chemische Technologie" [Chemical Technology], volume 7, C. Hanser Verlag Munich, 4th edition 1986; "Perry's Chemical Engineer's Handbook", 5th Ed., McGraw-Hill, N.Y. 1973, pages 8-57.

The formulation auxiliaries required, such as inert materials, surfactants, solvents and other additives are also known and are described, for example, in: McCutcheon's "Detergents and Emulsifiers Annual", MC Publ. Corp., Ridgewood N.J.; C. Marsden, "Solvents Guide", 2nd Ed., Interscience, N.Y. 1963; H. von Olphen, "Introduction to Clay Colloid Chemistry", 2nd Ed., J. Wiley & Sons, N.Y.; Schönfeldt, "Grenzflätchenaktive Äthylenoxidaddukte" [Surface-active ethylene oxide adducts], Wiss. Verlagsgesellschaft, Stuttgart 1976; Sisley and Wood, "Encyclopedia of Surface Active Agents", Chem. Publ. Co. Inc., N.Y. 1964; Watkins, "Handbook of Insecticide Dust Diluents and Carriers", 2nd Ed., Darland Books, Caldwell N.J.; Winnacker-Küchler, "Chemische Technologie", volume 7, C. Hanser Verlag Munich, 4th edition 1986.

In addition to the abovementioned formulation auxiliaries, the useful-plant-protecting compositions may comprise, if appropriate, customary tackifiers, wetting agents, dispersants, penetrants, emulsifiers, preservatives, antifreeze agents, fillers, carriers, colorants, anti-foams, evaporation inhibitors and pH or viscosity regulators.

Depending on the formulation type, the useful-plant-protecting compositions generally comprise 0.1 to 99% by weight, in particular 0.2 to 95% by weight, of one or more safeners of the formula I or a combination of safener and pesticide. Furthermore, they comprise 1 to 99.9, in particular 4 to 99.5, % by weight of one or more solid or liquid additives and 0 to 25, in particular 0.1 to 25, % by weight of a surfactant. In emulsifiable concentrates, the concentration of active compound, i.e. the concentration of safener and/or pesticide, is generally 1 to 90, in particular 5 to 80, % by weight. Dusts usually comprise 1 to 30, preferably 5 to 20, % by weight of active compound. In wettable powders, the concentration of active compound is generally 10 to 90% by weight. In water-dispersible granules, the content of active compound is, for example, between 1 and 95% by weight, preferably between 10 and 80% by weight.

For use, the formulations, which are present in commercially available form, are, if appropriate, diluted in a customary manner, for example in the case of wettable powders, emulsifiable concentrates, dispersions and water-dispersible granules, with water. Preparations in the form of dusts, granules and sprayable solutions are usually not diluted with any further inert substances prior to use. The required application rate of the safeners varies with the external conditions such as, inter alia, temperature, humidity and the type of herbicide used.

In the examples below, which illustrate the invention but do not limit it, the amounts are based on weight, unless defined otherwise.

A) CHEMICAL EXAMPLES

Examples of compounds of the formula (I) according to the invention are compiled in the table below; in table 1:

| | |
|---|---|
| Comp. = | Compound |
| c = | cyclo |
| i = | iso |
| n = | normal (straight-chain) |
| s = | secondary |
| t = | tertiary |
| Ac = | Acetyl |
| Bu = | n-Butyl |
| n-Bu = | n-Butyl |
| Et = | Ethyl |
| Me = | Methyl |
| n-Pr = | n-Propyl |
| i-Pr = | Isopropyl |
| c-Pr = | Cyclopropyl |

| | | |
|---|---|---|
| i-Pen = | Isopentyl | |
| R = | substituent in the 5- or 6-position on the phenyl ring | |
| R = | 5-Me means methyl in the 5-position on the phenyl ring (see numbering of the ring atoms in the formula (Ia)) | |
| R = | H = only hydrogen as substituents in positions 5 and 6 on phenyl | |

TABLE 1

Compounds of the formula (I)

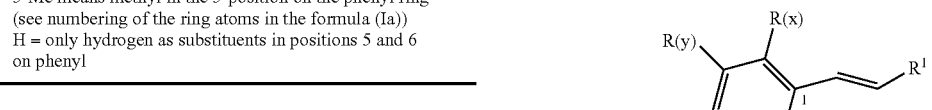

(Ia)

| Comp. No. | $R^1$ | R(x) | R(y) | R(z) | R | Physical data |
|---|---|---|---|---|---|---|
| 1 | CO—OH | H | H | H | H | |
| 2 | CO—OMe | H | H | H | H | |
| 3 | CO—OEt | H | H | H | H | |
| 4 | CO—O-n-Pr | H | H | H | H | |
| 5 | CO—O-n-Bu | H | H | H | H | |
| 6 | CO—O-c-Pr | H | H | H | H | |
| 7 | CO—O—CH$_2$CH$_2$OH | H | H | H | H | |
| 8 | CO—O—C$_{12}$H$_{25}$ | H | H | H | H | |
| 9 | CO—O—C$_{16}$H$_{33}$ | H | H | H | H | |
| 10 | CO—NH$_2$ | H | H | H | H | |
| 11 | CO—NHMe | H | H | H | H | |
| 12 | CO—NHEt | H | H | H | H | |
| 13 | CO—NH-n-Pr | H | H | H | H | |
| 14 | CO—NH-i-Pr | H | H | H | H | |
| 15 | CO—NH-c-Pr | H | H | H | H | |
| 16 | CO—NH-n-Pr | H | H | H | H | |
| 17 | CO—NH-n-Bu | H | H | H | H | |
| 18 | CO—NMe$_2$ | H | H | H | H | |
| 19 | CO—NEt$_2$ | H | H | H | H | |
| 20 | CO—NHNH$_2$ | H | H | H | H | |
| 21 | CN | H | H | H | H | |
| 22 | CHO | H | H | H | H | |
| 23 | CO—Me | H | H | H | H | |
| 24 | CO—Et | H | H | H | H | |
| 25 | CO—OH | Me | H | H | H | |
| 26 | CO—OMe | Me | H | H | H | |
| 27 | CO—OEt | Me | H | H | H | |
| 28 | CO—O-n-Pr | Me | H | H | H | |
| 29 | CO—O-n-Bu | Me | H | H | H | |
| 30 | CO—O-c-Pr | Me | H | H | H | |
| 31 | CO—O—CH$_2$CH$_2$OH | Me | H | H | H | |
| 32 | CO—O—C$_{12}$H$_{25}$ | Me | H | H | H | |
| 33 | CO—O—C$_{16}$H$_{33}$ | Me | H | H | H | |
| 34 | CO—NH$_2$ | Me | H | H | H | |
| 35 | CO—NHMe | Me | H | H | H | |
| 36 | CO—NHEt | Me | H | H | H | |
| 37 | CO—NH-n-Pr | Me | H | H | H | |
| 38 | CO—NH-i-Pr | Me | H | H | H | |
| 39 | CO—NH-c-Pr | Me | H | H | H | |
| 40 | CO—NH-n-Pr | Me | H | H | H | |
| 41 | CO—NH-n-Bu | Me | H | H | H | |
| 42 | CO—NMe$_2$ | Me | H | H | H | |
| 43 | CO—NEt$_2$ | Me | H | H | H | |
| 44 | CO—NHNH$_2$ | Me | H | H | H | |
| 45 | CN | Me | H | H | H | |
| 46 | CHO | Me | H | H | H | |
| 47 | CO—Me | Me | H | H | H | |
| 48 | CO—Et | Me | H | H | H | |
| 49 | CO—OH | OH | H | H | H | |
| 50 | CO—OMe | OH | H | H | H | |
| 51 | CO—OEt | OH | H | H | H | |
| 52 | CO—O-n-Pr | OH | H | H | H | |
| 53 | CO—O-n-Bu | OH | H | H | H | |
| 54 | CO—O-c-Pr | OH | H | H | H | |
| 55 | CO—O—CH$_2$CH$_2$OH | OH | H | H | H | |
| 56 | CO—O—C$_{12}$H$_{25}$ | OH | H | H | H | |
| 57 | CO—O—C$_{16}$H$_{33}$ | OH | H | H | H | |
| 58 | CO—NH$_2$ | OH | H | H | H | |
| 59 | CO—NHMe | OH | H | H | H | |
| 60 | CO—NHEt | OH | H | H | H | |
| 61 | CO—NH-n-Pr | OH | H | H | H | |
| 62 | CO—NH-i-Pr | OH | H | H | H | |
| 63 | CO—NH-c-Pr | OH | H | H | H | |
| 64 | CO—NH-n-Pr | OH | H | H | H | |
| 65 | CO—NH-n-Bu | OH | H | H | H | |
| 66 | CO—NMe$_2$ | OH | H | H | H | |
| 67 | CO—NEt$_2$ | OH | H | H | H | |
| 68 | CO—NHNH$_2$ | OH | H | H | H | |
| 69 | CN | OH | H | H | H | |
| 70 | CHO | OH | H | H | H | |
| 71 | CO—Me | OH | H | H | H | |
| 72 | CO—Et | OH | H | H | H | |
| 73 | CO—OH | OAc | H | H | H | |
| 74 | CO—OMe | OAc | H | H | H | |
| 75 | CO—OEt | OAc | H | H | H | |
| 76 | CO—O-n-Pr | OAc | H | H | H | |
| 77 | CO—O-n-Bu | OAc | H | H | H | |
| 78 | CO—O-c-Pr | OAc | H | H | H | |
| 79 | CO—O—CH$_2$CH$_2$OH | OAc | H | H | H | |
| 80 | CO—O—C$_{12}$H$_{25}$ | OAc | H | H | H | |
| 81 | CO—O—C$_{16}$H$_{33}$ | OAc | H | H | H | |
| 82 | CO—NH$_2$ | OAc | H | H | H | |
| 83 | CO—NHMe | OAc | H | H | H | |
| 84 | CO—NHEt | OAc | H | H | H | |
| 85 | CO—NH-n-Pr | OAc | H | H | H | |
| 86 | CO—NH-i-Pr | OAc | H | H | H | |
| 87 | CO—NH-c-Pr | OAc | H | H | H | |
| 88 | CO—NH-n-Pr | OAc | H | H | H | |
| 89 | CO—NH-n-Bu | OAc | H | H | H | |
| 90 | CO—NMe$_2$ | OAc | H | H | H | |
| 91 | CO—NEt$_2$ | OAc | H | H | H | |
| 92 | CO—NHNH$_2$ | OAc | H | H | H | |
| 93 | CN | OAc | H | H | H | |
| 94 | CHO | OAc | H | H | H | |
| 95 | CO—Me | OAc | H | H | H | |
| 96 | CO—Et | OAc | H | H | H | |
| 97 | CO—OH | OMe | H | H | H | |
| 98 | CO—OMe | OMe | H | H | H | |
| 99 | CO—OEt | OMe | H | H | H | |
| 100 | CO—O-n-Pr | OMe | H | H | H | |
| 101 | CO—O-n-Bu | OMe | H | H | H | |
| 102 | CO—O-c-Pr | OMe | H | H | H | |
| 103 | CO—O—CH$_2$CH$_2$OH | OMe | H | H | H | |
| 104 | CO—O—C$_{12}$H$_{25}$ | OMe | H | H | H | |
| 105 | CO—O—C$_{16}$H$_{33}$ | OMe | H | H | H | |
| 106 | CO—NH$_2$ | OMe | H | H | H | |
| 107 | CO—NHMe | OMe | H | H | H | |
| 108 | CO—NHEt | OMe | H | H | H | |
| 109 | CO—NH-n-Pr | OMe | H | H | H | |
| 110 | CO—NH-i-Pr | OMe | H | H | H | |
| 111 | CO—NH-c-Pr | OMe | H | H | H | |
| 112 | CO—NH-n-Pr | OMe | H | H | H | |
| 113 | CO—NH-n-Bu | OMe | H | H | H | |
| 114 | CO—NMe$_2$ | OMe | H | H | H | |
| 115 | CO—NEt$_2$ | OMe | H | H | H | |
| 116 | CO—NHNH$_2$ | OMe | H | H | H | |
| 117 | CN | OMe | H | H | H | |
| 118 | CHO | OMe | H | H | H | |
| 119 | CO—Me | OMe | H | H | H | |

TABLE 1-continued

Compounds of the formula (I)

(Ia)

| Comp. No. | R¹ | R(x) | R(y) | R(z) | R | Physical data |
|---|---|---|---|---|---|---|
| 120 | CO—Et | OMe | H | H | H | |
| 121 | CO—OH | F | H | H | H | |
| 122 | CO—OMe | F | H | H | H | |
| 123 | CO—OEt | F | H | H | H | |
| 124 | CO—O-n-Pr | F | H | H | H | |
| 125 | CO—O-n-Bu | F | H | H | H | |
| 126 | CO—O-c-Pr | F | H | H | H | |
| 127 | CO—O—CH$_2$CH$_2$OH | F | H | H | H | |
| 128 | CO—O—C$_{12}$H$_{25}$ | F | H | H | H | |
| 129 | CO—O—C$_{16}$H$_{33}$ | F | H | H | H | |
| 130 | CO—NH$_2$ | F | H | H | H | |
| 131 | CO—NHMe | F | H | H | H | |
| 132 | CO—NHEt | F | H | H | H | |
| 133 | CO—NH-n-Pr | F | H | H | H | |
| 134 | CO—NH-i-Pr | F | H | H | H | |
| 135 | CO—NH-c-Pr | F | H | H | H | |
| 136 | CO—NH-n-Pr | F | H | H | H | |
| 137 | CO—NH-n-Bu | F | H | H | H | |
| 138 | CO—NMe$_2$ | F | H | H | H | |
| 139 | CO—NEt$_2$ | F | H | H | H | |
| 140 | CO—NHNH$_2$ | F | H | H | H | |
| 141 | CN | F | H | H | H | |
| 142 | CHO | F | H | H | H | |
| 143 | COMe | F | H | H | H | |
| 144 | CO—Et | F | H | H | H | |
| 145 | CO—OH | Cl | H | H | H | |
| 146 | CO—OMe | Cl | H | H | H | |
| 147 | CO—OEt | Cl | H | H | H | |
| 148 | CO—O-n-Pr | Cl | H | H | H | |
| 149 | CO—O-n-Bu | Cl | H | H | H | |
| 150 | CO—O-c-Pr | Cl | H | H | H | |
| 151 | CO—O—CH$_2$CH$_2$OH | Cl | H | H | H | |
| 152 | CO—O—C$_{12}$H$_{25}$ | Cl | H | H | H | |
| 153 | CO—O—C$_{16}$H$_{33}$ | Cl | H | H | H | |
| 154 | CO—NH$_2$ | Cl | H | H | H | |
| 155 | CO—NHMe | Cl | H | H | H | |
| 156 | CO—NHEt | Cl | H | H | H | |
| 157 | CO—NH-n-Pr | Cl | H | H | H | |
| 158 | CO—NH-i-Pr | Cl | H | H | H | |
| 159 | CO—NH-c-Pr | Cl | H | H | H | |
| 160 | CO—NH-n-Pr | Cl | H | H | H | |
| 161 | CO—NH-n-Bu | Cl | H | H | H | |
| 162 | CO—NMe$_2$ | Cl | H | H | H | |
| 163 | CO—NEt$_2$ | Cl | H | H | H | |
| 164 | CO—NHNH$_2$ | Cl | H | H | H | |
| 165 | CN | Cl | H | H | H | |
| 166 | CHO | Cl | H | H | H | |
| 167 | CO—Me | Cl | H | H | H | |
| 168 | CO—Et | Cl | H | H | H | |
| 169 | CO—OH | OEt | H | H | H | |
| 170 | CO—OMe | OEt | H | H | H | |
| 171 | CO—OEt | OEt | H | H | H | |
| 172 | CO—O-n-Pr | OEt | H | H | H | |
| 173 | CO—O-n-Bu | OEt | H | H | H | |
| 174 | CO—O-c-Pr | OEt | H | H | H | |
| 175 | CO—O—CH$_2$CH$_2$OH | OEt | H | H | H | |
| 176 | CO—O—C$_{12}$H$_{25}$ | OEt | H | H | H | |
| 177 | CO—O—C$_{16}$H$_{33}$ | OEt | H | H | H | |
| 178 | CO—NH$_2$ | OEt | H | H | H | |
| 179 | CO—NHMe | OEt | H | H | H | |
| 180 | CO—NHEt | OEt | H | H | H | |
| 181 | CO—NH-n-Pr | OEt | H | H | H | |
| 182 | CO—NH-i-Pr | OEt | H | H | H | |
| 183 | CO—NH-c-Pr | OEt | H | H | H | |
| 184 | CO—NH-n-Pr | OEt | H | H | H | |
| 185 | CO—NH-n-Bu | OEt | H | H | H | |
| 186 | CO—NMe$_2$ | OEt | H | H | H | |
| 187 | CO—NEt$_2$ | OEt | H | H | H | |
| 188 | CO—NHNH$_2$ | OEt | H | H | H | |
| 189 | CN | OEt | H | H | H | |
| 190 | CHO | OEt | H | H | H | |
| 191 | CO—Me | OEt | H | H | H | |
| 192 | CO—Et | OEt | H | H | H | |
| 193 | CO—OH | H | Me | H | H | |
| 194 | CO—OMe | H | Me | H | H | |
| 195 | CO—OEt | H | Me | H | H | |
| 196 | CO—O-n-Pr | H | Me | H | H | |
| 197 | CO—O-n-Bu | H | Me | H | H | |
| 198 | CO—O-c-Pr | H | Me | H | H | |
| 199 | CO—O—CH$_2$CH$_2$OH | H | Me | H | H | |
| 200 | CO—O—C$_{12}$H$_{25}$ | H | Me | H | H | |
| 201 | CO—O—C$_{16}$H$_{33}$ | H | Me | H | H | |
| 202 | CO—NH$_2$ | H | Me | H | H | |
| 203 | CO—NHMe | H | Me | H | H | |
| 204 | CO—NHEt | H | Me | H | H | |
| 205 | CO—NH-n-Pr | H | Me | H | H | |
| 206 | CO—NH-i-Pr | H | Me | H | H | |
| 207 | CO—NH-c-Pr | H | Me | H | H | |
| 208 | CO—NH-n-Pr | H | Me | H | H | |
| 209 | CO—NH-n-Bu | H | Me | H | H | |
| 210 | CO—NMe$_2$ | H | Me | H | H | |
| 211 | CO—NEt$_2$ | H | Me | H | H | |
| 212 | CO—NHNH$_2$ | H | Me | H | H | |
| 213 | CN | H | Me | H | H | |
| 214 | CHO | H | Me | H | H | |
| 215 | CO—Me | H | Me | H | H | |
| 216 | CO—Et | H | Me | H | H | |
| 217 | CO—OH | H | OH | H | H | |
| 218 | CO—OMe | H | OH | H | H | |
| 219 | CO—OEt | H | OH | H | H | |
| 220 | CO—O-n-Pr | H | OH | H | H | |
| 221 | CO—O-n-Bu | H | OH | H | H | |
| 222 | CO—O-c-Pr | H | OH | H | H | |
| 223 | CO—O—CH$_2$CH$_2$OH | H | OH | H | H | |
| 224 | CO—O—C$_{12}$H$_{25}$ | H | OH | H | H | |
| 225 | CO—O—C$_{16}$H$_{33}$ | H | OH | H | H | |
| 226 | CO—NH$_2$ | H | OH | H | H | |
| 227 | CO—NHMe | H | OH | H | H | |
| 228 | CO—NHEt | H | OH | H | H | |
| 229 | CO—NH-n-Pr | H | OH | H | H | |
| 230 | CO—NH-i-Pr | H | OH | H | H | |
| 231 | CO—NH-c-Pr | H | OH | H | H | |
| 232 | CO—NH-n-Pr | H | OH | H | H | |
| 233 | CO—NH-n-Bu | H | OH | H | H | |
| 234 | CO—NMe$_2$ | H | OH | H | H | |
| 235 | CO—NEt$_2$ | H | OH | H | H | |
| 236 | CO—NHNH$_2$ | H | OH | H | H | |
| 237 | CN | H | OH | H | H | |
| 238 | CHO | H | OH | H | H | |
| 239 | CO—Me | H | OH | H | H | |
| 240 | CO—Et | H | OH | H | H | |
| 241 | CO—OH | H | OAc | H | H | |
| 242 | CO—OMe | H | OAc | H | H | |
| 243 | CO—OEt | H | OAc | H | H | |
| 244 | CO—O-n-Pr | H | OAc | H | H | |
| 245 | CO—O-n-Bu | H | OAc | H | H | |
| 246 | CO—O-c-Pr | H | OAc | H | H | |
| 247 | CO—O—CH$_2$CH$_2$OH | H | OAc | H | H | |
| 248 | CO—O—C$_{12}$H$_{25}$ | H | OAc | H | H | |
| 249 | CO—O—C$_{16}$H$_{33}$ | H | OAc | H | H | |

TABLE 1-continued

Compounds of the formula (I) (Ia)

| Comp. No. | R¹ | R(x) | R(y) | R(z) | R | Physical data |
|---|---|---|---|---|---|---|
| 250 | CO—NH$_2$ | H | OAc | H | H | |
| 251 | CO—NHMe | H | OAc | H | H | |
| 252 | CO—NHEt | H | OAc | H | H | |
| 253 | CO—NH-n-Pr | H | OAc | H | H | |
| 254 | CO—NH-i-Pr | H | OAc | H | H | |
| 255 | CO—NH-c-Pr | H | OAc | H | H | |
| 256 | CO—NH-n-Pr | H | OAc | H | H | |
| 257 | CO—NH-n-Bu | H | OAc | H | H | |
| 258 | CO—NMe$_2$ | H | OAc | H | H | |
| 259 | CO—NEt$_2$ | H | OAc | H | H | |
| 260 | CO—NHNH$_2$ | H | OAc | H | H | |
| 261 | CN | H | OAc | H | H | |
| 262 | CHO | H | OAc | H | H | |
| 263 | CO—Me | H | OAc | H | H | |
| 264 | CO—Et | H | OAc | H | H | |
| 265 | CO—OH | H | OMe | H | H | |
| 266 | CO—OMe | H | OMe | H | H | |
| 267 | CO—OEt | H | OMe | H | H | |
| 268 | CO—O-n-Pr | H | OMe | H | H | |
| 269 | CO—O-n-Bu | H | OMe | H | H | |
| 270 | CO—O-c-Pr | H | OMe | H | H | |
| 271 | CO—O—CH$_2$CH$_2$OH | H | OMe | H | H | |
| 272 | CO—O—C$_{12}$H$_{25}$ | H | OMe | H | H | |
| 273 | CO—O—C$_{16}$H$_{33}$ | H | OMe | H | H | |
| 274 | CO—NH$_2$ | H | OMe | H | H | |
| 275 | CO—NHMe | H | OMe | H | H | |
| 276 | CO—NHEt | H | OMe | H | H | |
| 277 | CO—NH-n-Pr | H | OMe | H | H | |
| 278 | CO—NH-i-Pr | H | OMe | H | H | |
| 279 | CO—NH-c-Pr | H | OMe | H | H | |
| 280 | CO—NH-n-Pr | H | OMe | H | H | |
| 281 | CO—NH-n-Bu | H | OMe | H | H | |
| 282 | CO—NMe$_2$ | H | OMe | H | H | |
| 283 | CO—NEt$_2$ | H | OMe | H | H | |
| 284 | CO—NHNH$_2$ | H | OMe | H | H | |
| 285 | CN | H | OMe | H | H | |
| 286 | CHO | H | OMe | H | H | |
| 287 | CO—Me | H | OMe | H | H | |
| 288 | CO—Et | H | OMe | H | H | |
| 289 | CO—OH | H | F | H | H | |
| 290 | CO—OMe | H | F | H | H | |
| 291 | CO—OEt | H | F | H | H | |
| 292 | CO—O-n-Pr | H | F | H | H | |
| 293 | CO—O-n-Bu | H | F | H | H | |
| 294 | CO—O-c-Pr | H | F | H | H | |
| 295 | CO—O—CH$_2$CH$_2$OH | H | F | H | H | |
| 296 | CO—O—C$_{12}$H$_{25}$ | H | F | H | H | |
| 297 | CO—O—C$_{16}$H$_{33}$ | H | F | H | H | |
| 298 | CO—NH$_2$ | H | F | H | H | |
| 299 | CO—NHMe | H | F | H | H | |
| 300 | CO—NHEt | H | F | H | H | |
| 301 | CO—NH-n-Pr | H | F | H | H | |
| 302 | CO—NH-i-Pr | H | F | H | H | |
| 303 | CO—NH-c-Pr | H | F | H | H | |
| 304 | CO—NH-n-Pr | H | F | H | H | |
| 305 | CO—NH-n-Bu | H | F | H | H | |
| 306 | CO—NMe$_2$ | H | F | H | H | |
| 307 | CO—NEt$_2$ | H | F | H | H | |
| 308 | CO—NHNH$_2$ | H | F | H | H | |
| 309 | CN | H | F | H | H | |
| 310 | CHO | H | F | H | H | |
| 311 | CO—Me | H | F | H | H | |
| 312 | CO—Et | H | F | H | H | |
| 313 | CO—OH | H | Cl | H | H | |
| 314 | CO—OMe | H | Cl | H | H | |
| 315 | CO—OEt | H | Cl | H | H | |
| 316 | CO—O-n-Pr | H | Cl | H | H | |
| 317 | CO—O-n-Bu | H | Cl | H | H | |
| 318 | CO—O-c-Pr | H | Cl | H | H | |
| 319 | CO—O—CH$_2$CH$_2$OH | H | Cl | H | H | |
| 320 | CO—O—C$_{12}$H$_{25}$ | H | Cl | H | H | |
| 321 | CO—O—C$_{16}$H$_{33}$ | H | Cl | H | H | |
| 322 | CO—NH$_2$ | H | Cl | H | H | |
| 323 | CO—NHMe | H | Cl | H | H | |
| 324 | CO—NHEt | H | Cl | H | H | |
| 325 | CO—NH-n-Pr | H | Cl | H | H | |
| 326 | CO—NH-i-Pr | H | Cl | H | H | |
| 327 | CO—NH-c-Pr | H | Cl | H | H | |
| 328 | CO—NH-n-Pr | H | Cl | H | H | |
| 329 | CO—NH-n-Bu | H | Cl | H | H | |
| 330 | CO—NMe$_2$ | H | Cl | H | H | |
| 331 | CO—NEt$_2$ | H | Cl | H | H | |
| 332 | CO—NHNH$_2$ | H | Cl | H | H | |
| 333 | CN | H | Cl | H | H | |
| 334 | CHO | H | Cl | H | H | |
| 335 | CO—Me | H | Cl | H | H | |
| 336 | CO—Et | H | Cl | H | H | |
| 337 | CO—OH | H | H | Me | H | |
| 338 | CO—OMe | H | H | Me | H | |
| 339 | CO—OEt | H | H | Me | H | |
| 340 | CO—O-n-Pr | H | H | Me | H | |
| 341 | CO—O-n-Bu | H | H | Me | H | |
| 342 | CO—O-c-Pr | H | H | Me | H | |
| 343 | CO—O—CH$_2$CH$_2$OH | H | H | Me | H | |
| 344 | CO—O—C$_{12}$H$_{25}$ | H | H | Me | H | |
| 345 | CO—O—C$_{16}$H$_{33}$ | H | H | Me | H | |
| 346 | CO—NH$_2$ | H | H | Me | H | |
| 347 | CO—NHMe | H | H | Me | H | |
| 348 | CO—NHEt | H | H | Me | H | |
| 349 | CO—NH-n-Pr | H | H | Me | H | |
| 350 | CO—NH-i-Pr | H | H | Me | H | |
| 351 | CO—NH-c-Pr | H | H | Me | H | |
| 352 | CO—NH-n-Pr | H | H | Me | H | |
| 353 | CO—NH-n-Bu | H | H | Me | H | |
| 354 | CO—NMe$_2$ | H | H | Me | H | |
| 355 | CO—NEt$_2$ | H | H | Me | H | |
| 356 | CO—NHNH$_2$ | H | H | Me | H | |
| 357 | CN | H | H | Me | H | |
| 358 | CHO | H | H | Me | H | |
| 359 | CO—Me | H | H | Me | H | |
| 360 | CO—Et | H | H | Me | H | |
| 361 | CO—OH | H | H | OH | H | |
| 362 | CO—OMe | H | H | OH | H | |
| 363 | CO—OEt | H | H | OH | H | |
| 364 | CO—O-n-Pr | H | H | OH | H | |
| 365 | CO—O-n-Bu | H | H | OH | H | |
| 366 | CO—O-c-Pr | H | H | OH | H | |
| 367 | CO—O—CH$_2$CH$_2$OH | H | H | OH | H | |
| 368 | CO—O—C$_{12}$H$_{25}$ | H | H | OH | H | |
| 369 | CO—O—C$_{16}$H$_{33}$ | H | H | OH | H | |
| 370 | CO—NH$_2$ | H | H | OH | H | |
| 371 | CO—NHMe | H | H | OH | H | |
| 372 | CO—NHEt | H | H | OH | H | |
| 373 | CO—NH-n-Pr | H | H | OH | H | |
| 374 | CO—NH-i-Pr | H | H | OH | H | |
| 375 | CO—NH-c-Pr | H | H | OH | H | |
| 376 | CO—NH-n-Pr | H | H | OH | H | |
| 377 | CO—NH-n-Bu | H | H | OH | H | |
| 378 | CO—NMe$_2$ | H | H | OH | H | |
| 379 | CO—NEt$_2$ | H | H | OH | H | |

TABLE 1-continued

Compounds of the formula (I)

(Ia)

| Comp. No. | R¹ | R(x) | R(y) | R(z) | R | Physical data |
|---|---|---|---|---|---|---|
| 380 | CO—NHNH$_2$ | H | H | OH | H | |
| 381 | CN | H | H | OH | H | |
| 382 | CHO | H | H | OH | H | |
| 383 | CO—Me | H | H | OH | H | |
| 384 | CO—Et | H | H | OH | H | |
| 385 | CO—OH | H | H | OAc | H | |
| 386 | CO—OMe | H | H | OAc | H | |
| 387 | CO—OEt | H | H | OAc | H | |
| 388 | CO—O-n-Pr | H | H | OAc | H | |
| 389 | CO—O-n-Bu | H | H | OAc | H | |
| 390 | CO—O-c-Pr | H | H | OAc | H | |
| 391 | CO—O—CH$_2$CH$_2$OH | H | H | OAc | H | |
| 392 | CO—O—C$_{12}$H$_{25}$ | H | H | OAc | H | |
| 393 | CO—O—C$_{16}$H$_{33}$ | H | H | OAc | H | |
| 394 | CO—NH$_2$ | H | H | OAc | H | |
| 395 | CO—NHMe | H | H | OAc | H | |
| 396 | CO—NHEt | H | H | OAc | H | |
| 397 | CO—NH-n-Pr | H | H | OAc | H | |
| 398 | CO—NH-i-Pr | H | H | OAc | H | |
| 399 | CO—NH-c-Pr | H | H | OAc | H | |
| 400 | CO—NH-n-Pr | H | H | OAc | H | |
| 401 | CO—NH-n-Bu | H | H | OAc | H | |
| 402 | CO—NMe$_2$ | H | H | OAc | H | |
| 403 | CO—NEt$_2$ | H | H | OAc | H | |
| 404 | CO—NHNH$_2$ | H | H | OAc | H | |
| 405 | CN | H | H | OAc | H | |
| 406 | CHO | H | H | OAc | H | |
| 407 | CO—Me | H | H | OAc | H | |
| 408 | CO—Et | H | H | OAc | H | |
| 409 | CO—OH | H | H | OMe | H | |
| 410 | CO—OMe | H | H | OMe | H | |
| 411 | CO—OEt | H | H | OMe | H | |
| 412 | CO—O-n-Pr | H | H | OMe | H | |
| 413 | CO—O-n-Bu | H | H | OMe | H | |
| 414 | CO—O-c-Pr | H | H | OMe | H | |
| 415 | CO—O—CH$_2$CH$_2$OH | H | H | OMe | H | |
| 416 | CO—O—C$_{12}$H$_{25}$ | H | H | OMe | H | |
| 417 | CO—O—C$_{16}$H$_{33}$ | H | H | OMe | H | |
| 418 | CO—NH$_2$ | H | H | OMe | H | |
| 419 | CO—NHMe | H | H | OMe | H | |
| 420 | CO—NHEt | H | H | OMe | H | |
| 421 | CO—NH-n-Pr | H | H | OMe | H | |
| 422 | CO—NH-i-Pr | H | H | OMe | H | |
| 423 | CO—NH-c-Pr | H | H | OMe | H | |
| 424 | CO—NH-n-Pr | H | H | OMe | H | |
| 425 | CO—NH-n-Bu | H | H | OMe | H | |
| 426 | CO—NMe$_2$ | H | H | OMe | H | |
| 427 | CO—NEt$_2$ | H | H | OMe | H | |
| 428 | CO—NHNH$_2$ | H | H | OMe | H | |
| 429 | CN | H | H | OMe | H | |
| 430 | CHO | H | H | OMe | H | |
| 431 | CO—Me | H | H | OMe | H | |
| 432 | CO—Et | H | H | OMe | H | |
| 433 | CO—OH | H | H | F | H | |
| 434 | CO—OMe | H | H | F | H | |
| 435 | CO—OEt | H | H | F | H | |
| 436 | CO—O-n-Pr | H | H | F | H | |
| 437 | CO—O-n-Bu | H | H | F | H | |
| 438 | CO—O-c-Pr | H | H | F | H | |
| 439 | CO—O—CH$_2$CH$_2$OH | H | H | F | H | |
| 440 | CO—O—C$_{12}$H$_{25}$ | H | H | F | H | |
| 441 | CO—O—C$_{16}$H$_{33}$ | H | H | F | H | |
| 442 | CO—NH$_2$ | H | H | F | H | |
| 443 | CO—NHMe | H | H | F | H | |
| 444 | CO—NHEt | H | H | F | H | |
| 445 | CO—NH-n-Pr | H | H | F | H | |
| 446 | CO—NH-i-Pr | H | H | F | H | |
| 447 | CO—NH-c-Pr | H | H | F | H | |
| 448 | CO—NH-n-Pr | H | H | F | H | |
| 449 | CO—NH-n-Bu | H | H | F | H | |
| 450 | CO—NMe$_2$ | H | H | F | H | |
| 451 | CO—NEt$_2$ | H | H | F | H | |
| 452 | CO—NHNH$_2$ | H | H | F | H | |
| 453 | CN | H | H | F | H | |
| 454 | CHO | H | H | F | H | |
| 455 | CO—Me | H | H | F | H | |
| 456 | CO—Et | H | H | F | H | |
| 457 | CO—OH | H | H | Cl | H | |
| 458 | CO—OMe | H | H | Cl | H | |
| 459 | CO—OEt | H | H | Cl | H | |
| 460 | CO—O-n-Pr | H | H | Cl | H | |
| 461 | CO—O-n-Bu | H | H | Cl | H | |
| 462 | CO—O-c-Pr | H | H | Cl | H | |
| 463 | CO—O—CH$_2$CH$_2$OH | H | H | Cl | H | |
| 464 | CO—O—C$_{12}$H$_{25}$ | H | H | Cl | H | |
| 465 | CO—O—C$_{16}$H$_{33}$ | H | H | Cl | H | |
| 466 | CO—NH$_2$ | H | H | Cl | H | |
| 467 | CO—NHMe | H | H | Cl | H | |
| 468 | CO—NHEt | H | H | Cl | H | |
| 469 | CO—NH-n-Pr | H | H | Cl | H | |
| 470 | CO—NH-i-Pr | H | H | Cl | H | |
| 471 | CO—NH-c-Pr | H | H | Cl | H | |
| 472 | CO—NH-n-Pr | H | H | Cl | H | |
| 473 | CO—NH-n-Bu | H | H | Cl | H | |
| 474 | CO—NMe$_2$ | H | H | Cl | H | |
| 475 | CO—NEt$_2$ | H | H | Cl | H | |
| 476 | CO—NHNH$_2$ | H | H | Cl | H | |
| 477 | CN | H | H | Cl | H | |
| 478 | CHO | H | H | Cl | H | |
| 479 | CO—Me | H | H | Cl | H | |
| 480 | CO—Et | H | H | Cl | H | |
| 481 | CO—OH | Cl | H | Cl | H | |
| 482 | CO—OMe | Cl | H | Cl | H | |
| 483 | CO—OEt | Cl | H | Cl | H | |
| 484 | CO—O-n-Pr | Cl | H | Cl | H | |
| 485 | CO—O-n-Bu | Cl | H | Cl | H | |
| 486 | CO—O-c-Pr | Cl | H | Cl | H | |
| 487 | CO—O—CH$_2$CH$_2$OH | Cl | H | Cl | H | |
| 488 | CO—O—C$_{12}$H$_{25}$ | Cl | H | Cl | H | |
| 489 | CO—O—C$_{16}$H$_{33}$ | Cl | H | Cl | H | |
| 490 | CO—NH$_2$ | Cl | H | Cl | H | |
| 491 | CO—NHMe | Cl | H | Cl | H | |
| 492 | CO—NHEt | Cl | H | Cl | H | |
| 493 | CO—NH-n-Pr | Cl | H | Cl | H | |
| 494 | CO—NH-i-Pr | Cl | H | Cl | H | |
| 495 | CO—NH-c-Pr | Cl | H | Cl | H | |
| 496 | CO—NH-n-Pr | Cl | H | Cl | H | |
| 497 | CO—NH-n-Bu | Cl | H | Cl | H | |
| 498 | CO—NMe$_2$ | Cl | H | Cl | H | |
| 499 | CO—NEt$_2$ | Cl | H | Cl | H | |
| 500 | CO—NHNH$_2$ | Cl | H | Cl | H | |
| 501 | CN | Cl | H | Cl | H | |
| 502 | CHO | Cl | H | Cl | H | |
| 503 | CO—Me | Cl | H | Cl | H | |
| 504 | CO—Et | Cl | H | Cl | H | |
| 505 | CO—OH | Cl | Cl | H | H | |
| 506 | CO—OMe | Cl | Cl | H | H | |
| 507 | CO—OEt | Cl | Cl | H | H | |
| 508 | CO—O-n-Pr | Cl | Cl | H | H | |
| 509 | CO—O-n-Bu | Cl | Cl | H | H | |

TABLE 1-continued

Compounds of the formula (I)

(Ia)

| Comp. No. | R¹ | R(x) | R(y) | R(z) | R | Physical data |
|---|---|---|---|---|---|---|
| 510 | CO—O-c-Pr | Cl | Cl | H | H | |
| 511 | CO—O—CH$_2$CH$_2$OH | Cl | Cl | H | H | |
| 512 | CO—O—C$_{12}$H$_{25}$ | Cl | Cl | H | H | |
| 513 | CO—O—C$_{16}$H$_{33}$ | Cl | Cl | H | H | |
| 514 | CO—NH$_2$ | Cl | Cl | H | H | |
| 515 | CO—NHMe | Cl | Cl | H | H | |
| 516 | CO—NHEt | Cl | Cl | H | H | |
| 517 | CO—NH-n-Pr | Cl | Cl | H | H | |
| 518 | CO—NH-i-Pr | Cl | Cl | H | H | |
| 519 | CO—NH-c-Pr | Cl | Cl | H | H | |
| 520 | CO—NH-n-Pr | Cl | Cl | H | H | |
| 521 | CO—NH-n-Bu | Cl | Cl | H | H | |
| 522 | CO—NMe$_2$ | Cl | Cl | H | H | |
| 523 | CO—NEt$_2$ | Cl | Cl | H | H | |
| 524 | CO—NHNH$_2$ | Cl | Cl | H | H | |
| 525 | CN | Cl | Cl | H | H | |
| 526 | CHO | Cl | Cl | H | H | |
| 527 | CO—Me | Cl | Cl | H | H | |
| 528 | CO—Et | Cl | Cl | H | H | |
| 529 | CO—OH | Cl | H | H | 5-Cl | |
| 530 | CO—OMe | Cl | H | H | 5-Cl | |
| 531 | CO—OEt | Cl | H | H | 5-Cl | |
| 532 | CO—O-n-Pr | Cl | H | H | 5-Cl | |
| 533 | CO—O-n-Bu | Cl | H | H | 5-Cl | |
| 534 | CO—O-c-Pr | Cl | H | H | 5-Cl | |
| 535 | CO—O—CH$_2$CH$_2$OH | Cl | H | H | 5-Cl | |
| 536 | CO—O—C$_{12}$H$_{25}$ | Cl | H | H | 5-Cl | |
| 537 | CO—O—C$_{16}$H$_{33}$ | Cl | H | H | 5-Cl | |
| 538 | CO—NH$_2$ | Cl | H | H | 5-Cl | |
| 539 | CO—NHMe | Cl | H | H | 5-Cl | |
| 540 | CO—NHEt | Cl | H | H | 5-Cl | |
| 541 | CO—NH-n-Pr | Cl | H | H | 5-Cl | |
| 542 | CO—NH-i-Pr | Cl | H | H | 5-Cl | |
| 543 | CO—NH-c-Pr | Cl | H | H | 5-Cl | |
| 544 | CO—NH-n-Pr | Cl | H | H | 5-Cl | |
| 545 | CO—NH-n-Bu | Cl | H | H | 5-Cl | |
| 546 | CO—NMe$_2$ | Cl | H | H | 5-Cl | |
| 547 | CO—NEt$_2$ | Cl | H | H | 5-Cl | |
| 548 | CO—NHNH$_2$ | Cl | H | H | 5-Cl | |
| 549 | CN | Cl | H | H | 5-Cl | |
| 550 | CHO | Cl | H | H | 5-Cl | |
| 551 | CO—Me | Cl | H | H | 5-Cl | |
| 552 | CO—Et | Cl | H | H | 5-Cl | |
| 553 | CO—OH | F | H | H | 5-OMe | |
| 554 | CO—OMe | F | H | H | 5-OMe | |
| 555 | CO—OEt | F | H | H | 5-OMe | |
| 556 | CO—O-n-Pr | F | H | H | 5-OMe | |
| 557 | CO—O-n-Bu | F | H | H | 5-OMe | |
| 558 | CO—O-c-Pr | F | H | H | 5-OMe | |
| 559 | CO—O—CH$_2$CH$_2$OH | F | H | H | 5-OMe | |
| 560 | CO—O—C$_{12}$H$_{25}$ | F | H | H | 5-OMe | |
| 561 | CO—O—C$_{16}$H$_{33}$ | F | H | H | 5-OMe | |
| 562 | CO—NH$_2$ | F | H | H | 5-OMe | |
| 563 | CO—NHMe | F | H | H | 5-OMe | |
| 564 | CO—NHEt | F | H | H | 5-OMe | |
| 565 | CO—NH-n-Pr | F | H | H | 5-OMe | |
| 566 | CO—NH-i-Pr | F | H | H | 5-OMe | |
| 567 | CO—NH-c-Pr | F | H | H | 5-OMe | |
| 568 | CO—NH-n-Pr | F | H | H | 5-OMe | |
| 569 | CO—NH-n-Bu | F | H | H | 5-OMe | |
| 570 | CO—NMe$_2$ | F | H | H | 5-OMe | |
| 571 | CO—NEt$_2$ | F | H | H | 5-OMe | |
| 572 | CO—NHNH$_2$ | F | H | H | 5-OMe | |
| 573 | CN | F | H | H | 5-OMe | |
| 574 | CHO | F | H | H | 5-OMe | |
| 575 | CO—Me | F | H | H | 5-OMe | |
| 576 | CO—Et | F | H | H | 5-OMe | |
| 577 | CO—OH | F | H | H | 5-OMe | |
| 578 | CO—OMe | F | H | H | 6-OMe | |
| 579 | CO—OEt | F | H | H | 6-OMe | |
| 580 | CO—O-n-Pr | F | H | H | 6-OMe | |
| 581 | CO—O-n-Bu | F | H | H | 6-OMe | |
| 582 | CO—O-c-Pr | F | H | H | 6-OMe | |
| 583 | CO—O—CH$_2$CH$_2$OH | F | H | H | 6-OMe | |
| 584 | CO—O—C$_{12}$H$_{25}$ | F | H | H | 6-OMe | |
| 585 | CO—O—C$_{16}$H$_{33}$ | F | H | H | 6-OMe | |
| 586 | CO—NH$_2$ | F | H | H | 6-OMe | |
| 587 | CO—NHMe | F | H | H | 6-OMe | |
| 588 | CO—NHEt | F | H | H | 6-OMe | |
| 589 | CO—NH-n-Pr | F | H | H | 6-OMe | |
| 590 | CO—NH-i-Pr | F | H | H | 6-OMe | |
| 591 | CO—NH-c-Pr | F | H | H | 6-OMe | |
| 592 | CO—NH-n-Pr | F | H | H | 6-OMe | |
| 593 | CO—NH-n-Bu | F | H | H | 6-OMe | |
| 594 | CO—NMe$_2$ | F | H | H | 6-OMe | |
| 595 | CO—NEt$_2$ | F | H | H | 6-OMe | |
| 596 | CO—NHNH$_2$ | F | H | H | 6-OMe | |
| 597 | CN | F | H | H | 6-OMe | |
| 598 | CHO | F | H | H | 6-OMe | |
| 599 | CO—Me | F | H | H | 6-OMe | |
| 600 | CO—Et | F | H | H | 6-OMe | |
| 601 | CO—OH | OH | H | H | 6-OMe | |
| 602 | CO—OMe | OH | H | H | 6-OMe | |
| 603 | CO—OEt | OH | H | H | 6-OMe | |
| 604 | CO—O-n-Pr | OH | H | H | 6-OMe | |
| 605 | CO—O-n-Bu | OH | H | H | 6-OMe | |
| 606 | CO—O-c-Pr | OH | H | H | 6-OMe | |
| 607 | CO—O—CH$_2$CH$_2$OH | OH | H | H | 6-OMe | |
| 608 | CO—O—C$_{12}$H$_{25}$ | OH | H | H | 6-OMe | |
| 609 | CO—O—C$_{16}$H$_{33}$ | OH | H | H | 6-OMe | |
| 610 | CO—NH$_2$ | OH | H | H | 6-OMe | |
| 611 | CO—NHMe | OH | H | H | 6-OMe | |
| 612 | CO—NHEt | OH | H | H | 6-OMe | |
| 613 | CO—NH-n-Pr | OH | H | H | 6-OMe | |
| 614 | CO—NH-i-Pr | OH | H | H | 6-OMe | |
| 615 | CO—NH-c-Pr | OH | H | H | 6-OMe | |
| 616 | CO—NH-n-Pr | OH | H | H | 6-OMe | |
| 617 | CO—NH-n-Bu | OH | H | H | 6-OMe | |
| 618 | CO—NMe$_2$ | OH | H | H | 6-OMe | |
| 619 | CO—NEt$_2$ | OH | H | H | 6-OMe | |
| 620 | CO—NHNH$_2$ | OH | H | H | 6-OMe | |
| 621 | CN | OH | H | H | 6-OMe | |
| 622 | CHO | OH | H | H | 6-OMe | |
| 623 | CO—Me | OH | H | H | 6-OMe | |
| 624 | CO—Et | OH | H | H | 6-OMe | |
| 625 | CO—OH | F | OH | H | H | |
| 626 | CO—OMe | F | OH | H | H | |
| 627 | CO—OEt | F | OH | H | H | |
| 628 | CO—O-n-Pr | F | OH | H | H | |
| 629 | CO—O-n-Bu | F | OH | H | H | |
| 630 | CO—O-c-Pr | F | OH | H | H | |
| 631 | CO—O—CH$_2$CH$_2$OH | F | OH | H | H | |
| 632 | CO—O—C$_{12}$H$_{25}$ | F | OH | H | H | |
| 633 | CO—O—C$_{16}$H$_{33}$ | F | OH | H | H | |
| 634 | CO—NH$_2$ | F | OH | H | H | |
| 635 | CO—NHMe | F | OH | H | H | |
| 636 | CO—NHEt | F | OH | H | H | |
| 637 | CO—NH-n-Pr | F | OH | H | H | |
| 638 | CO—NH-i-Pr | F | OH | H | H | |
| 639 | CO—NH-c-Pr | F | OH | H | H | |

TABLE 1-continued

Compounds of the formula (I)

(Ia) structure with R(x), R(y), R(z), R substituents on benzene ring attached to CH=CH-R¹

| Comp. No. | R¹ | R(x) | R(y) | R(z) | R | Physical data |
|---|---|---|---|---|---|---|
| 640 | CO—NH-n-Pr | F | OH | H | H | |
| 641 | CO—NH-n-Bu | F | OH | H | H | |
| 642 | CO—NMe₂ | F | OH | H | H | |
| 643 | CO—NEt₂ | F | OH | H | H | |
| 644 | CO—NHNH₂ | F | OH | H | H | |
| 645 | CN | F | OH | H | H | |
| 646 | CHO | F | OH | H | H | |
| 647 | CO—Me | F | OH | H | H | |
| 648 | CO—Et | F | OH | H | H | |
| 649 | CO—OH | H | OH | OH | H | |
| 650 | CO—OMe | H | OH | OH | H | |
| 651 | CO—OEt | H | OH | OH | H | |
| 652 | CO—O-n-Pr | H | OH | OH | H | |
| 653 | CO—O-n-Bu | H | OH | OH | H | |
| 654 | CO—O-c-Pr | H | OH | OH | H | |
| 655 | CO—O—CH₂CH₂OH | H | OH | OH | H | |
| 656 | CO—O—C₁₂H₂₅ | H | OH | OH | H | |
| 657 | CO—O—C₁₆H₃₃ | H | OH | OH | H | |
| 658 | CO—NH₂ | H | OH | OH | H | |
| 659 | CO—NHMe | H | OH | OH | H | |
| 660 | CO—NHEt | H | OH | OH | H | |
| 661 | CO—NH-n-Pr | H | OH | OH | H | |
| 662 | CO—NH-i-Pr | H | OH | OH | H | |
| 663 | CO—NH-c-Pr | H | OH | OH | H | |
| 664 | CO—NH-n-Pr | H | OH | OH | H | |
| 665 | CO—NH-n-Bu | H | OH | OH | H | |
| 666 | CO—NMe₂ | H | OH | OH | H | |
| 667 | CO—NEt₂ | H | OH | OH | H | |
| 668 | CO—NHNH₂ | H | OH | OH | H | |
| 669 | CN | H | OH | OH | H | |
| 670 | CHO | H | OH | OH | H | |
| 671 | CO—Me | H | OH | OH | H | |
| 672 | CO—Et | H | OH | OH | H | |
| 673 | COOH | OH | OH | H | H | |
| 674 | CO—OMe | OH | OH | H | H | |
| 675 | CO—OEt | OH | OH | H | H | |
| 676 | CO—O-n-Pr | OH | OH | H | H | |
| 677 | CO—O-n-Bu | OH | OH | H | H | |
| 678 | CO—O-c-Pr | OH | OH | H | H | |
| 679 | CO—O—CH₂CH₂OH | OH | OH | H | H | |
| 680 | CO—O—C₁₂H₂₅ | OH | OH | H | H | |
| 681 | CO—O—C₁₆H₃₃ | OH | OH | H | H | |
| 682 | CO—NH₂ | OH | OH | H | H | |
| 683 | CO—NHMe | OH | OH | H | H | |
| 684 | CO—NHEt | OH | OH | H | H | |
| 685 | CO—NH-n-Pr | OH | OH | H | H | |
| 686 | CO—NH-i-Pr | OH | OH | H | H | |
| 687 | CO—NH-c-Pr | OH | OH | H | H | |
| 688 | CO—NH-n-Pr | OH | OH | H | H | |
| 689 | CO—NH-n-Bu | OH | OH | H | H | |
| 690 | CO—NMe₂ | OH | OH | H | H | |
| 691 | CO—NEt₂ | OH | OH | H | H | |
| 692 | CO—NHNH₂ | OH | OH | H | H | |
| 693 | CN | OH | OH | H | H | |
| 694 | CHO | OH | OH | H | H | |
| 695 | CO—Me | OH | OH | H | H | |
| 696 | CO—Et | OH | OH | H | H | |
| 697 | CO—OH | OH | H | OH | H | |
| 698 | CO—OMe | OH | H | OH | H | |
| 699 | CO—OEt | OH | H | OH | H | |
| 700 | CO—O-n-Pr | OH | H | OH | H | |
| 701 | CO—O-n-Bu | OH | H | OH | H | |
| 702 | CO—O-c-Pr | OH | H | OH | H | |
| 703 | CO—O—CH₂CH₂OH | OH | H | OH | H | |
| 704 | CO—O—C₁₂H₂₅ | OH | H | OH | H | |
| 705 | CO—O—C₁₆H₃₃ | OH | H | OH | H | |
| 706 | CO—NH₂ | OH | H | OH | H | |
| 707 | CO—NHMe | OH | H | OH | H | |
| 708 | CO—NHEt | OH | H | OH | H | |
| 709 | CO—NH-n-Pr | OH | H | OH | H | |
| 710 | CO—NH-i-Pr | OH | H | OH | H | |
| 711 | CO—NH-c-Pr | OH | H | OH | H | |
| 712 | CO—NH-n-Pr | OH | H | OH | H | |
| 713 | CO—NH-n-Bu | OH | H | OH | H | |
| 714 | CO—NMe₂ | OH | H | OH | H | |
| 715 | CO—NEt₂ | OH | H | OH | H | |
| 716 | CO—NHNH₂ | OH | H | OH | H | |
| 717 | CN | OH | H | OH | H | |
| 718 | CHO | OH | H | OH | H | |
| 719 | CO—Me | OH | H | OH | H | |
| 720 | CO—Et | OH | H | OH | H | |
| 721 | CO—OH | OH | H | H | 5-OH | |
| 722 | CO—OMe | OH | H | H | 5-OH | |
| 723 | CO—OEt | OH | H | H | 5-OH | |
| 724 | CO—O-n-Pr | OH | H | H | 5-OH | |
| 725 | CO—O-n-Bu | OH | H | H | 5-OH | |
| 726 | CO—O-c-Pr | OH | H | H | 5-OH | |
| 727 | CO—O—CH₂CH₂OH | OH | H | H | 5-OH | |
| 728 | CO—O—C₁₂H₂₅ | OH | H | H | 5-OH | |
| 729 | CO—O—C₁₆H₃₃ | OH | H | H | 5-OH | |
| 730 | CO—NH₂ | OH | H | H | 5-OH | |
| 731 | CO—NHMe | OH | H | H | 5-OH | |
| 732 | CO—NHEt | OH | H | H | 5-OH | |
| 733 | CO—NH-n-Pr | OH | H | H | 5-OH | |
| 734 | CO—NH-i-Pr | OH | H | H | 5-OH | |
| 735 | CO—NH-c-Pr | OH | H | H | 5-OH | |
| 736 | CO—NH-n-Pr | OH | H | H | 5-OH | |
| 737 | CO—NH-n-Bu | OH | H | H | 5-OH | |
| 738 | CO—NMe₂ | OH | H | H | 5-OH | |
| 739 | CO—NEt₂ | OH | H | H | 5-OH | |
| 740 | CO—NHNH₂ | OH | H | H | 5-OH | |
| 741 | CN | OH | H | H | 5-OH | |
| 742 | CHO | OH | H | H | 5-OH | |
| 743 | CO—Me | OH | H | H | 5-OH | |
| 744 | CO—Et | OH | H | H | 5-OH | |
| 745 | CO—OH | H | OH | H | 5-OH | |
| 746 | CO—OMe | H | OH | H | 5-OH | |
| 747 | CO—OEt | H | OH | H | 5-OH | |
| 748 | CO—O-n-Pr | H | OH | H | 5-OH | |
| 749 | CO—O-n-Bu | H | OH | H | 5-OH | |
| 750 | CO—O-c-Pr | H | OH | H | 5-OH | |
| 751 | CO—O—CH₂CH₂OH | H | OH | H | 5-OH | |
| 752 | CO—O—C₁₂H₂₅ | H | OH | H | 5-OH | |
| 753 | CO—O—C₁₆H₃₃ | H | OH | H | 5-OH | |
| 754 | CO—NH₂ | H | OH | H | 5-OH | |
| 755 | CO—NHMe | H | OH | H | 5-OH | |
| 756 | CO—NHEt | H | OH | H | 5-OH | |
| 757 | CO—NH-n-Pr | H | OH | H | 5-OH | |
| 758 | CO—NH-i-Pr | H | OH | H | 5-OH | |
| 759 | CO—NH-c-Pr | H | OH | H | 5-OH | |
| 760 | CO—NH-n-Pr | H | OH | H | 5-OH | |
| 761 | CO—NH-n-Bu | H | OH | H | 5-OH | |
| 762 | CO—NMe₂ | H | OH | H | 5-OH | |
| 763 | CO—NEt₂ | H | OH | H | 5-OH | |
| 764 | CO—NHNH₂ | H | OH | H | 5-OH | |
| 765 | CN | H | OH | H | 5-OH | |
| 766 | CHO | H | OH | H | 5-OH | |
| 767 | CO—Me | H | OH | H | 5-OH | |
| 768 | CO—Et | H | OH | H | 5-OH | |
| 769 | CO—OH | H | OH | OH | 5-OH | |

TABLE 1-continued

Compounds of the formula (I)

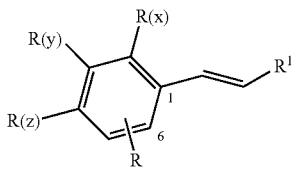

(Ia)

| Comp. No. | R¹ | R(x) | R(y) | R(z) | R | Physical data |
|---|---|---|---|---|---|---|
| 770 | CO—OMe | H | OH | OH | 5-OH | |
| 771 | CO—OEt | H | OH | OH | 5-OH | |
| 772 | CO—O-n-Pr | H | OH | OH | 5-OH | |
| 773 | CO—O-n-Bu | H | OH | OH | 5-OH | |
| 774 | CO—O-c-Pr | H | OH | OH | 5-OH | |
| 775 | CO—O—CH$_2$CH$_2$OH | H | OH | OH | 5-OH | |
| 776 | CO—O—C$_{12}$H$_{25}$ | H | OH | OH | 5-OH | |
| 777 | CO—O—C$_{16}$H$_{33}$ | H | OH | OH | 5-OH | |
| 778 | CO—NH$_2$ | H | OH | OH | 5-OH | |
| 779 | CO—NHMe | H | OH | OH | 5-OH | |
| 780 | CO—NHEt | H | OH | OH | 5-OH | |
| 781 | CO—NH-n-Pr | H | OH | OH | 5-OH | |
| 782 | CO—NH-i-Pr | H | OH | OH | 5-OH | |
| 783 | CO—NH-c-Pr | H | OH | OH | 5-OH | |
| 784 | CO—NH-n-Pr | H | OH | OH | 5-OH | |
| 785 | CO—NH-n-Bu | H | OH | OH | 5-OH | |
| 786 | CO—NMe$_2$ | H | OH | OH | 5-OH | |
| 787 | CO—NEt$_2$ | H | OH | OH | 5-OH | |
| 788 | CO—NHNH$_2$ | H | OH | OH | 5-OH | |
| 789 | CN | H | OH | OH | 5-OH | |
| 790 | CHO | H | OH | OH | 5-OH | |
| 791 | CO—Me | H | OH | OH | 5-OH | |
| 792 | CO—Et | H | OH | OH | 5-OH | |
| 793 | CO—OH | OH | OMe | H | H | |
| 794 | CO—OMe | OH | OMe | H | H | |
| 795 | CO—OEt | OH | OMe | H | H | |
| 796 | CO—O-n-Pr | OH | OMe | H | H | |
| 797 | CO—O-n-Bu | OH | OMe | H | H | |
| 798 | CO—O-c-Pr | OH | OMe | H | H | |
| 799 | CO—O—CH$_2$CH$_2$OH | OH | OMe | H | H | |
| 800 | CO—O—C$_{12}$H$_{25}$ | OH | OMe | H | H | |
| 801 | CO—O—C$_{16}$H$_{33}$ | OH | OMe | H | H | |
| 802 | CO—NH$_2$ | OH | OMe | H | H | |
| 803 | CO—NHMe | OH | OMe | H | H | |
| 804 | CO—NHEt | OH | OMe | H | H | |
| 805 | CO—NH-n-Pr | OH | OMe | H | H | |
| 806 | CO—NH-i-Pr | OH | OMe | H | H | |
| 807 | CO—NH-c-Pr | OH | OMe | H | H | |
| 808 | CO—NH-n-Pr | OH | OMe | H | H | |
| 809 | CO—NH-n-Bu | OH | OMe | H | H | |
| 810 | CO—NMe$_2$ | OH | OMe | H | H | |
| 811 | CO—NEt$_2$ | OH | OMe | H | H | |
| 812 | CO—NHNH$_2$ | OH | OMe | H | H | |
| 813 | CN | OH | OMe | H | H | |
| 814 | CHO | OH | OMe | H | H | |
| 815 | CO—Me | OH | OMe | H | H | |
| 816 | CO—Et | OH | OMe | H | H | |
| 817 | CO—OH | OH | H | OMe | H | |
| 818 | CO—OMe | OH | H | OMe | H | |
| 819 | CO—OEt | OH | H | OMe | H | |
| 820 | CO—O-n-Pr | OH | H | OMe | H | |
| 821 | CO—O-n-Bu | OH | H | OMe | H | |
| 822 | CO—O-c-Pr | OH | H | OMe | H | |
| 823 | CO—O—CH$_2$CH$_2$OH | OH | H | OMe | H | |
| 824 | CO—O—C$_{12}$H$_{25}$ | OH | H | OMe | H | |
| 825 | CO—O—C$_{16}$H$_{33}$ | OH | H | OMe | H | |
| 826 | CO—NH$_2$ | OH | H | OMe | H | |
| 827 | CO—NHMe | OH | H | OMe | H | |
| 828 | CO—NHEt | OH | H | OMe | H | |
| 829 | CO—NH-n-Pr | OH | H | OMe | H | |
| 830 | CO—NH-i-Pr | OH | H | OMe | H | |
| 831 | CO—NH-c-Pr | OH | H | OMe | H | |
| 832 | CO—NH-n-Pr | OH | H | OMe | H | |
| 833 | CO—NH-n-Bu | OH | H | OMe | H | |
| 834 | CO—NMe$_2$ | OH | H | OMe | H | |

TABLE 1-continued

Compounds of the formula (I)

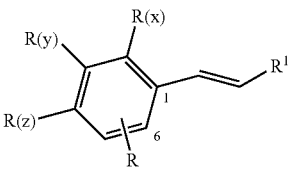

(Ia)

| Comp. No. | R¹ | R(x) | R(y) | R(z) | R | Physical data |
|---|---|---|---|---|---|---|
| 835 | CO—NEt$_2$ | OH | H | OMe | H | |
| 836 | CO—NHNH$_2$ | OH | H | OMe | H | |
| 837 | CN | OH | H | OMe | H | |
| 838 | CHO | OH | H | OMe | H | |
| 839 | CO—Me | OH | H | OMe | H | |
| 840 | CO—Et | OH | H | OMe | H | |
| 841 | CO—OH | H | H | OEt | H | |
| 842 | CO—OMe | H | H | OEt | H | |
| 843 | CO—OEt | H | H | OEt | H | |
| 844 | CO—O-n-Pr | H | H | OEt | H | |
| 845 | CO—O-n-Bu | H | H | OEt | H | |
| 846 | CO—O-c-Pr | H | H | OEt | H | |
| 847 | CO—O—CH$_2$CH$_2$OH | H | H | OEt | H | |
| 848 | CO—O—C$_{12}$H$_{25}$ | H | H | OEt | H | |
| 849 | CO—O—C$_{16}$H$_{33}$ | H | H | OEt | H | |
| 850 | CO—NH$_2$ | H | H | OEt | H | |
| 851 | CO—NHMe | H | H | OEt | H | |
| 852 | CO—NHEt | H | H | OEt | H | |
| 853 | CO—NH-n-Pr | H | H | OEt | H | |
| 854 | CO—NH-i-Pr | H | H | OEt | H | |
| 855 | CO—NH-c-Pr | H | H | OEt | H | |
| 856 | CO—NH-n-Pr | H | H | OEt | H | |
| 857 | CO—NH-n-Bu | H | H | OEt | H | |
| 858 | CO—NMe$_2$ | H | H | OEt | H | |
| 859 | CO—NEt$_2$ | H | H | OEt | H | |
| 860 | CO—NHNH$_2$ | H | H | OEt | H | |
| 861 | CN | H | H | OEt | H | |
| 862 | CHO | H | H | OEt | H | |
| 863 | CO—Me | H | H | OEt | H | |
| 864 | CO—Et | H | H | OEt | H | |
| 865 | CO—OH | H | OEt | H | H | |
| 866 | CO—OMe | H | OEt | H | H | |
| 867 | CO—OEt | H | OEt | H | H | |
| 868 | CO—O-n-Pr | H | OEt | H | H | |
| 869 | CO—O-n-Bu | H | OEt | H | H | |
| 870 | CO—O-c-Pr | H | OEt | H | H | |
| 871 | CO—O—CH$_2$CH$_2$OH | H | OEt | H | H | |
| 872 | CO—O—C$_{12}$H$_{25}$ | H | OEt | H | H | |
| 873 | CO—O—C$_{16}$H$_{33}$ | H | OEt | H | H | |
| 874 | CO—NH$_2$ | H | OEt | H | H | |
| 875 | CO—NHMe | H | OEt | H | H | |
| 876 | CO—NHEt | H | OEt | H | H | |
| 877 | CO—NH-n-Pr | H | OEt | H | H | |
| 878 | CO—NH-i-Pr | H | OEt | H | H | |
| 879 | CO—NH-c-Pr | H | OEt | H | H | |
| 880 | CO—NH-n-Pr | H | OEt | H | H | |
| 881 | CO—NH-n-Bu | H | OEt | H | H | |
| 882 | CO—NMe$_2$ | H | OEt | H | H | |
| 883 | CO—NEt$_2$ | H | OEt | H | H | |
| 884 | CO—NHNH$_2$ | H | OEt | H | H | |
| 885 | CN | H | OEt | H | H | |
| 886 | CHO | H | OEt | H | H | |
| 887 | CO—Me | H | OEt | H | H | |
| 888 | CO—Et | H | OEt | H | H | |
| 889 | CO—OH | OEt | H | H | H | |
| 890 | CO—OMe | OEt | H | H | H | |
| 891 | CO—OEt | OEt | H | H | H | |
| 892 | CO—O-n-Pr | OEt | H | H | H | |
| 893 | CO—O-n-Bu | OEt | H | H | H | |
| 894 | CO—O-c-Pr | OEt | H | H | H | |
| 895 | CO—O—CH$_2$CH$_2$OH | OEt | H | H | H | |
| 896 | CO—O—C$_{12}$H$_{25}$ | OEt | H | H | H | |
| 897 | CO—O—C$_{16}$H$_{33}$ | OEt | H | H | H | |
| 898 | CO—NH$_2$ | OEt | H | H | H | |
| 899 | CO—NHMe | OEt | H | H | H | |

TABLE 1-continued

Compounds of the formula (I)

(Ia)

R(y), R(x), R(z), R on benzene ring with CH=CH-R¹ substituent

| Comp. No. | R¹ | R(x) | R(y) | R(z) | R | Physical data |
|---|---|---|---|---|---|---|
| 900 | CO—NHEt | OEt | H | H | H | |
| 901 | CO—NH-n-Pr | OEt | H | H | H | |
| 902 | CO—NH-i-Pr | OEt | H | H | H | |
| 903 | CO—NH-c-Pr | OEt | H | H | H | |
| 904 | CO—NH-n-Pr | OEt | H | H | H | |
| 905 | CO—NH-n-Bu | OEt | H | H | H | |
| 906 | CO—NMe$_2$ | OEt | H | H | H | |
| 907 | CO—NEt$_2$ | OEt | H | H | H | |
| 908 | CO—NHNH$_2$ | OEt | H | H | H | |
| 909 | CN | OEt | H | H | H | |
| 910 | CHO | OEt | H | H | H | |
| 911 | CO—Me | OEt | H | H | H | |
| 912 | CO—Et | OEt | H | H | H | |
| 913 | CO—OH | OH | H | OEt | H | |
| 914 | CO—OMe | OH | H | OEt | H | |
| 915 | CO—OEt | OH | H | OEt | H | |
| 916 | CO—O-n-Pr | OH | H | OEt | H | |
| 917 | CO—O-n-Bu | OH | H | OEt | H | |
| 918 | CO—O-c-Pr | OH | H | OEt | H | |
| 919 | CO—O—CH$_2$CH$_2$OH | OH | H | OEt | H | |
| 920 | CO—O—C$_{12}$H$_{25}$ | OH | H | OEt | H | |
| 921 | CO—O—C$_{16}$H$_{33}$ | OH | H | OEt | H | |
| 922 | CO—NH$_2$ | OH | H | OEt | H | |
| 923 | CO—NHMe | OH | H | OEt | H | |
| 924 | CO—NHEt | OH | H | OEt | H | |
| 925 | CO—NH-n-Pr | OH | H | OEt | H | |
| 926 | CO—NH-i-Pr | OH | H | OEt | H | |
| 927 | CO—NH-c-Pr | OH | H | OEt | H | |
| 928 | CO—NH-n-Pr | OH | H | OEt | H | |
| 929 | CO—NH-n-Bu | OH | H | OEt | H | |
| 930 | CO—NMe$_2$ | OH | H | OEt | H | |
| 931 | CO—NEt$_2$ | OH | H | OEt | H | |
| 932 | CO—NHNH$_2$ | OH | H | OEt | H | |
| 933 | CN | OH | H | OEt | H | |
| 934 | CHO | OH | H | OEt | H | |
| 935 | CO—Me | OH | H | OEt | H | |
| 936 | CO—Et | OH | H | OEt | H | |

B FORMULATION EXAMPLES a) A dust is obtained by mixing 10 parts by weight of a compound of the formula (I) or of a combination of compound (I) with a pesticide and 90 parts by weight of talc as inert substance and comminuting the mixture in a hammer mill.

b) A wettable powder which is readily dispersible in water is obtained by mixing 25 parts by weight of a compound of the formula (I) or of a combination of compound (I) with a pesticide, 64 parts by weight of kaolin-containing quartz as inert substance, 10 parts by weight of potassium lignosulfonate and 1 part by weight of sodium oleoylmethyltaurinate as wetter and dispersant and grinding the mixture in a pinned-disk mill.

c) A dispersion concentrate which is readily dispersible in water is obtained by mixing 20 parts by weight of a compound of the formula (I) or of a compound (I) with a pesticide with 6 parts by weight of alkylphenol polyglycol ether (®Triton X 207), 3 parts by weight of isotridecanol polyglycol ether (8 EO) and 71 parts by weight of paraffinic mineral oil (boiling range for example approx. 255 to above 277° C.) and grinding the mixture in a ball mill to a fineness of below 5 microns.

d) An emulsifiable concentrate is obtained from 15 parts by weight of a compound of the formula (I) or of a combination of compound (I) with a pesticide, 75 parts by weight of cyclohexanone as the solvent and 10 parts by weight of ethoxylated nonylphenol as the emulsifier.

e) Water-dispersible granules are obtained by mixing 75 parts by weight of a compound of the formula (I) or of a combination of compound (I) with a pesticide, 10 parts by weight of calcium lignosulfonate, 5 parts by weight of sodium lauryl sulfate, 3 parts by weight of polyvinyl alcohol and 7 parts by weight of kaolin.

grinding the mixture on a pinned-disk mill and granulating the powder in a fluidized bed by spraying on water as the granulation liquid.

f) Water-dispersible granules are also obtained by homogenizing and precomminuting, on a colloid mill, 25 parts by weight of a compound of the formula (I) or of a combination of compound (I) with a pesticide, 5 parts by weight of sodium 2,2'-dinaphthylmethane-6,6'-disulfonate 2 parts by weight of sodium oleoylmethyltaurinate, 1 part by weight of polyvinyl alcohol, 17 parts by weight of calcium carbonate and 50 parts by weight of water, subsequently grinding the mixture in a bead mill and atomizing and drying the resulting suspension in a spray tower by means of a single-substance nozzle.

C) BIOLOGICAL EXAMPLES

C1) Herbicide and Safener in Tank Mix as Spray Application

C1.1) Herbicide and Safener Pre-Emergence Application by the Tank Mix Method

Seeds of various crop plants and weed species were sown in sandy loam soil in round plastic pots of a diameter of 13 cm and covered with a layer of sandy loam of a thickness of about 1 cm. Herbicides and safeners in the form of liquid (for example emulsion concentrates) or dry (for example water-dispersible powders) formulations were diluted with deionized water to the required concentrations and applied to the surface of the soil with a spray bar using a water application rate of 300 liters per hectare. In the experiment shown below, the safeners were used as 20 percent strength water-dispersible powders and the herbicide isoxaflutole was used as an aqueous suspension concentrate (see table 1.1.1).

The pots were placed in a greenhouse under favorable growth conditions. Visual scoring of the herbicidal action was carried out four weeks after the herbicide application. Evaluation was carried out on a percentage basis by comparison with untreated control plants (0%=no noticeable effect compared with the untreated plant, 100%=treated plant dies).

TABLE 1.1.1

Pre-emergence application: herbicide and safener in the tank mix method

| Safener | Application rate of safener [g of a.i./ha] | Herbicide H1 pre-emergence application [g of a.i./ha] | % damage in ZEAMA | Safener action as % damage reduction in crop plants | Herbicidal action as % damage in SETVI | Herbicidal action as % damage in CHEAL |
|---|---|---|---|---|---|---|
| — | — | 100 | 27 | — | 95 | 92 |
| Comp. 17 | 250 | 100 | 5 | 82 | 96 | 94 |
| Comp. 155 | 250 | 100 | 7 | 74 | 95 | 95 |

Abbreviations:
Herbicide H1 = isoxaflutole
Comp. 17 = 2-hydroxycinnamic acid (cf. tab. 1)
Comp. 155 = 2,4-dichlorocinnamic acid (cf. tab. 1)
ZEAMA = *Zea mays* (corn), cv. 'Lorenzo'
SETVI = *Setaria viridis*
CHEAL = *Chenopodium album*

C1.2) Post-Emergence Application of Herbicide and Safener by the Tank Mix Method Seeds of various crop plants and weed species were sown in sandy loam soil in round plastic pots of a diameter of 13 cm and covered with a layer of sandy loam of a thickness of about 1 cm. The pots were placed in a greenhouse under favorable growth conditions for a period of about two to three weeks, allowing the plants to reach a growth stage of 2 to 4 leaves. The herbicides in the form of liquid (for example emulsion concentrates) or dry (for example water-dispersible powders) formulations were mixed with a standard additive (based on rapeseed oil methyl ester), diluted with deionized water to the required concentrations and applied to the green parts of the plants and the uncovered part of the soil surface with a spray bar using a water application rate of 300 liters per hectare. In the experiment shown below, safener and the herbicide foramsulfuron were in each case used as 20 percent strength water-dispersible powder (results see table 1.2.1).

The pots were placed in a greenhouse under favorable growth conditions. Visual scoring of the herbicidal action was carried out four weeks after the herbicide application. Evaluation was carried out on a percentage basis by comparison with untreated control plants (0%=no noticeable effect compared with the untreated plant, 100%=treated plant dies).

TABLE 1.2.1

Post-emergence application: Herbicide and safener in tank mix method

| Safener | Application rate of safener [g of a.i./ha] | Herbicide H2 post-emergence application [g of a.i./ha] | % damage in ZEAMA | Safener action as % damage reduction in crop plants | Herbicidal action as % damage in SETVI | Herbicidal action as % damage in AMARE |
|---|---|---|---|---|---|---|
| — | — | 40 | 36 | — | 95 | 94 |
| Comp. 17 | 250 | 40 | 8 | 78 | 98 | 94 |
| Comp. 155 | 250 | 40 | 6 | 83 | 95 | 98 |
| Comp. 154 | 250 | 40 | 12 | 67 | 95 | 96 |
| Comp. 146 | 250 | 40 | 10 | 72 | 92 | 98 |
| Comp. 191 | 250 | 40 | 16 | 56 | 96 | 99 |

Abbreviations:
Herbicide H2 = foramsulfuron
Comp. 17 = 2-hydroxycinnamic acid (cf. tab. 1)
Comp. 155 = 2,4-dichlorocinnamic acid (cf. tab. 1)
Comp. 154 = 4-methoxycinnamic acid
Comp. 146 = 2-fluorocinnamic acid
Comp. 191 = ethyl 3-hydroxycinnamate
ZEAMA = *Zea mays* (corn), cv. 'Lorenzo'
SETVI = *Setaria viridis*
AMARE = *Amaranthus retroflexus*

Seeds of various crop plants and weed species were sown in sandy loam soil in round plastic pots of a diameter of 13 cm and covered with a layer of sandy loam of a thickness of about 1 cm. The pots were placed in a greenhouse under favorable growth conditions for a duration of about two to three weeks, allowing the plants to reach a growth stage of 2 to 4 leaves. The herbicides, in the form of liquid (for example emulsion concentrates, aqueous solutions) or dry (for example water-dispersible powders) formulations, were diluted with deionized water to the required concentrations and applied to the green parts of the plants and the uncovered part of the surface of the soil with a spray bar using a water application rate of 300 liters per hectare. In the experiment shown below, the safeners were used as 20 percent strength water-dispersible powders and the herbicide glufosinate-ammonium as a commercial 20 percent strength aqueous surfactant-containing solution (results see table 1.2.2).

The pots were placed in a greenhouse under favorable growth conditions. Visual scoring of the herbicidal action was carried out four weeks after the herbicidal application. Evaluation was carried out on a percentage basis by comparison with untreated control plants (0%=no noticeable effect compared with the untreated plant, 100%=treated plant dies).

TABLE 1.2.2

Post-emergence application: herbicide and safener in tank mix method

| Safener | Application rate of safener [g of a.i./ha] | Herbicide H3 post-emergence application [g of a.i./ha] | % damage in ZEAMA | Safener action as % damage reduction in crop plants | Herbicidal action as % damage in CHEAL | Herbicidal action as % damage in AMARE |
|---|---|---|---|---|---|---|
| — | — | 250 | 62 | — | 92 | 90 |
| Comp. 17 | 250 | 250 | 24 | 61 | 97 | 95 |
| Comp. 155 | 250 | 250 | 21 | 66 | 92 | 94 |

Abbreviations:
Herbicide H3 = glufosinate-ammonium
Comp. 17 = 2-hydroxycinnamic acid (cf. tab. 1)
Comp. 155 = 2,4-dichlorocinnamic acid (cf. tab. 1)
ZEAMA = *Zea mays* (corn), cv. 'Lorenzo'
CHEAL = *Chenopodium album*
AMARE = *Amaranthus retroflexus*

C2) Safener as Seed Dressing Followed by a Spray Application of Herbicide

C2.1) Seed Dressing

The number of crop plant seeds required for each application rate of safener was calculated. Sufficient seeds were weighed-out into glass bottles having a screw-on lid. The volume of the glass bottles was approximately twice that of the seeds weighed out.

The safeners were formulated as 20 percent strength water-dispersible powders. These formulations were weighed out to give the required application rates (g of a.i./kg of seed). The samples were added to the seed in the glass containers, and sufficient water to form a suitable seed dressing was then added. The glass bottles were closed and then mounted in an overhead shaker (which turns the bottles at moderate speed for a period of up to one hour) so that the seeds were uniformly covered with the seed dressing. The bottles were opened and the seed was ready for use in pre-emergence or post-emergence experiments, as described below.

C2.2) Pre-Emergence Application of Herbicides after Seed Dressing with Safener

The seeds which had been treated with safeners and untreated seeds as controls were sown in sandy loam soil in round plastic pots of a diameter of 13 cm and covered with a layer of sandy loam of a thickness of about 1 cm. The herbicides in the form of liquid (for example emulsion concentrates) or dry (for example water-dispersible powders) formulations were diluted with deionized water to the required concentrations and applied to the surface of the soil with a spray bar using a water application rate of 300 liters per hectare. In the two experiments shown below (results see tables 2.2.1 and 2.2.2), the herbicide isoxaflutole was used as an aqueous suspension concentrate.

The pots were placed in a greenhouse under favorable growth conditions. Visual scoring of the herbicidal action was carried out four weeks after the herbicide application. Evaluation was carried out on a percentage basis by comparison with untreated control plants (0%=no noticeable effect compared with the untreated plant, 100%=treated plant dies).

TABLE 2.2.1

Herbicide by the pre-emergence method after seed dressing with safener

| Safener for seed dressing | Application rate of safener [g of a.i./kg of seed] | Herbicide H1 pre-emergence application [g of a.i./ha] | % damage in ZEAMA | Safener action as % damage reduction in crop plants |
|---|---|---|---|---|
| — | — | 100 | 25 | — |
| Comp. 17 | 1 | 100 | 8 | 68 |
| Comp. 155 | 1 | 100 | 7 | 72 |

Abbreviations:
Herbicide H1 = isoxaflutole
Comp. 17 = 2-hydroxycinnamic acid (cf. tab. 1)
Comp. 155 = 2,4-dichlorocinnamic acid (cf. tab. 1)
ZEAMA = *Zea mays* (corn), cv. 'Lorenzo'

TABLE 2.2.2

Herbicide by the pre-emergence method after seed dressing with safener

| Safener for seed dressing | Application rate of safener [g of a.i./kg of seed] | Herbicide H1 pre-emergence application [g of a.i./ha] | % damage in GLXMA | Safener action as % damage reduction in crop plants |
|---|---|---|---|---|
| — | — | 100 | 83 | — |
| Comp. 17 | 1 | 100 | 33 | 60 |
| Comp. 155 | 1 | 100 | 30 | 64 |

Abbreviations:
Herbicide H1 = isoxaflutole
Comp. 17 = 2-hydroxycinnamic acid (cf. tab. 1)
Comp. 155 = 2,4-dichlorocinnamic acid (cf. tab. 1)
GLXMA = *Glycine max* (soybean), cv. 'Lambert'

C2.3) Post-Emergence Application of Herbicides after Seed Dressing with Safener

The seeds treated with safener and untreated seeds were sown in sandy loam soil in round plastic pots of a diameter of 13 cm and covered with a layer of sandy loam of a thickness of about 1 cm. The pots were placed in a greenhouse under favorable growth conditions for a period of about two to three weeks, allowing the plants to reach a growth stage of 2 to 4 leaves. The herbicides in the form of liquid (for example emulsion concentrates) or dry (for example water-dispersible powders) formulations were mixed with a standard additive (based on rapeseed oil methyl ester), diluted with deionized water to the required concentrations and applied to the green parts of the plants and the uncovered part of the soil surface with a spray bar using a water application rate of 300 liters per hectare. In the experiment shown below, the herbicide foramsulfuron was used as 20 percent strength water-dispersible powder (results see table 2.3.1).

The pots were placed in a greenhouse under favorable growth conditions. Visual scoring of the herbicidal action was carried out four weeks after the herbicide application. Evaluation was carried out on a percentage basis by comparison with untreated control plants (0%=no noticeable effect compared with the untreated plant, 100%=treated plant dies).

TABLE 2.3.1

Post-emergence application of herbicide after seed dressing with safener

| Safener for seed dressing | Application rate of safener [g of a.i./kg of seed] | Herbicide H2 post-emergence application [g of a.i./ha] | % damage in ZEAMA | Safener action as % damage reduction in crop plants |
| --- | --- | --- | --- | --- |
| — | — | 40 | 32 | — |
| Comp. 17 | 1 | 40 | 6 | 81 |
| Comp. 155 | 1 | 40 | 4 | 88 |

Abbreviations:
Herbicide H2 = foramsulfuron
Comp. 17 = 2-hydroxycinnamic acid (cf. tab. 1)
Comp. 155 = 2,4-dichlorocinnamic acid (cf. tab. 1)
ZEAMA = *Zea mays* (corn), cv. 'Lorenzo'

The invention claimed is:

1. A method for protecting crop plants or useful plants, against the phytotoxic actions of agrochemicals in said plants, comprising applying an effective amount of compounds of the formula (I) or salts thereof,

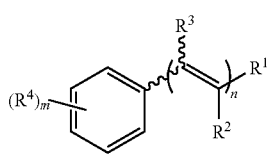

(I)

in which
$R^1$ is a radical of the formula

—CN or

—C(=X)—Y—R or

—C(X'R')(X"R")—Y—R in which
R is hydrogen or an unsubstituted or substituted hydrocarbon radical or an unsubstituted or substituted heterocyclic radical or acyl and R', R" independently of one another are each hydrogen, $(C_1-C_6)$alkyl, $(C_2-C_6)$alkenyl, $(C_2-C_6)$alkynyl or $(C_1-C_6)$alkanoyl, where the alkyl moiety of each of the 4 last-mentioned radicals is unsubstituted or substituted by one or more radicals selected from the group consisting of halogen, hydroxyl, $(C_1-C_6)$alkoxy and $(C_1-C_6)$haloalkoxy, or are directly attached to one another and are together a divalent group of the formula —$CH_2CH_2$— or —$CH_2CH_2CH_2$— or —$CH_2CH_2CH_2CH_2$—, where each of the 3 last-mentioned groups is unsubstituted or substituted by one or more radicals selected from the group consisting of halogen, hydroxyl, $(C_1-C_6)$alkyl, $(C_1-C_6)$haloalkyl, $(C_1-C_6)$alkoxy and $(C_1-C_6)$haloalkoxy, X is a divalent group of the formula O, S or $NR^a$ or N—$NR^aR^b$, where $R^a$ and $R^b$ are as defined below, X', X" independently of one another are each a divalent group of the formula 0, S or $NR^0$, where $R^0$ is hydrogen, $(C_1-C_6)$alkyl, $(C_1-C_6)$haloalkyl, $(C_1-C_6)$hydroxyalkyl, $(C_1-C_4)$alkoxy-$(C_1-C_4)$alkyl, $(C_2-C_6)$alkenyl or $(C_2-C_6)$alkynyl, Y is a direct bond or a group of the formula O, S, $NR^c$ or $NR^c$—$NR^dR^e$, where $R^c$, $R^d$ and $R^e$ are as defined below,
and $R^a$, $R^b$, $R^c$, $R^d$ and $R^e$ in the radicals X and Y are independently of one another and independently of the radical R each as defined for R or a radical of the formula —$OR^*$, where $R^*$ is, independently of R, as defined for R, $R^2$ and $R^3$ are each hydrogen, $(R^4)_m$ are m radicals of $R^4$, wherein $R^4$ is independently selected from the group consisting of halogen, SCN, CN, an unsubstituted or substituted hydrocarbon radical, an unsubstituted or substituted heterocyclic radical and radicals of the formula —$Z^*$-A,
where $Z^*$ is a group of the formula O or $S(O)_x$, where x is 0, 1 or 2, and A is hydrogen or an unsubstituted or substituted hydrocarbon radical or an unsubstituted or substituted heterocyclic radical or an acyl radical, with the proviso that when A is acyl, $Z^*$ can only be O or S,
and m is the integer 0, 1, 2, 3, 4 or 5,
n is the integer 1, 2, 3, 4, 5 or 6,
as safeners for the crop plants or useful plants, with the proviso that compounds of the formula (I) or salts thereof in which
$R^1$ is carboxyl,
$R^2$ and $R^3$ are each hydrogen,
$(R^4)_m$ is a hydroxyl radical, when m is 1, in any position or two radicals $R^4$, when m is 2, in any position, where in the latter case one radical is a hydroxyl group and the other radical is hydroxyl or methoxy, and
n is the number 1
are used as safeners for the crop plants or useful plants against phytotoxic actions of agrochemicals other than glyphosate.

2. The method as claimed in claim 1, wherein
R is hydrogen, $(C_1-C_{18})$alkyl, $(C_2-C_{18})$alkenyl, $(C_2-C_{18})$alkynyl, $(C_3-C_9)$cycloalkyl, $(C_5-C_9)$cycloalkenyl, $(C_3-$ $C_9$)cycloalkyl-($C_1$-$C_{12}$)alkyl, phenyl, phenyl-($C_1$-$C_{12}$) alkyl, heterocyclyl or heterocyclyl-($C_1$-$C_{12}$)alkyl,
  where each of the 10 last mentioned radicals is unsubstituted or substituted by one or more radicals selected from the group consisting of halogen, hydroxyl, amino, cyano, nitro, thiocyanato, ($C_1$-$C_4$)alkoxy, ($C_1$-$C_4$)haloalkoxy, ($C_2$-$C_4$)alkenyloxy, ($C_2$-$C_4$)haloalkenyloxy, ($C_1$-$C_4$)alkylthio, ($C_1$-$C_4$)alkylsulfinyl, ($C_1$-$C_4$)alkylsulfonyl, ($C_1$-$C_4$)haloalkylsulfinyl, ($C_1$-$C_4$)haloalkylsulfonyl, mono($C_1$-$C_4$)alkylamino, di($C_1$-$C_4$)alkylamino, ($C_1$-$C_4$)alkanoyl, ($C_1$-$C_4$)haloalkanoyl, [($C_1$-$C_4$)alkoxy]carbonyl, [($C_1$-$C_4$)haloalkoxy]carbonyl, aminocarbonyl, mono[($C_1$-$C_4$)alkylamino]carbonyl, di[($C_1$-$C_4$)alkylamino]carbonyl and, in the case of cyclic radicals, also ($C_1$-$C_4$)alkyl and ($C_1$-$C_4$)haloalkyl,
or
($C_1$-$C_6$)alkanoyl, ($C_1$-$C_4$)haloalkanoyl, [($C_1$-$C_4$)alkoxy]carbonyl, [($C_1$-$C_4$)haloalkoxy]carbonyl, phenylcarbonyl, phenoxycarbonyl, [phenyl-($C_1$-$C_4$)alkyl]carbonyl, [phenyl-($C_1$-$C_4$)alkoxy]carbonyl, where the phenyl ring of each of the 4 last-mentioned radicals is unsubstituted or substituted, aminocarbonyl, mono[($C_1$-$C_4$)alkylamino]carbonyl, di[($C_1$-$C_4$)alkylamino]carbonyl, ($C_1$-$C_4$)alkylsulfinyl, ($C_1$-$C_4$)alkylsulfonyl, ($C_1$-$C_4$)haloalkylsulfinyl or ($C_1$-$C_4$)haloalkylsulfonyl,
where R, including substituents, has 1 to 30 carbon atoms, and
R', R" independently of one another are each ($C_1$-$C_6$)alkyl, ($C_2$-$C_6$)alkenyl, ($C_2$-$C_6$)alkynyl or ($C_1$-$C_6$)alkanoyl, where each of the 4 last mentioned radicals is unsubstituted or substituted by one or more radicals selected from the group consisting of halogen, hydroxyl, ($C_1$-$C_6$)alkoxy and ($C_1$-$C_6$)haloalkoxy,
  or are directly attached to one another and are a divalent group of the formula —$CH_2CH_2$— or —$CH_2CH_2CH_2$— or —$CH_2CH_2CH_2CH_2$—, where each of the 3 last-mentioned groups is unsubstituted or substituted by one or more radicals selected from the group consisting of halogen, hydroxyl, ($C_1$-$C_4$)alkyl, ($C_1$-$C_4$)haloalkyl, ($C_1$-$C_4$)alkoxy and ($C_1$-$C_4$)haloalkoxy,
X is a divalent group of the formula O, S or $NR^a$ or N—$NR^aR^b$, where $R^a$ and $R^b$ are as defined below,
X', X" independently of one another are each a divalent group of the formula O, S or $NR^0$, where $R^0$ is hydrogen, ($C_1$-$C_4$)alkyl, ($C_1$-$C_4$)haloalkyl, ($C_1$-$C_4$)hydroxyalkyl, ($C_1$-$C_4$)alkoxy-($C_1$-$C_4$)alkyl, ($C_2$-$C_4$)alkenyl or ($C_2$-$C_4$)alkynyl,
Y is a direct bond or a divalent group of the formula O, S, $NR^c$ or $NR^c$—$NR^dR^e$, where $R^c$, $R^d$ and $R^e$ are as defined below, and
$R^a$, $R^b$, $R^c$, $R^d$ and $R^e$ in the radicals X and Y independently of one another and of the radical R are each as defined for R or a radical of the formula —OR*, where R* is, independently of R, as defined for R,
$R^2$ and $R^3$ are each hydrogen,
$(R^4)_m$ are m radicals $R^4$, where each of the radicals $R^4$ is independently of the others is selected from the group consisting of the radicals halogen, SCN, CN and ($C_1$-$C_{18}$)alkyl, ($C_2$-$C_{18}$)alkenyl, ($C_2$-$C_{18}$)alkynyl, ($C_3$-$C_9$)cycloalkyl, ($C_5$-$C_9$)cycloalkenyl, ($C_3$-$C_9$)cycloalkyl-($C_1$-$C_{12}$)alkyl, phenyl, phenyl-($C_1$-$C_{12}$)alkyl, heterocyclyl and heterocyclyl-($C_1$-$C_{12}$)alkyl,
  where each of the 10 last mentioned radicals is unsubstituted or substituted by one or more radicals selected from the group consisting of halogen, hydroxyl, amino, cyano, nitro, thiocyanato, ($C_1$-$C_4$)alkoxy, ($C_1$-$C_4$)haloalkoxy, ($C_2$-$C_4$)alkenyloxy, ($C_2$-$C_4$)haloalkenyloxy, ($C_1$-$C_4$)alkylthio, ($C_1$-$C_4$)alkylsulfinyl, ($C_1$-$C_4$)alkylsulfonyl, ($C_1$-$C_4$)haloalkylsulfinyl, ($C_1$-$C_4$)haloalkylsulfonyl, mono($C_1$-$C_4$)alkylamino, di($C_1$-$C_4$)alkylamino, ($C_1$-$C_4$)alkanoyl, ($C_1$-$C_4$)haloalkanoyl, [($C_1$-$C_4$)alkoxy]carbonyl, [($C_1$-$C_4$)haloalkoxy]carbonyl, aminocarbonyl, mono[($C_1$-$C_4$)alkylamino]carbonyl, di[($C_1$-$C_4$)alkylamino]carbonyl and, in the case of cyclic radicals, also ($C_1$-$C_4$)alkyl and ($C_1$-$C_4$)haloalkyl,
and radicals of the formula —Z*-A,
where
Z* is a group of the formula O or $S(O)_x$, where x=0, 1 or 2, and
A is hydrogen or ($C_1$-$C_{18}$)alkyl, ($C_2$-$C_{18}$)alkenyl, ($C_2$-$C_{18}$)alkynyl, ($C_3$-$C_9$)cycloalkyl, ($C_5$-$C_9$)cycloalkenyl, ($C_3$-$C_9$)cycloalkyl-($C_1$-$C_{12}$)alkyl, phenyl, phenyl-($C_1$-$C_{12}$)alkyl, heterocyclyl or heterocyclyl-($C_1$-$C_{12}$)alkyl,
  where each of the 10 last-mentioned radicals is unsubstituted or substituted by one or more radicals selected from the group consisting of halogen, hydroxyl, amino, cyano, nitro, thiocyanato, ($C_1$-$C_4$)alkoxy, ($C_1$-$C_4$)haloalkoxy, ($C_2$-$C_4$)alkenyloxy, ($C_2$-$C_4$)haloalkenyloxy, ($C_1$-$C_4$)alkylthio, ($C_1$-$C_4$)alkylsulfinyl, ($C_1$-$C_4$)alkylsulfonyl, ($C_1$-$C_4$)haloalkylsulfinyl, ($C_1$-$C_4$)haloalkylsulfonyl, mono($C_1$-$C_4$)alkylamino, di($C_1$-$C_4$)alkylamino, ($C_1$-$C_4$)alkanoyl, ($C_1$-$C_4$)haloalkanoyl, [($C_1$-$C_4$)alkoxy]carbonyl, [($C_1$-$C_4$)haloalkoxy]carbonyl, aminocarbonyl, mono[($C_1$-$C_4$)alkylamino]carbonyl, di[($C_1$-$C_4$)alkylamino]carbonyl and, in the case of cyclic radicals, also ($C_1$-$C_4$)alkyl and ($C_1$-$C_4$)haloalkyl,
  or is an acyl radical, provided that Z*, in the case that A=acyl, can only be O or S, where each radical $R^4$, including substituents, has 1 to 30 carbon atoms, and
m is the integer 0, 1, 2, 3, 4 or 5 and
n is the integer 1, 2, 3, 4, 5 or 6.

3. The method as claimed in claim 1, wherein
$R^1$ is a radical of the formula —C(=X)—Y—R or —C(X'R')(X"R")—Y—R,
in which
R is hydrogen, ($C_1$-$C_{12}$)alkyl, ($C_2$-$C_{12}$)alkenyl, ($C_2$-$C_{12}$)alkynyl, ($C_3$-$C_6$)cycloalkyl, ($C_5$-$C_6$)cycloalkenyl, ($C_3$-$C_6$)cycloalkyl-($C_1$-$C_4$)alkyl, phenyl, phenyl-($C_1$-$C_4$)alkyl, heterocyclyl or heterocyclyl-($C_1$-$C_4$)alkyl,
  where each of the 10 last mentioned radicals is unsubstituted or substituted by one or more radicals selected from the group consisting of halogen, hydroxyl, ($C_1$-$C_4$)alkoxy, ($C_1$-$C_4$)haloalkoxy, ($C_2$-$C_4$)alkenyloxy, ($C_2$-$C_4$)haloalkenyloxy, ($C_1$-$C_4$)alkylthio, ($C_1$-$C_4$)alkylsulfinyl, ($C_1$-$C_4$)alkylsulfonyl, ($C_1$-$C_4$)haloalkylsulfinyl, ($C_1$-$C_4$)haloalkylsulfonyl, mono($C_1$-$C_4$)alkylamino, di($C_1$-$C_4$)alkylamino, ($C_1$-$C_4$)alkanoyl, ($C_1$-$C_4$)haloalkanoyl, [($C_1$-$C_4$)alkoxy]carbonyl, [($C_1$-$C_4$)haloalkoxy]carbonyl, aminocarbonyl, mono[($C_1$-$C_4$)alkylamino]carbonyl, di[($C_1$-$C_4$)alkylamino]carbonyl and, in the case of cyclic radicals, also ($C_1$-$C_4$)alkyl and ($C_1$-$C_4$)haloalkyl,
or
($C_1$-$C_4$)alkanoyl, ($C_1$-$C_4$)haloalkanoyl, [($C_1$-$C_4$)alkoxy]carbonyl, [($C_1$-$C_4$)haloalkoxy]carbonyl, phenylcarbonyl, phenoxycarbonyl, [phenyl-($C_1$-$C_4$)alkyl]carbonyl, [phenyl-($C_1$-$C_4$)alkoxy]carbonyl, aminocarbonyl, mono[($C_1$-$C_4$)alkylamino]carbonyl, di[($C_1$-$C_4$)alkylamino]carbonyl, ($C_1$-$C_4$)alkylsulfinyl, ($C_1$-$C_4$)alkylsulfonyl, ($C_1$-$C_4$)haloalkylsulfinyl or ($C_1$-$C_4$)haloalkylsulfonyl, X is a divalent group of the formula O, S or $NR^a$ or $N-NR^aR^b$, where $R^a$ and $R^b$ are as defined below, X', X" independently of one another are each a divalent group of the formula O, S or $NR^0$, where $R^0$ is hydrogen, ($C_1$-$C_4$)alkyl, ($C_1$-$C_4$)haloalkyl, ($C_1$-$C_4$)hydroxyalkyl, ($C_2$-$C_4$)alkenyl or ($C_2$-$C_4$)alkynyl, Y is a direct bond or a divalent group of the formula O, S, $NR^c$ or $NR^c-NR^dR^e$, where $R^c$, $R^d$ and $R^e$ are as defined below, and $R^a$, $R^b$, $R^c$, $R^d$ and $R^e$ in the radicals X and Y independently of one another and of the radical R are as defined for R or a radical of the formula $-OR^*$, where $R^*$ is, independently of R, as defined for R, $(R^4)_m$ are m radicals $R^4$, wherein $R^4$ is independently selected from the group consisting of halogen, SCN, CN and ($C_1$-$C_6$)alkyl, ($C_2$-$C_6$)alkenyl, ($C_2$-$C_6$)alkynyl, ($C_3$-$C_6$) cycloalkyl, ($C_3$-$C_6$)cycloalkyl-($C_1$-$C_4$)alkyl, phenyl, phenyl-($C_1$-$C_4$)alkyl, heterocyclyl and heterocyclyl-($C_1$-$C_4$)alkyl, where each of the 9 last-mentioned radicals is unsubstituted or substituted by one or more radicals selected from the group consisting of halogen, hydroxyl, amino, cyano, nitro, ($C_1$-$C_4$)alkoxy, ($C_1$-$C_4$)haloalkoxy, ($C_2$-$C_4$)alkenyloxy, ($C_2$-$C_4$)haloalkenyloxy, ($C_1$-$C_4$)alkylthio, ($C_1$-$C_4$)alkylsulfinyl, ($C_1$-$C_4$)alkylsulfonyl, ($C_1$-$C_4$) haloalkylsulfinyl, ($C_1$-$C_4$)haloalkylsulfonyl, mono ($C_1$-$C_4$)alkylamino, di($C_1$-$C_4$)alkylamino, ($C_1$-$C_4$) alkanoyl, ($C_1$-$C_4$)haloalkanoyl, [($C_1$-$C_4$)alkoxy] carbonyl, [($C_1$-$C_4$)haloalkoxy]carbonyl, aminocarbonyl, mono[($C_1$-$C_4$)alkylamino]carbonyl, di[($C_1$-$C_4$)alkylamino]carbonyl and, in the case of cyclic radicals, also ($C_1$-$C_4$)alkyl and ($C_1$-$C_4$)haloalkyl, and radicals of the formula $-Z^*$-A, where $Z^*$ is a group of the formula O or $S(O)_x$, where x=0, 1 or 2, and A is hydrogen or ($C_1$-$C_8$)alkyl, ($C_2$-$C_8$)alkenyl, ($C_2$-$C_8$) alkynyl, ($C_3$-$C_6$)cycloalkyl, ($C_5$-$C_6$)cycloalkenyl, ($C_3$-$C_6$)cycloalkyl-($C_1$-$C_6$)alkyl, phenyl, phenyl-($C_1$-$C_6$)alkyl, heterocyclyl or heterocyclyl-($C_1$-$C_6$)alkyl, where each of the 10 last-mentioned radicals is unsubstituted or substituted by one or more radicals selected from the group consisting of halogen, hydroxyl, amino, cyano, nitro, thiocyanato, ($C_1$-$C_4$)alkoxy, ($C_1$-$C_4$)haloalkoxy, ($C_2$-$C_4$)alkenyloxy, ($C_2$-$C_4$)haloalkenyloxy, ($C_1$-$C_4$)alkylthio, ($C_1$-$C_4$)alkylsulfinyl, ($C_1$-$C_4$)alkylsulfonyl, ($C_1$-$C_4$)haloalkylsulfinyl, ($C_1$-$C_4$) haloalkylsulfonyl, mono($C_1$-$C_4$)alkylamino, di($C_1$-$C_4$)alkylamino, ($C_1$-$C_4$)alkanoyl, ($C_1$-$C_4$) haloalkanoyl, [($C_1$-$C_4$)alkoxy]carbonyl, [($C_1$-$C_4$) haloalkoxy]carbonyl, aminocarbonyl, mono[($C_1$-$C_4$) alkylamino]carbonyl, di[($C_1$-$C_4$)alkylamino] carbonyl and, in the case of cyclic radicals, also ($C_1$-$C_4$)alkyl and ($C_1$-$C_4$)haloalkyl, or, provided that $Z^*$, in the case that A=acyl, can only be O or S, an acyl radical selected from the group consisting of the radicals ($C_1$-$C_4$)alkanoyl, ($C_1$-$C_4$)haloalkanoyl, [($C_1$-$C_4$)alkoxy]carbonyl, [($C_1$-$C_4$)haloalkoxy]carbonyl, phenylcarbonyl, phenoxycarbonyl, [phenyl-($C_1$-$C_4$)alkyl]carbonyl, [phenyl-($C_1$-$C_4$)alkoxy]carbonyl, where the phenyl ring of each of the 4 last-mentioned radicals is unsubstituted or substituted by one or more radicals selected from the group consisting of halogen, ($C_1$-$C_4$)alkyl, ($C_1$-$C_4$)alkoxy, ($C_1$-$C_4$)haloalkyl, ($C_1$-$C_4$)haloalkoxy and ($C_1$-$C_4$)alkylthio.

4. The method as claimed in claim 1, wherein, the compounds of the formula (I) are compounds of the formula (I-1) or salts thereof

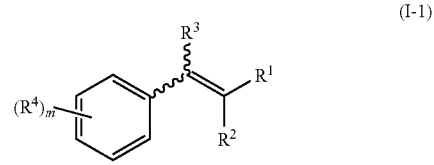

(I-1)

wherein $R^1$, $R^2$, $R^3$, $R^4$ and m are as defined for said compounds of formula (I).

5. The method as claimed in claim 1, wherein each $R^4$ is independently selected from the group consisting of halogen and ($C_1$-$C_4$)alkyl, which is unsubstituted or substituted by one or more radicals selected from the group consisting of halogen, hydroxyl, ($C_1$-$C_4$)alkoxy and ($C_1$-$C_4$)haloalkoxy, and radicals of the formula $-Z^*$-A, where $Z^*$ is O or S, and A is hydrogen or ($C_1$-$C_4$)alkyl, ($C_2$-$C_4$)alkenyl, ($C_2$-$C_4$) alkynyl or ($C_3$-$C_6$)cycloalkyl, where each of the 4 last-mentioned radicals is unsubstituted or substituted by one or more radicals selected from the group consisting of halogen, hydroxyl, ($C_1$-$C_4$)alkoxy, ($C_1$-$C_4$)haloalkoxy, ($C_1$-$C_4$)alkylthio, ($C_1$-$C_4$)alkylsulfinyl, ($C_1$-$C_4$)alkylsulfonyl, ($C_1$-$C_4$)alkanoyl, ($C_1$-$C_4$)haloalkanoyl, [($C_1$-$C_4$)alkoxy]carbonyl and, in the case of cyclic radicals, also ($C_1$-$C_4$)alkyl and ($C_1$-$C_4$)haloalkyl, or an acyl radical selected from the group consisting of the radicals ($C_1$-$C_4$)alkanoyl, ($C_1$-$C_4$)haloalkanoyl, [($C_1$-$C_4$) alkoxy]carbonyl, [($C_1$-$C_4$)haloalkoxy]carbonyl.

6. The method as claimed in claim 1, wherein an effective amount of one or more compounds of the formula (I) or salts thereof are applied to the plants, parts of plants, plant seeds or seed before, after or simultaneously with the agrochemical(s).

7. The method as claimed in claim 6, wherein the application is by the post-emergence method.

8. The method as claimed in claim 6, wherein the application is by treating the plant seeds.

9. The method as claimed in claim 6, wherein the application is by the pre-emergence method.

10. The method of claim 1 wherein

R' is a radical selected from the group consisting of —CN, —C(=X)—Y—R and

—C(X'R')(X"R")—Y—R wherein

R is hydrogen or an optionally substituted hydrocarbon radical, an optionally substituted heterocyclic radical or acyl;

R' and R" are independently hydrogen, ($C_1$-$C_6$)alkyl, ($C_2$-$C_6$)alkenyl, ($C_2$-$C_6$)alkynyl or ($C_1$-$C_6$)alkanoyl, where the alkyl moiety of each of the 4 last-mentioned radicals is optionally substituted by one or more radicals selected from the group consisting of halogen, hydroxyl, $(C_1-C_6)$alkoxy and $(C_1-C_6)$haloalkoxy, or are directly attached to one another and are together a divalent group of the formula —$CH_2CH_2$— or —$CH_2CH_2CH_2$— or —$CH_2CH_2CH_2CH_2$—, where each of the 3 last-mentioned groups is optionally substituted by one or more radicals selected from the group consisting of halogen, hydroxyl, $(C_1-C_6)$alkyl, $(C_1-C_6)$haloalkyl, $(C_1-C_6)$alkoxy and $(C_1-C_6)$haloalkoxy, X is a divalent group of the formula O, S or $NR^a$ or N—$NR^aR^b$, where $R^a$ and $R^b$ are as defined below, X' and X" are independently a divalent group of the formula O, S or $NR^0$, where $R^0$ is hydrogen, $(C_1-C_6)$alkyl, $(C_1-C_6)$haloalkyl, $(C_1-C_6)$hydroxyalkyl, $(C_1-C_4)$alkoxy-$(C_1-C_4)$alkyl, $(C_2-C_6)$alkenyl or $(C_2-C_6)$alkynyl, Y is a direct bond or a group of the formula O, S, $NR^c$ or $NR^c$—$NR^dR^e$, where $R^c$, $R^d$ and $R^e$ are as defined below, and $R^a$, $R^b$, $R^c$, $R^d$ and $R^e$ in the radicals X and Y are radicals as defined for R or a radical of the formula —OR*, where R* is, independently of R, as defined for R.

\* \* \* \* \*